(12) United States Patent
Hwang et al.

(10) Patent No.: US 8,043,726 B2
(45) Date of Patent: *Oct. 25, 2011

(54) SILANYLAMINE-BASED COMPOUND AND ORGANIC LIGHT EMITTING DIODE

(75) Inventors: Seok-Hwan Hwang, Suwon-si (KR); Young-Kook Kim, Suwon-si (KR); Yoon-Hyun Kwak, Suwon-si (KR); Jeoung-In Yi, Suwon-si (KR); Se-Jin Cho, Suwon-si (KR)

(73) Assignee: Samsung Mobile Display Co., Ltd. (KR)

( * ) Notice: Subject to any disclaimer, the term of this patent is extended or adjusted under 35 U.S.C. 154(b) by 254 days.

This patent is subject to a terminal disclaimer.

(21) Appl. No.: 12/378,601

(22) Filed: Feb. 17, 2009

(65) Prior Publication Data

US 2009/0206745 A1    Aug. 20, 2009

(30) Foreign Application Priority Data

Feb. 18, 2008 (KR) .................. 10-2008-0014421

(51) Int. Cl.
*H01L 51/54* (2006.01)
*H01J 1/63* (2006.01)
*C07F 7/10* (2006.01)

(52) U.S. Cl. ........ 428/690; 428/917; 313/504; 313/506; 548/406

(58) Field of Classification Search .................. None
See application file for complete search history.

(56) References Cited

U.S. PATENT DOCUMENTS 7,649,197 B2 * 1/2010 Iwaki et al. .................. 257/40
2008/0106188 A1 * 5/2008 Hwang et al. .............. 313/504

FOREIGN PATENT DOCUMENTS

JP   2008-133225 A   * 6/2008
KR   1020060048267 A   5/2006

OTHER PUBLICATIONS

Organometallics, (2004), vol. 23, No. 25, pp. 5958-5966.*
Organometallics, (2003), vol. 22, No. 2, pp. 321-327.*
Office Action issued by the Korean Patent Office on Jun. 27, 2009 in 4 pgs.

* cited by examiner

*Primary Examiner* — Dawn L Garrett
(74) *Attorney, Agent, or Firm* — Knobbe Martens Olson & Bear LLP

(57) ABSTRACT

Provided are a silanylamine-based compound of Formula 1 and an organic light emitting diode including an organic layer having the same:

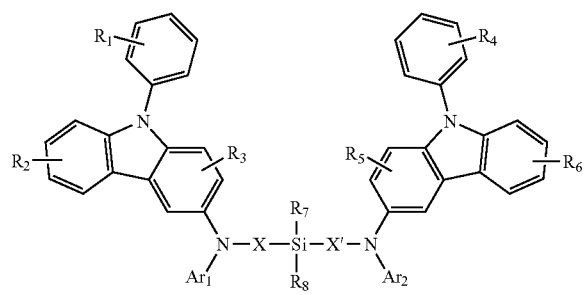

Formula 1 wherein $R_1$, $R_2$, $R_3$, $R_4$, $R_5$, $R_6$, $R_7$, $R_8$, $Ar_1$, $Ar_2$, X and X' are described herein. Embodiments of the silanylamine-based compound of Formula 1 exhibit superior electrical properties and high charge-transport properties, and can be efficiently used as hole injecting materials, hole transporting materials, and/or emitting materials suitable for phosphorescent and fluorescent organic light emitting diodes emitting light of all colors, including red, green, blue, and white. Furthermore, an organic light emitting diode having the silanylamine-based compound of Formula 1 can have high efficiency, low driving voltage, and high brightness.

20 Claims, 1 Drawing Sheet

SILANYLAMINE-BASED COMPOUND AND ORGANIC LIGHT EMITTING DIODE

CROSS-REFERENCE TO RELATED PATENT APPLICATION

This application claims the benefit of Korean Patent Application No. 10-2008-0014421, filed on Feb. 18, 2008 in the Korean Intellectual Property Office, the disclosure of which is incorporated by reference herein in its entirety.

BACKGROUND

1. Technical Field

The present disclosure relates to a silanylamine-based compound and an organic light emitting diode including an organic layer comprising the compound, and more particularly to a silanylamine-based compound with superior electrical stability and high charge transporting capability and a high glass transition temperature, which is able to prevent crystallization, and an organic light emitting diode including an organic layer comprising the silanylamine-based compound.

2. Description of the Related Art

Organic light emitting diodes are self light-emitting devices that exhibit wide viewing angles, excellent contrast, and quick response times, and thus have received a much attention recently. Moreover, organic light emitting diodes have excellent driving voltage characteristics and can produce multiple colors.

Typically, an organic light emitting diode has an anode/emitting layer (EML)/cathode structure. An organic light emitting diode can also have various other structures, such as an anode/hole transport layer (HTL)/EML/cathode structure and an anode/HTL/EML/electron injection layer (EIL)/cathode structure, which result from adding a hole injection layer (HIL), a HTL, and an EIL between the anode and the EML or between the EML and the cathode.

Polyphenyl compounds or anthracene derivatives have been used in the HTL, for example, as described in U.S. Pat. Nos. 6,596,415 and 6,465,115. However, lifetime, efficiency, and power consumption characteristics of an organic light emitting diode using these materials in a HIL and/or a HTL do not meet desired levels, and thus there is a need to improve these characteristics.

SUMMARY OF THE INVENTION

The present disclosure provides a material for forming an organic layer, which has excellent electrical stability, high charge transporting capability, and a high glass transition temperature, and which is able to prevent crystallization, and thus, is suitable for phosphorescent and fluorescent organic light emitting diodes emitting light of all colors including red, green, blue, and white, and a method of preparing the material. In addition, the present disclosure also provides an organic light emitting diode having high efficiency, low driving voltage, and high brightness by employing an organic layer including the material.

Some embodiments provide a compound of Formula 1, which are useful as hole injecting materials, hole transporting materials, and/or emitting materials in phosphorescent and/or fluorescent organic light emitting diodes of any colors. Embodiments of organic light emitting diodes comprising the compound of Formula 1 exhibit at least one of higher efficiency, lower driving voltage, and higher brightness.

One aspect provides a silanylamine-based compound represented by Formula 1 below:

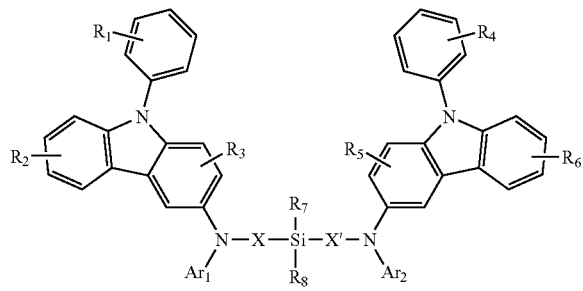

Formula 1

Here, $R_1$, $R_2$, $R_3$, $R_4$, $R_5$, $R_6$, $R_7$, and $R_8$ are each independently a hydrogen atom, a substituted or unsubstituted $C_1$-$C_{10}$ alkyl group, a substituted or unsubstituted $C_1$-$C_{10}$ alkoxy group, a fluorine atom, a cyano group, or an amine group, wherein adjacent groups among $R_1$, $R_2$, $R_3$, $R_4$, $R_5$, $R_6$, $R_7$, and $R_8$ may be bonded with one another to form a saturated or unsaturated carbon ring, $Ar_1$ and $Ar_2$ are each independently a substituted or unsubstituted $C_6$-$C_{20}$ aryl group, a substituted or unsubstituted $C_6$-$C_{20}$ aryloxy group, a substituted or unsubstituted $C_4$-$C_{20}$ heteroaryl group, or a substituted or unsubstituted $C_4$-$C_{20}$ condensed polycyclic group, X and X' are each independently a substituted or unsubstituted $C_6$-$C_{20}$ aryl group or a substituted or unsubstituted $C_4$-$C_{20}$ condensed polycyclic group.

Another aspect provides an organic light emitting diode including: a first electrode; a second electrode; and an organic layer including the silanylamine-based compound interposed between the first electrode and the second electrode.

The organic layer may be a hole injection layer (HIL), a hole transport layer (HTL) or an emitting layer (EML).

An organic light emitting diode including an organic layer having the silanylamine-based compound represented by Formula 1 can have low driving voltage, high brightness, high efficiency, and high current density.

Some embodiments provide a silanylamine-based compound of Formula 1 and an organic light emitting diode comprising the same:

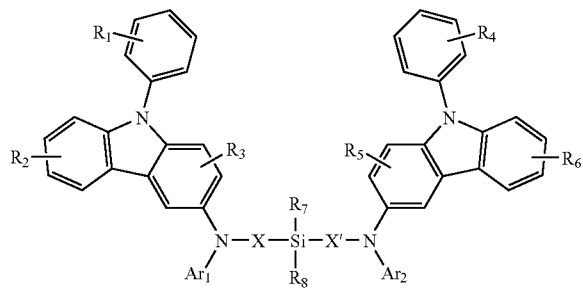

Formula 1 wherein $R_1$, $R_2$, $R_3$, $R_4$, $R_5$, $R_6$, $R_7$, and $R_8$ are each independently selected from the group consisting of a hydrogen atom, a substituted or unsubstituted $C_1$-$C_{10}$ alkyl group, a substituted or unsubstituted $C_1$-$C_{10}$ alkoxy group, a fluorine atom, a cyano group, and an amine group; adjacent $R_1$, $R_2$, $R_3$, $R_4$, $R_5$, $R_6$, $R_7$, and $R_8$ groups are optionally bonded with one another to form a saturated or unsaturated carbon ring; $Ar_1$ and $Ar_2$ are each independently selected from the group consisting of a substituted or unsubstituted $C_6$-$C_{20}$ aryl group, a substituted or unsubstituted $C_6$-$C_{20}$ aryloxy group, a substituted or unsubstituted $C_4$-$C_{20}$ heteroaryl group, and a substituted or unsubstituted $C_4$-$C_{20}$ condensed polycyclic group; and X and X' are each independently selected from the group consisting of a substituted or unsubstituted $C_6$-$C_{20}$ aryl group and a substituted or unsubstituted $C_4$-$C_{20}$ condensed polycyclic group.

In some embodiments, X is one of:

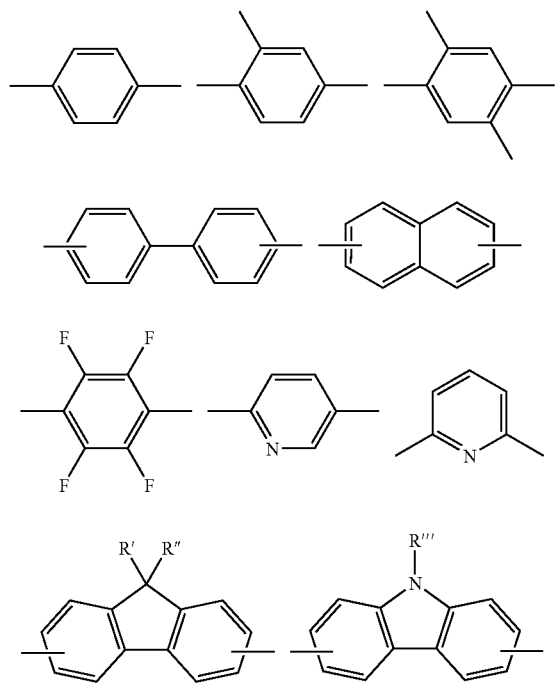

wherein R', R" and R'" are each independently selected from the group consisting of a hydrogen atom, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_6$-$C_{10}$ aryloxy group, a substituted or unsubstituted $C_6$-$C_{10}$ aryl group, a substituted or unsubstituted $C_4$-$C_{10}$ heteroaryl group, and a substituted or unsubstituted $C_4$-$C_{10}$ condensed polycyclic group.

In some embodiments, X is one of:

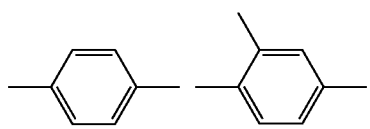

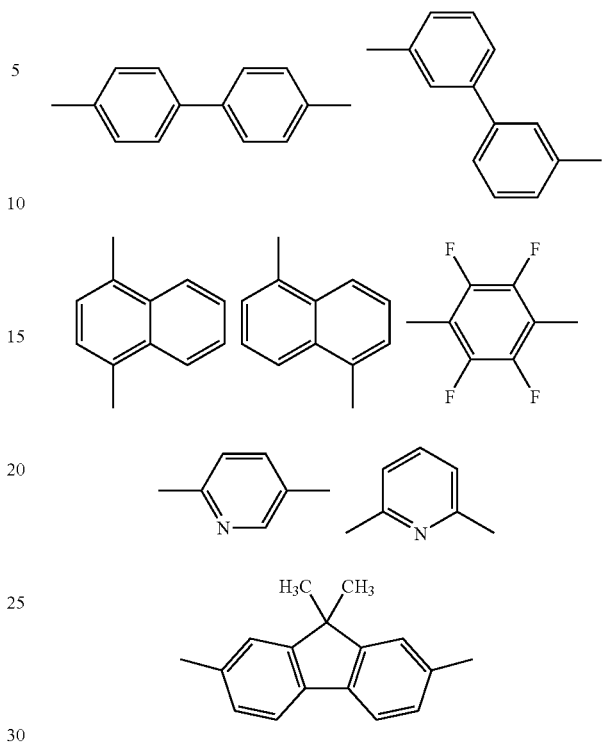

In some embodiments, $Ar_1$ and $Ar_2$ are each independently selected from the group consisting of a phenyl group, a $C_1$-$C_5$ alkylphenyl group, a $C_1$-$C_5$ alkoxyphenyl group, a cyanophenyl group, a phenoxyphenyl group, a fluorophenyl group, a naphthyl group, a $C_1$-$C_5$ alkylnaphthyl group, a $C_1$-$C_5$ alkoxynaphthyl group, a cyanonaphthyl group, a halonaphthyl group, a fluorenyl group, a carbazolyl group, a $C_1$-$C_5$ alkyl carbazolyl group, a biphenyl group, a $C_1$-$C_5$ alkyl biphenyl group, a $C_1$-$C_5$ alkoxy biphenyl group, and a pyridyl group. In some embodiments, $Ar_1$ and $Ar_2$ are each independently selected from the group consisting of a phenyl group, an ethylphenyl group, an ethylbiphenyl group, an o-, m-, or p-fluorophenyl group, a dichlorophenyl group, a cyanophenyl group, a dicyanophenyl group, a trifluorophenyl group, a methoxyphenyl group, an o-, m-, or p-tolyl group, a mesityl group, a phenoxyphenyl group, an (α,α-dimethyl benzene) phenyl group, an (N,N'-dimethyl)aminophenyl group, an (N,N'-diphenyl)aminophenyl group, a pentalenyl group, a naphthyl group, a methylnaphthyl group, an anthracenyl group, an azulenyl group, a heptalenyl group, an acenaphthylenyl group, a fluorenyl group, an anthraquinonyl group, a phenanthryl group, a triphenylene group, a pentaphenyl group, a hexaphenyl group and a carbazolyl group. In some embodiments, $Ar_1$ and $Ar_2$ are each independently a monocyclic to tricyclic aryl group, a fluorenyl group, a carbazolyl group, a phenyl group, a fluorophenyl group, a tolyl group, a naphthyl group, a biphenyl group and a cyanophenyl group, or a monocyclic to tricyclic aryl group comprising one to three substituents independently selected from the group consisting of a $C_1$-$C_4$ alkyl group, a $C_1$-$C_5$ alkoxy group, a cyano group, an amine group, a phenoxy group, a phenyl group, and a halogen atom.

In some embodiments, the compound of Formula 1 has one of the following structures:

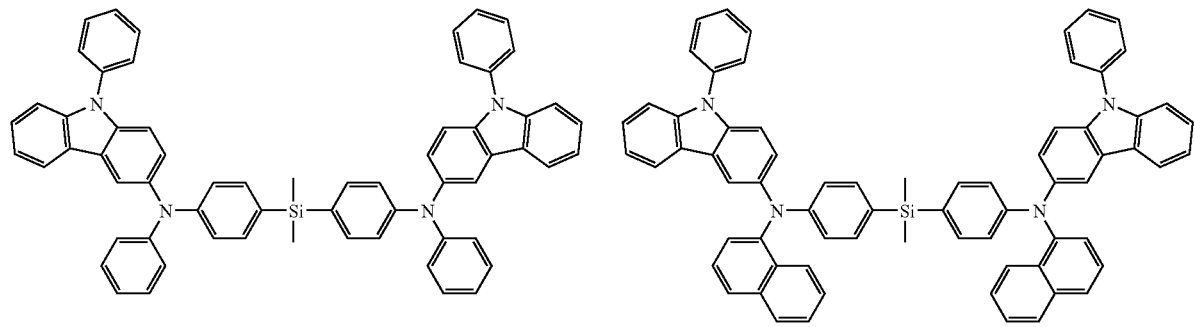
1
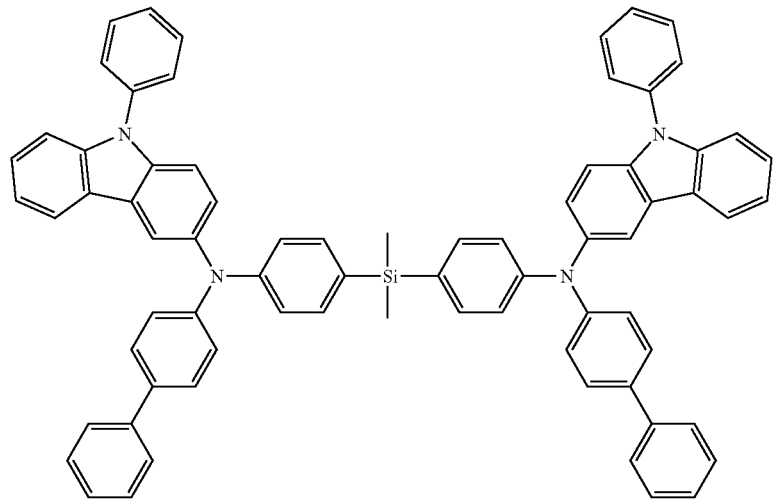
7
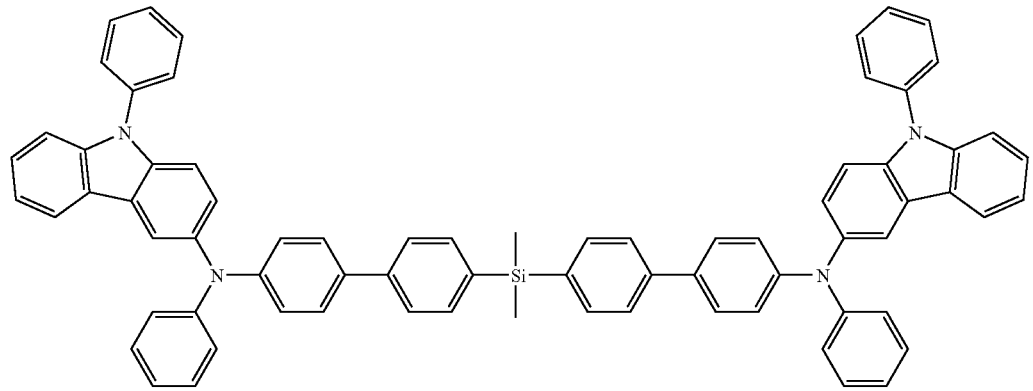
17
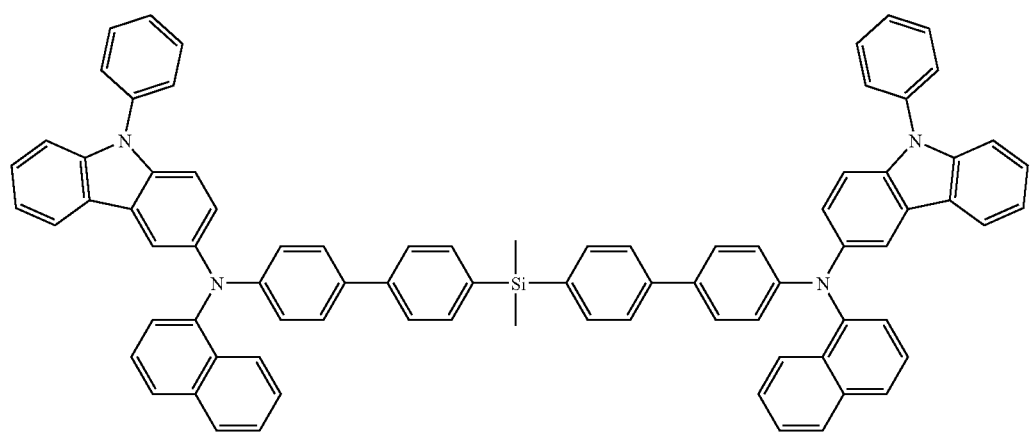
21

65
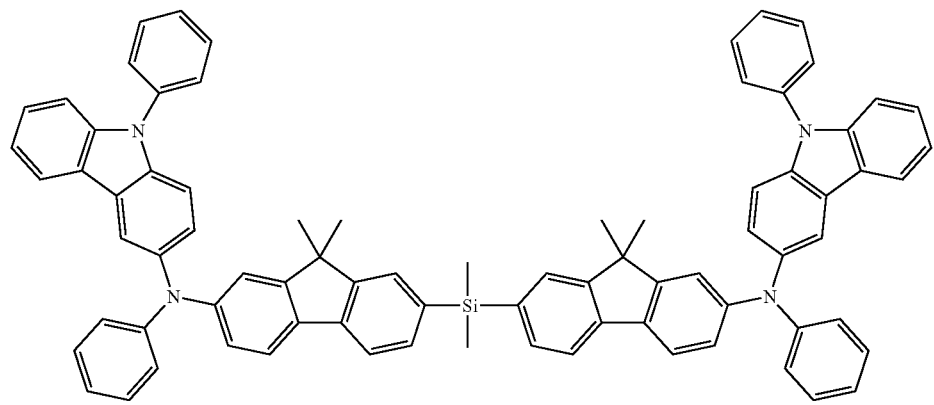
73
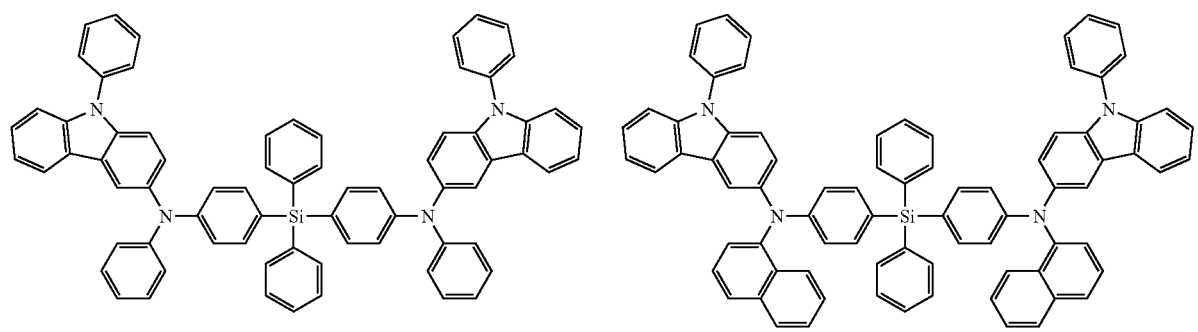
77
79
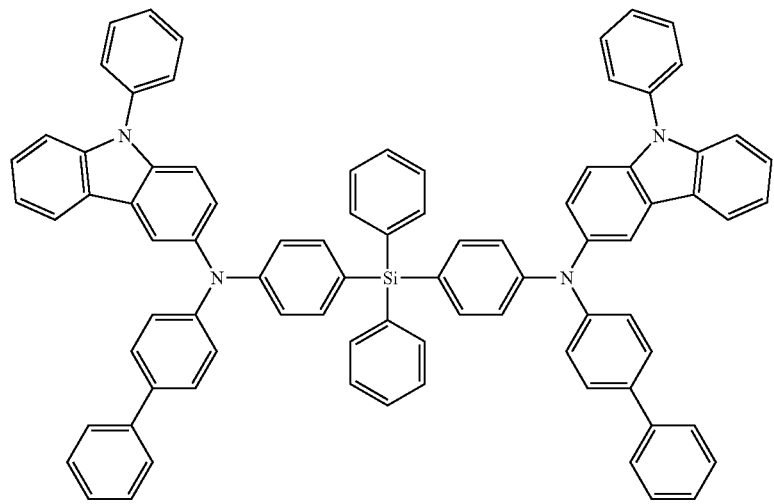
81
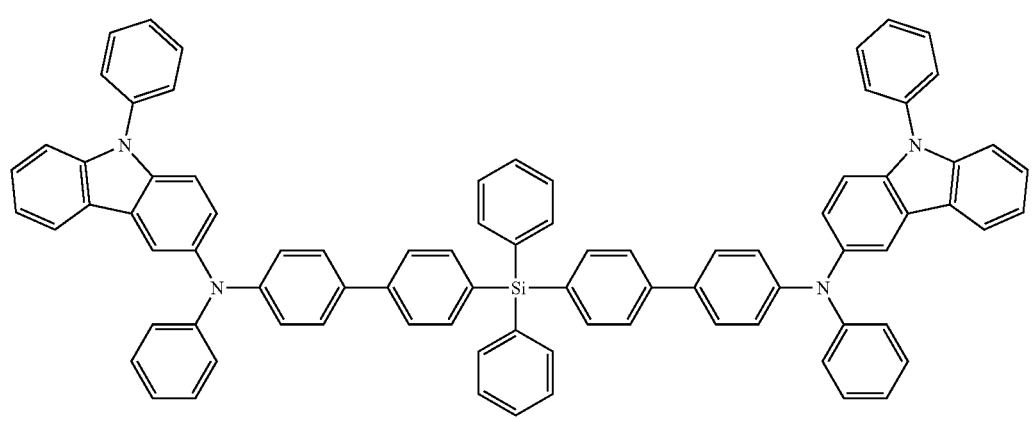

-continued

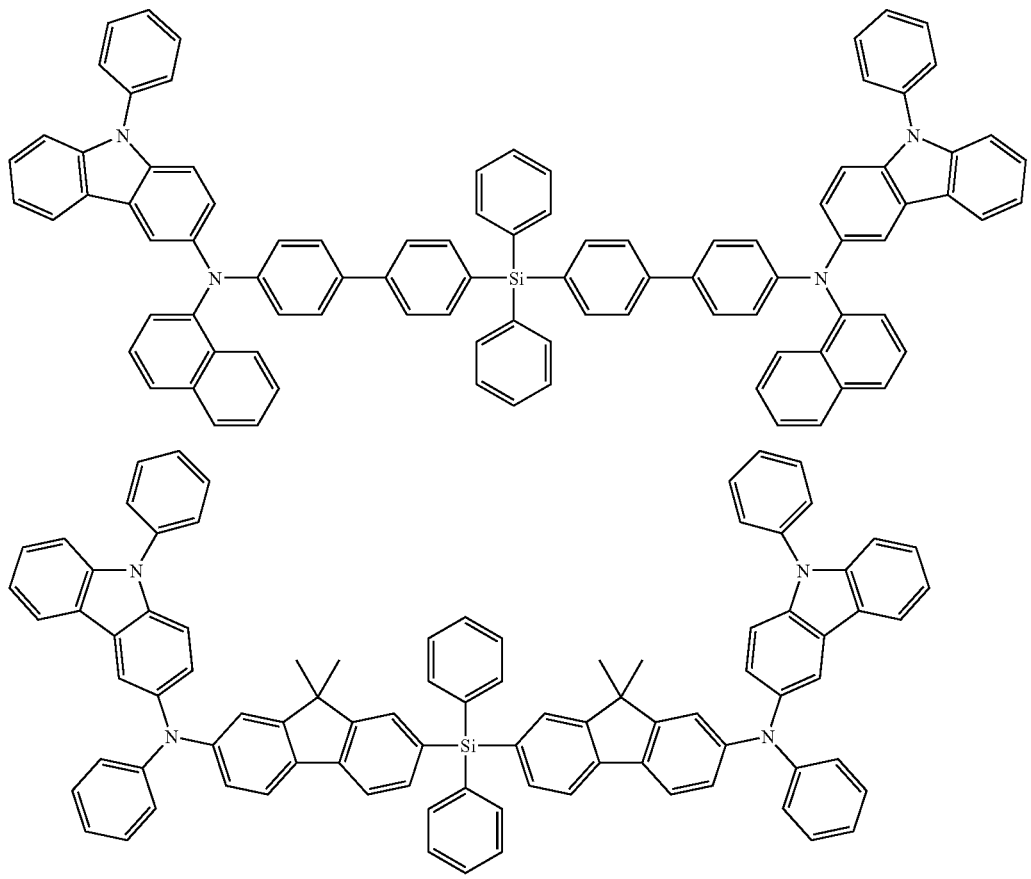

85

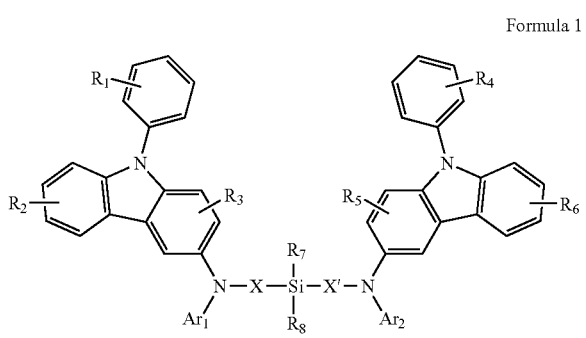

105

Some embodiments provide organic light emitting diode comprising: a first electrode; a second electrode; and an organic layer interposed between the first electrode and the second electrode, wherein the organic layer comprises a silanylamine-based compound of Formula 1.

In some embodiments, the organic layer comprises at least one of a hole injection layer and a hole transport layer. In some embodiments, the organic layer comprises a single layer having both hole injecting and hole transporting properties.

In some embodiments, the organic layer comprises an emitting layer. In some embodiments, the emitting layer comprises a phosphorescent or fluorescent dopant and a host comprising the silanylamine-based compound.

In some embodiments, the structure of the light emitting diode comprises at least one of a first electrode/hole injection layer/emitting layer/second electrode structure, a first electrode/hole injection layer/hole transport layer/emitting layer/electron transport layer/second electrode structure, and a first electrode/hole injection layer/hole transport layer/emitting layer/electron transport layer/electron injection layer/second electrode structure.

Some embodiments further comprise at least one of a hole blocking layer and an electron blocking layer.

BRIEF DESCRIPTION OF THE DRAWINGS

The above and other features and advantages will become more apparent by describing in detail exemplary embodiments thereof with reference to the attached drawing in which.

DETAILED DESCRIPTION OF CERTAIN EMBODIMENTS

Figure 1:
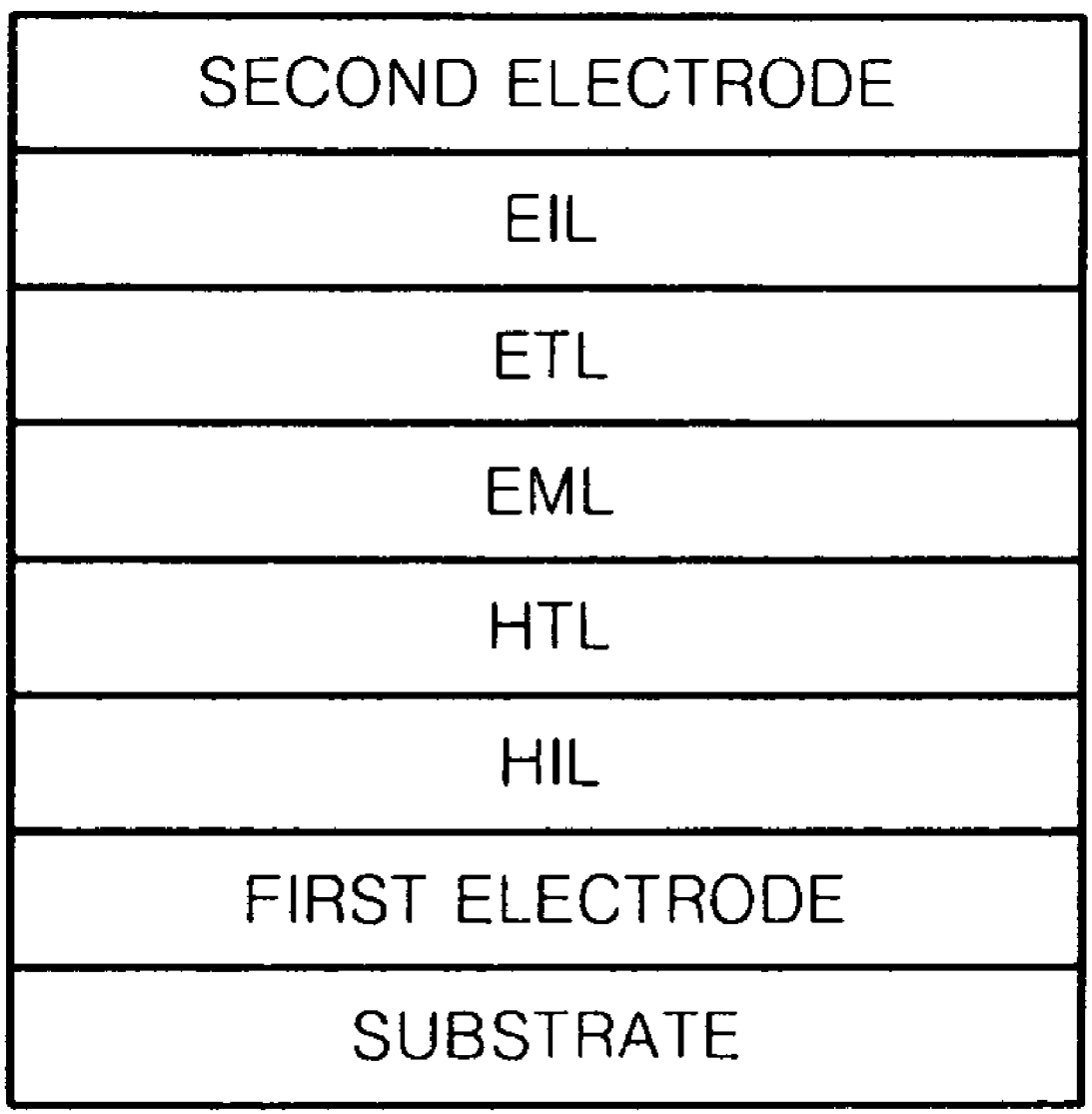
FIG. 1 is a diagram illustrating a structure of an embodiment an organic light emitting diode according to an embodiment.

Certain embodiments will now be described in detail with reference to the accompanying drawing, in which preferred embodiments are shown.

Some embodiments of a silanylamine-based compound are represented by Formula 1 below:

Formula 1 wherein $R_1$, $R_2$, $R_3$, $R_4$, $R_5$, $R_6$, $R_7$, and $R_8$ are each independently a hydrogen atom, a substituted or unsubstituted $C_1$-$C_{10}$ alkyl group, a substituted or unsubstituted $C_1$-$C_{10}$ alkoxy group, a fluorine atom, a cyano group, or an amine group, wherein adjacent groups among $R_1$, $R_2$, $R_3$, $R_4$, $R_5$, $R_6$, $R_7$, and $R_8$ may be bonded with one another to form a saturated or unsaturated carbon ring, $Ar_1$ and $Ar_2$ are each independently a substituted or unsubstituted $C_6$-$C_{20}$ aryl group, a substituted or unsubstituted $C_6$-$C_{20}$ aryloxy group, a substituted or unsubstituted $C_4$-$C_{20}$ heteroaryl group, or a substituted or unsubstituted $C_4$-$C_{20}$ condensed polycyclic group.

X and X' are each independently a substituted or unsubstituted $C_6$-$C_{20}$ aryl group or a substituted or unsubstituted $C_4$-$C_{20}$ condensed polycyclic group.

In some embodiments in which one of the above-defined $R_1$, $R_2$, $R_3$, $R_4$, $R_5$, $R_6$, $R_7$, $R_8$, $Ar_1$, $Ar_2$, X, and X' is an aryl group having 21 carbon atoms or more, or a condensed polycyclic group, deposition may not be easy due to a high molecular weight thereof.

The silanylamine-based compound of Formula 1 may function as a hole injection material, a hole transport material, and/or an emitting material. In addition, since the silanylamine-based compound of Formula 1 has a rigid tricyclic structure at the center, it has a high glass transition temperature ($T_g$) and/or a high melting point. Thus, the silanylamine-based compound has excellent thermal resistance against Joule heat generated within organic layers, between organic layers, or between an organic layer and a metal layer, and has high durability at a high temperature. An organic light emitting diode fabricated using the silanylamine-based compound has high durability while stored or operated.

$R_1$, $R_2$, $R_3$, $R_4$, $R_5$, $R_6$, $R_7$, and $R_8$ are each independently a hydrogen atom, a substituted or unsubstituted $C_1$-$C_{10}$ alkyl group, a substituted or unsubstituted $C_1$-$C_{10}$ alkoxy group, a fluorine atom, a cyano group or an amine group, wherein adjacent groups among $R_1$, $R_2$, $R_3$, $R_4$, $R_5$, $R_6$, $R_7$, and $R_8$ may be bonded with one another to form a saturated or unsaturated carbon ring.

$R_1$, $R_2$, $R_3$, $R_4$, $R_5$, $R_6$, $R_7$, and $R_8$ may be each independently a hydrogen atom, a methyl group, an ethyl group, a fluoro group, a cyano group, an amino group, a phenyl group, a naphthyl group, or the like.

In some embodiments, X may be one of the groups represented by formulae below.

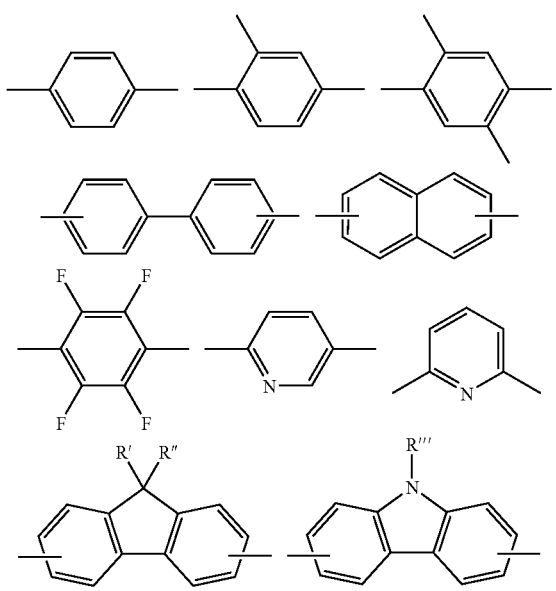

Here, R', R" and R'" may each be independently a hydrogen atom, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_6$-$C_{10}$ aryloxy group, a substituted or unsubstituted $C_6$-$C_{10}$ aryl group, a substituted or unsubstituted $C_4$-$C_{10}$ heteroaryl group, or a substituted or unsubstituted $C_4$-$C_{10}$ condensed polycyclic group.

In some embodiments, X may be one of the groups represented by formulae below.

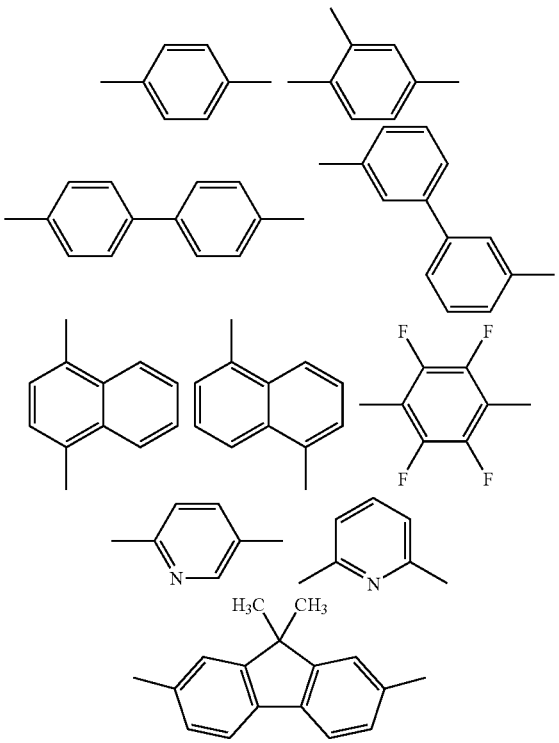

$Ar_1$ and $Ar_2$ may be each independently a substituted or unsubstituted $C_6$-$C_{20}$ aryl group or a substituted or unsubstituted $C_4$-$C_{20}$ heteroaryl group.

In some embodiments, $Ar_1$ and $Ar_2$ may each be independently a phenyl group, a $C_1$-$C_5$ alkylphenyl group, a $C_1$-$C_5$ alkoxyphenyl group, a cyanophenyl group, a phenoxyphenyl group, a fluorophenyl group, a naphthyl group, a $C_1$-$C_5$ alkylnaphthyl group, a $C_1$-$C_5$ alkoxynaphthyl group, a cyanonaphthyl group, a halonaphthyl group, a fluorenyl group, a carbazolyl group, a $C_1$-$C_5$ alkyl carbazolyl group, a biphenyl group, a $C_1$-$C_5$ alkyl biphenyl group, a $C_1$-$C_5$ alkoxy biphenyl group, or a pyridyl group.

Preferably, $Ar_1$ and $Ar_2$ may each be independently a phenyl group, an ethylphenyl group, an ethylbiphenyl group, an o-, m-, or p-fluorophenyl group, a dichlorophenyl group, a cyanophenyl group, a dicyanophenyl group, a trifluorophenyl group, a methoxyphenyl group, an o-, m-, or p-tolyl group, a mesithyl group, a phenoxyphenyl group, a (α,α-dimethyl benzene)phenyl group, a (N,N'-dimethyl)aminophenyl group, a (N,N'-diphenyl)aminophenyl group, a pentalenyl group, a naphthyl group, a methylnaphthyl group, an athracenyl group, an azulenyl group, a heptalenyl group, an acenaphthylenyl group, a fluorenyl group, an anthraquinolyl group, a phenanthryl group, a triphenylene group, a pentaphenyl group, a hexaphenyl group or a carbazolyl group.

More preferably, $Ar_1$ and $Ar_2$ may each be independently a monocyclic to tricyclic aryl group such as a fluorenyl group, a carbazolyl group, a phenyl group, a fluorophenyl group, a tolyl group, a naphthyl group, a biphenyl group, and a cyanophenyl group, or a monocyclic to tricyclic aryl group, wherein one to three substituents selected from the group consisting of a $C_1$-$C_4$ alkyl group, a $C_1$-$C_5$ alkoxy group, a cyano group, an amine group, a phenoxy group, a phenyl group, and a halogen atom are substituted to aromatic rings of the monocyclic to tricyclic aryl group.

Examples of suitable unsubstituted alkyl groups include a methyl group, an ethyl group, an isobutyl group, a sec-butyl group, a pentyl group, an iso-amyl group, and a hexyl group, wherein at least one hydrogen atom of the alkyl group may be substituted with a halogen atom, a hydroxyl group, a nitro group, a cyano group, an amino group, an amidino group, hydrazine, hydrazone, a carboxylic acid and salts thereof, a sulfonic acid and salts thereof, a phosphoric acid and salts thereof, a $C_1$-$C_{10}$ alkyl group, a $C_1$-$C_{10}$ alkenyl group, a $C_1$-$C_{10}$ alkynyl group, a $C_6$-C— aryl group, a $C_7$-$C_{20}$ arylalkyl group, a $C_4$-$C_{20}$ heteroaryl group, or a $C_4$-$C_{20}$ heteroarylalkyl group.

Examples of suitable unsubstituted alkoxy groups include a methoxy group, an ethoxy group, a phenyloxy group, a cyclohexyloxy group, a naphthyloxy group, an isopropyloxy group, and a diphenyloxy group, wherein at least one hydrogen atom of the alkoxy group may be substituted with the substituents described above with reference to the alkyl group.

The unsubstituted aryl group may be used alone or in combination, and is a carbocyclic aromatic system having one or more rings which may be bonded to each other or fused together. At least one hydrogen atom of the aryl group may be substituted with the substituents described above with reference to the alkyl group.

Examples of suitable unsubstituted aryloxy groups include a phenyloxy group, a naphthaleneoxy group, and a diphenyloxy group. At least one hydrogen atom of the aryloxy group may be substituted with the substituents described above with reference to the alkyl group.

The unsubstituted heteroaryl group is a monovalent monocyclic or bivalent bicyclic aromatic organic compound that includes 1, 2, or 3 hetero atoms selected from the group consisting of N, O, P, and S, and includes rings comprising 5 to 30 carbon atoms. At least one hydrogen atom of the heteroaryl group may be substituted with the substituents described with reference to the alkyl group.

Examples of suitable heteroaryl groups include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, and an indolyl group.

Some embodiments of the silanylamine-based compound of Formula 1 include Compounds 1 to 112 illustrated below, but are not limited thereto.

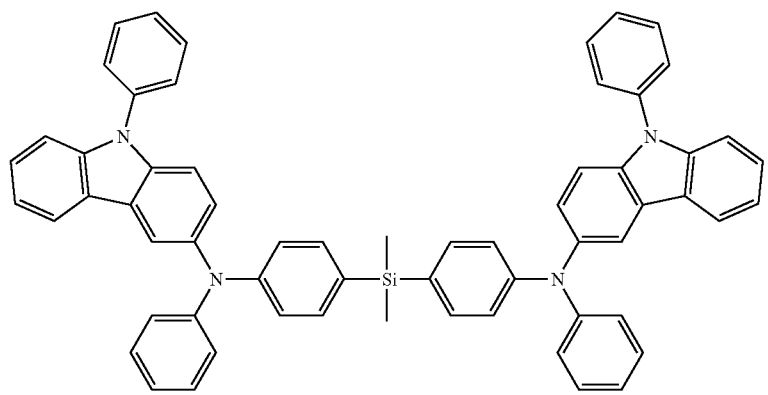

1

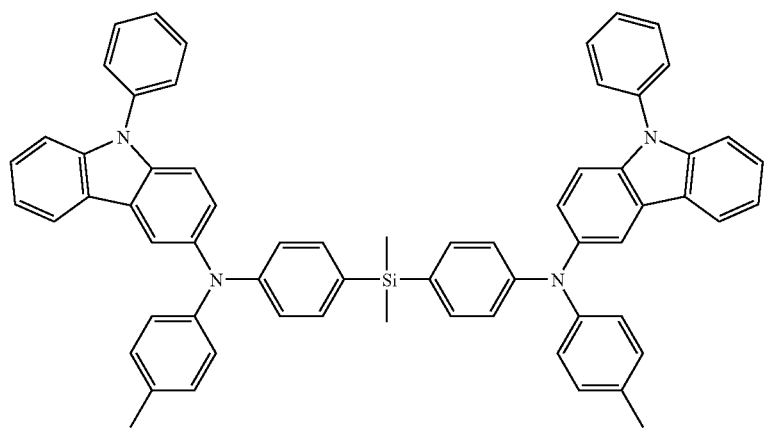

2

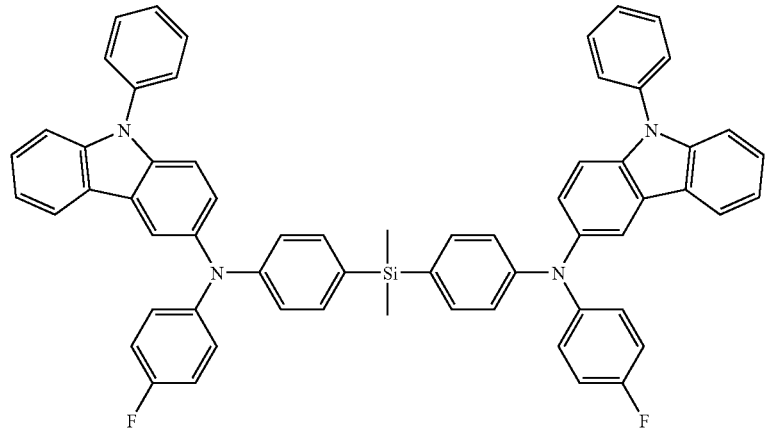
3
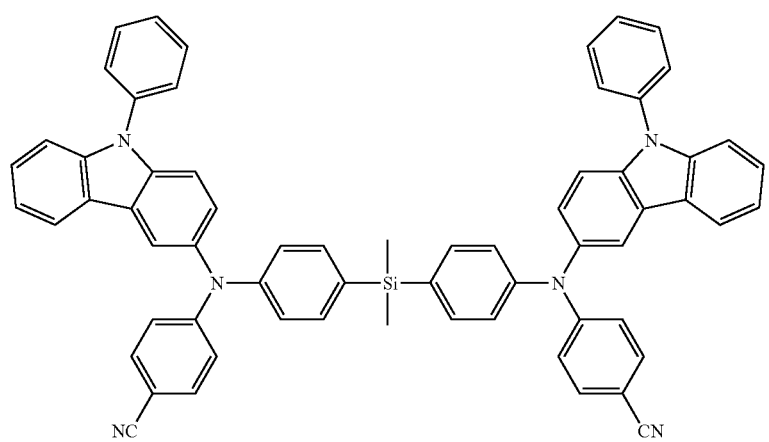
4
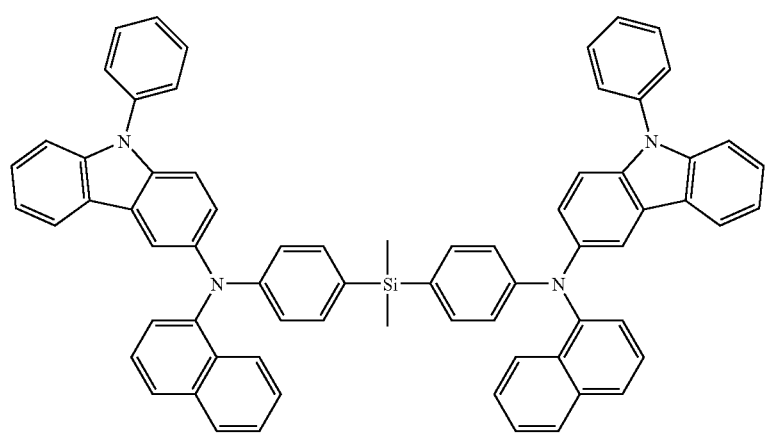
5

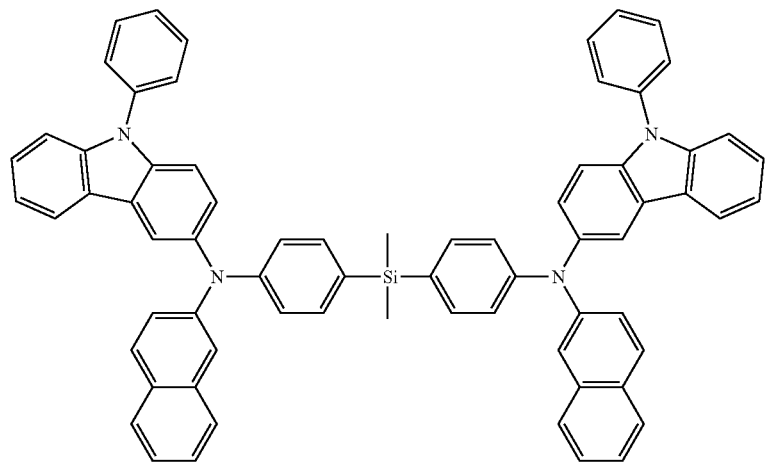
6
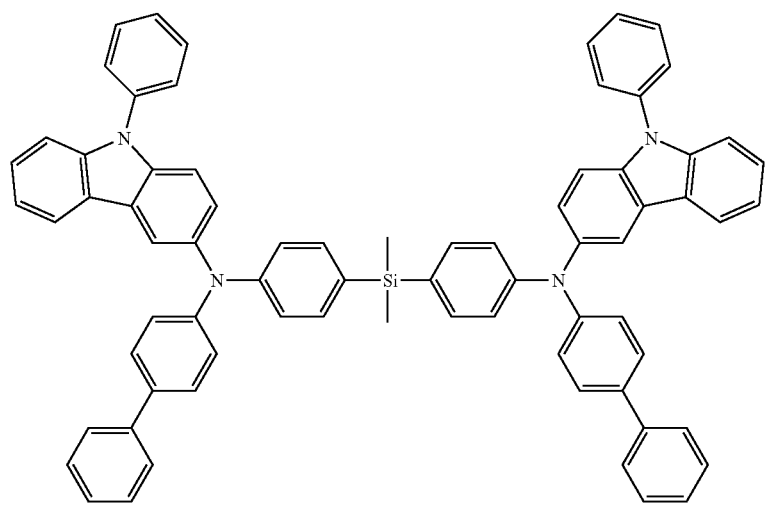
7
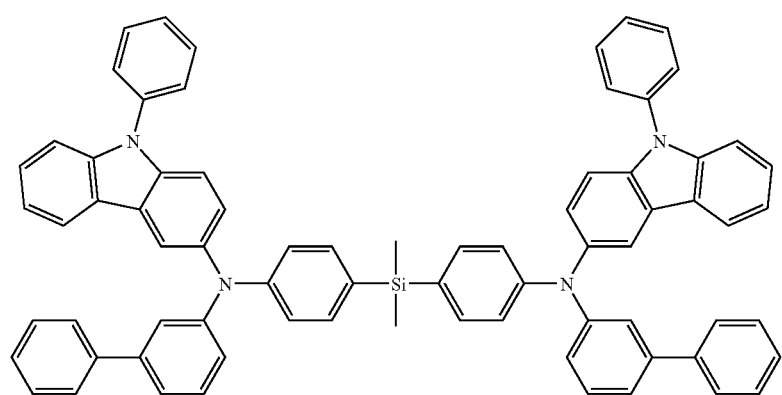
8

9
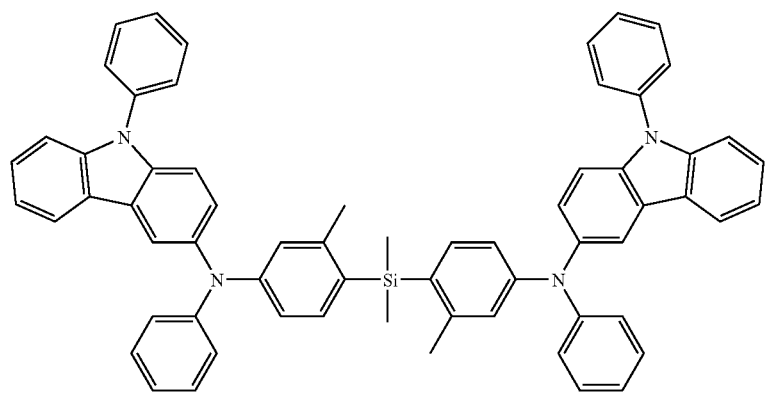
10
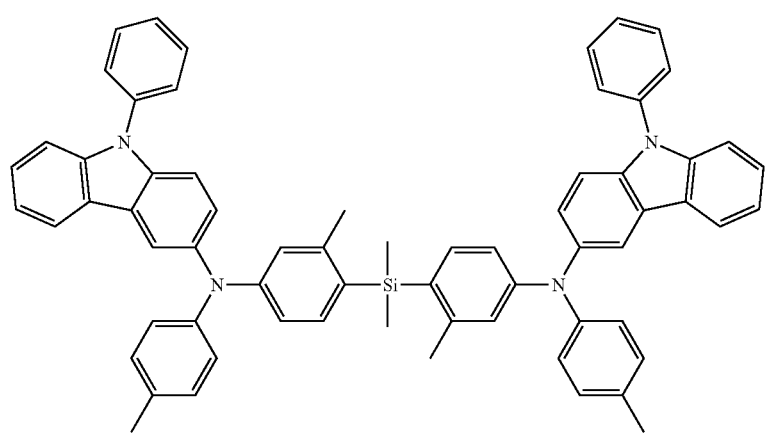
11
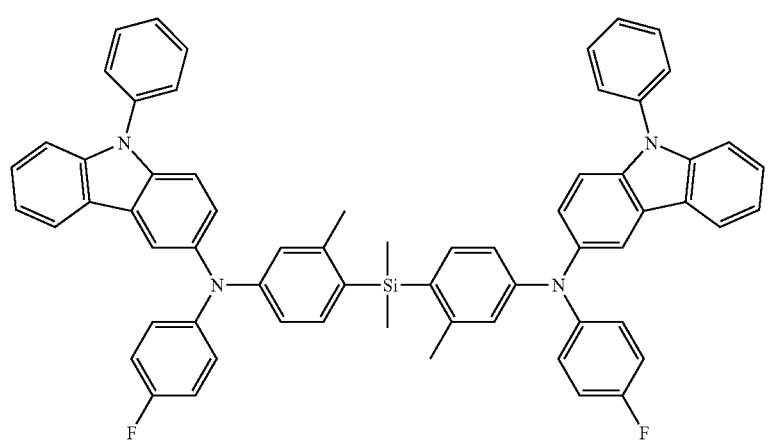

-continued
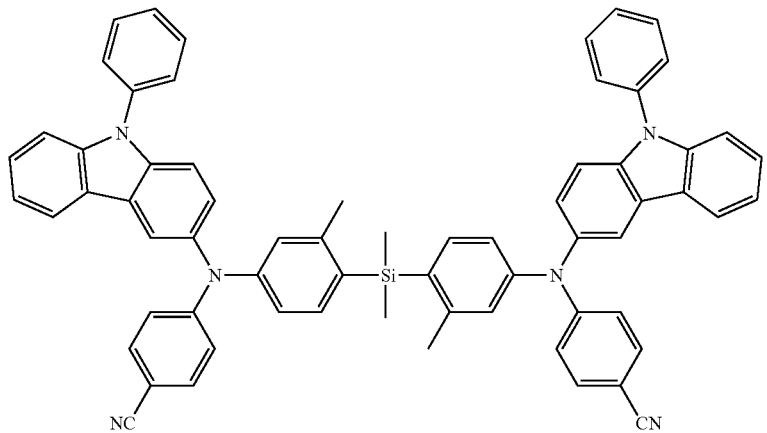
12
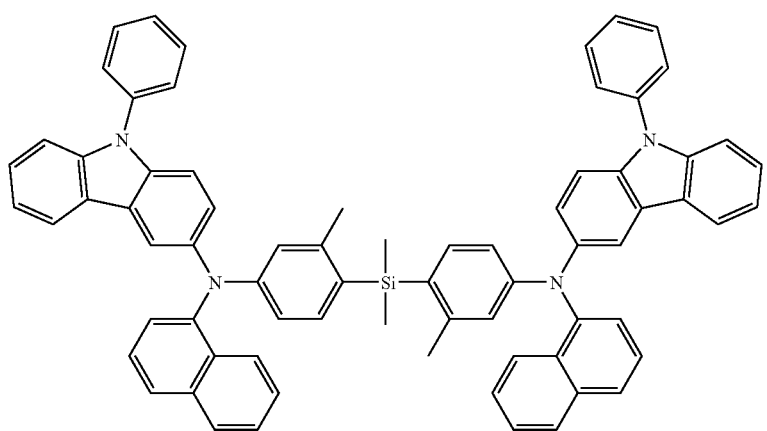
13
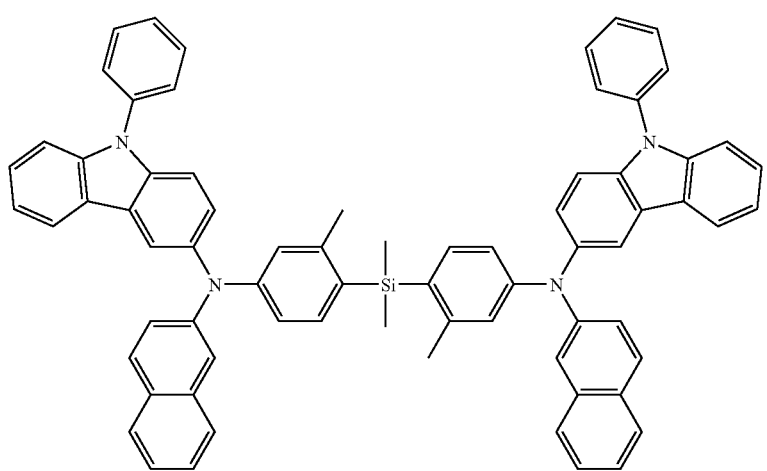
14

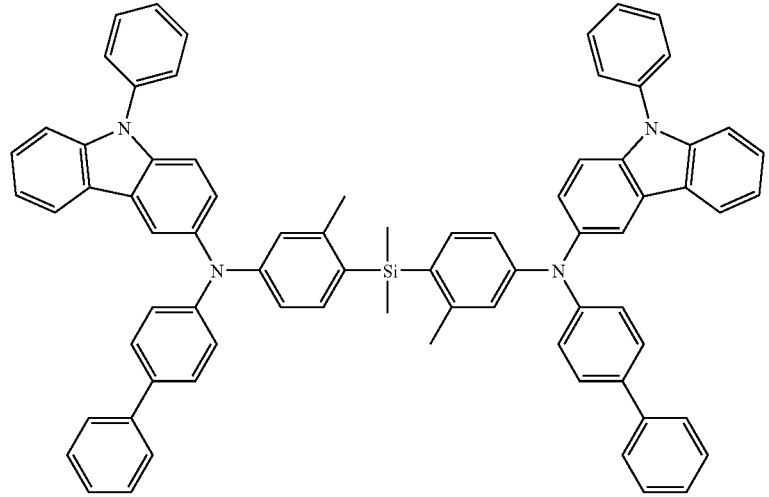
15
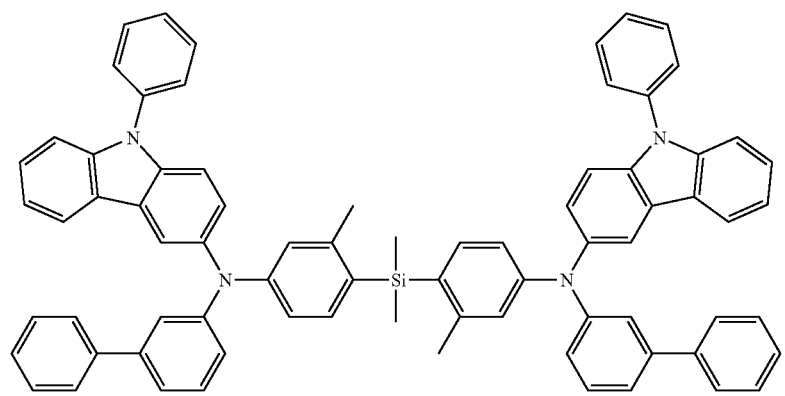
16
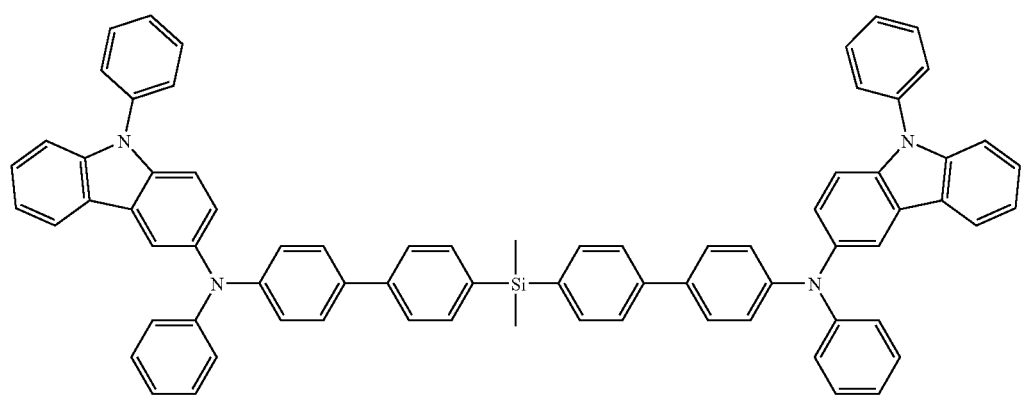
17

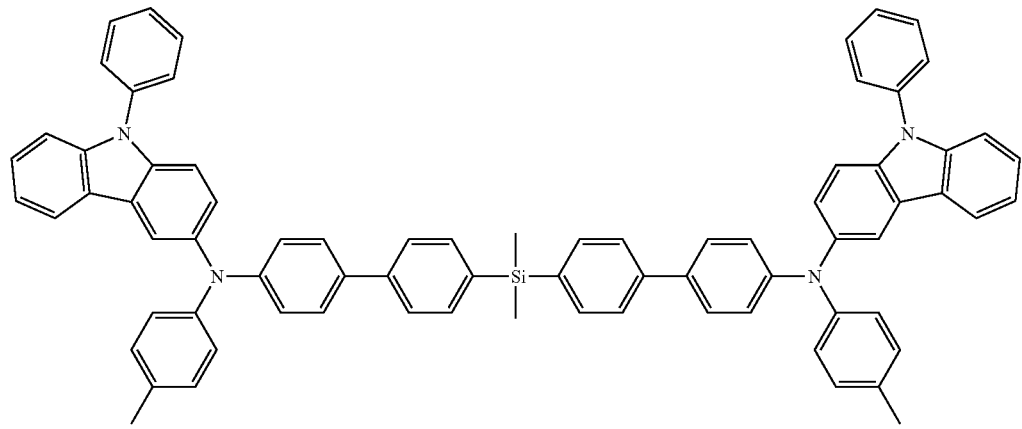
18
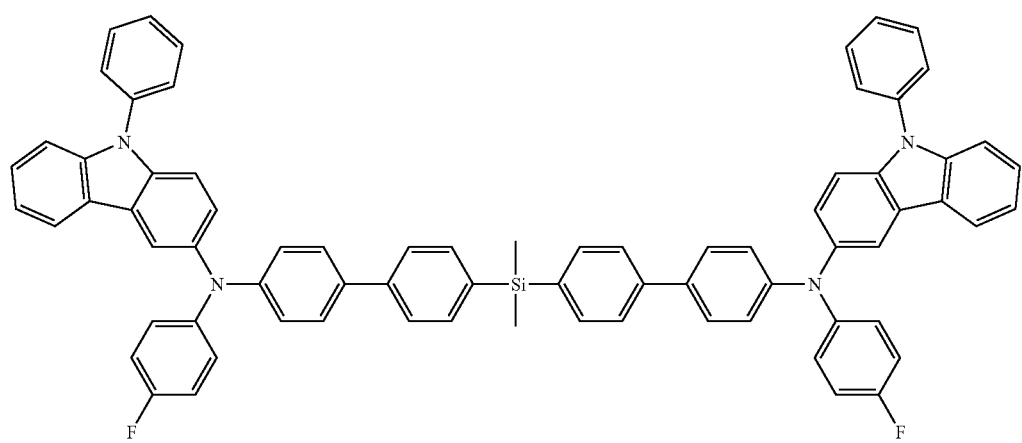
19
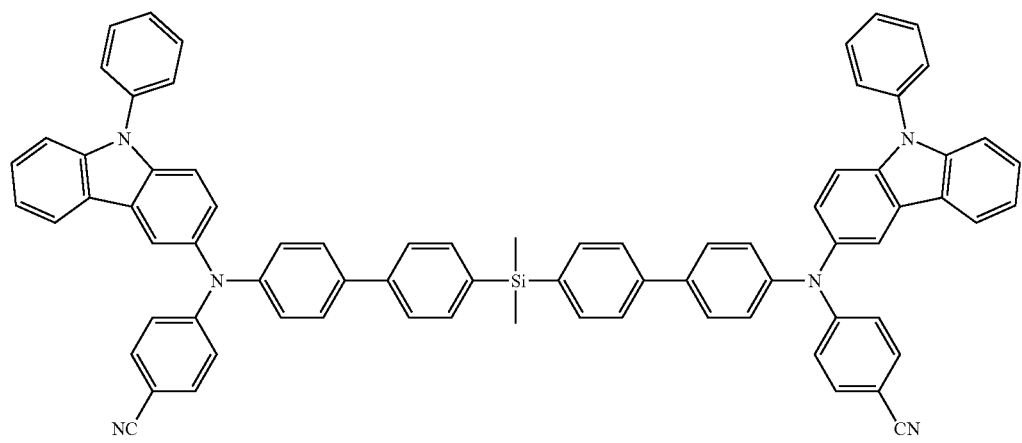
20

-continued
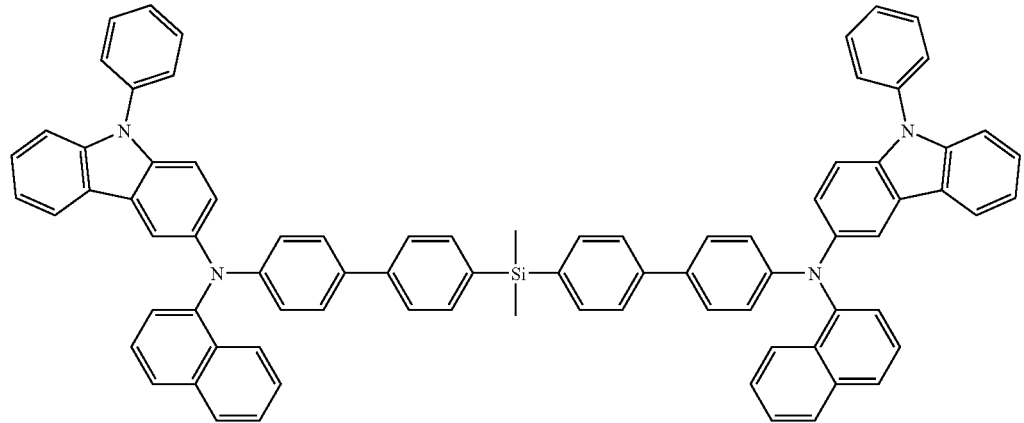
21
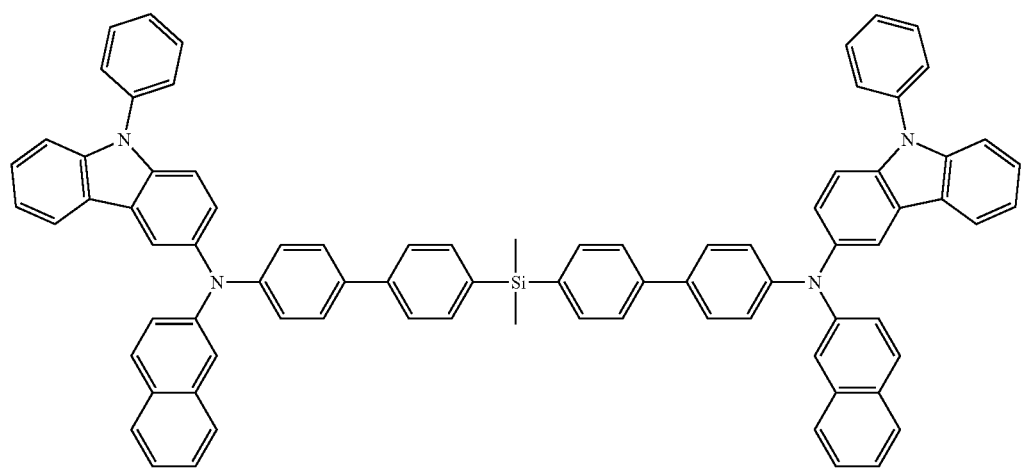
22
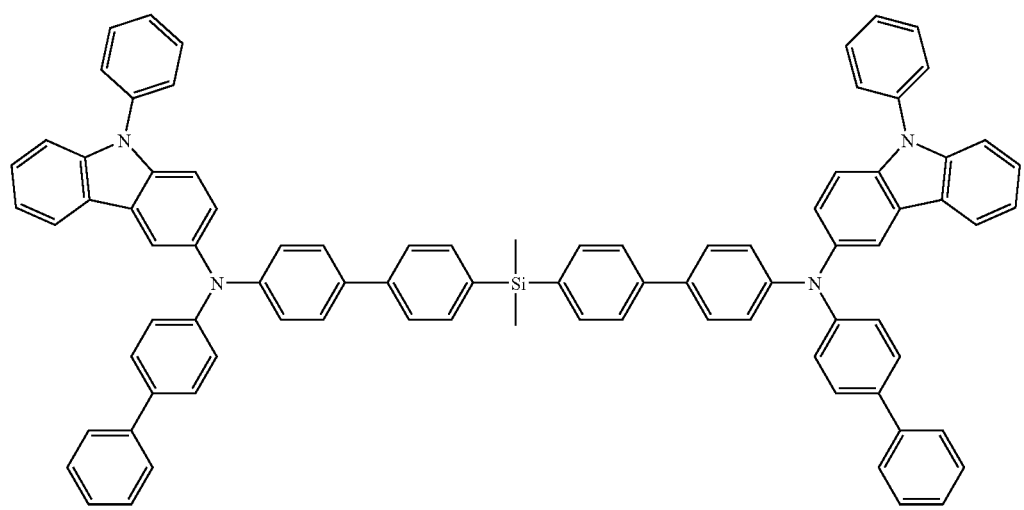
23

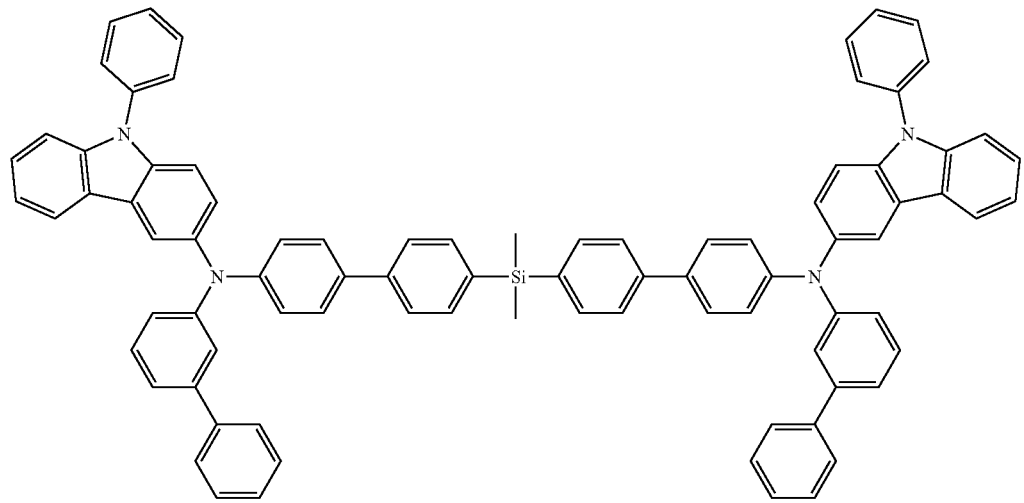
24
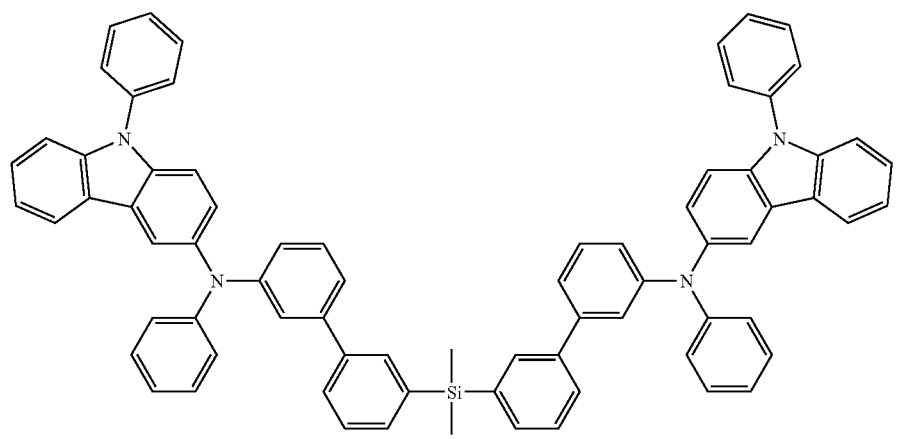
25
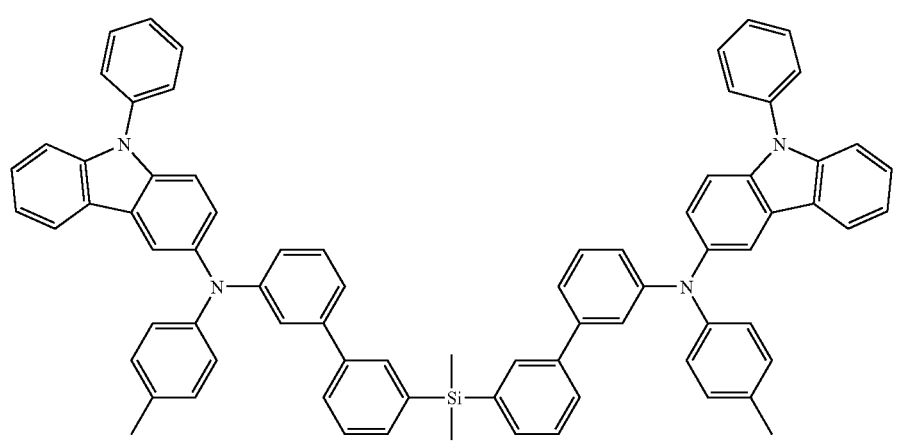
26

-continued
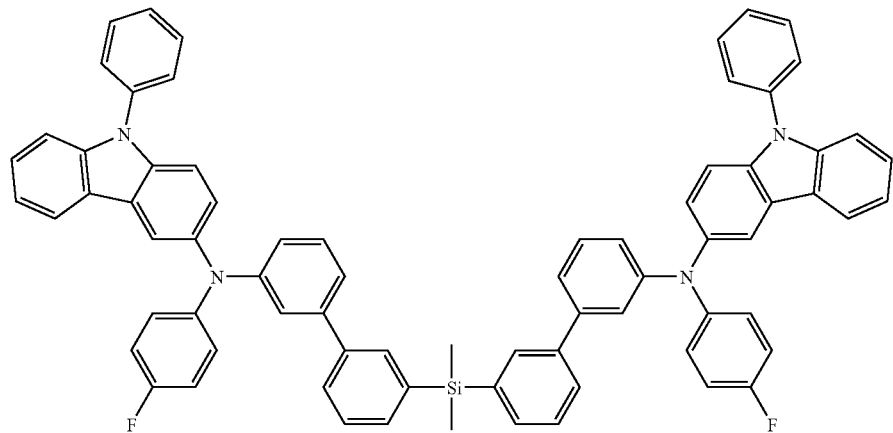
27
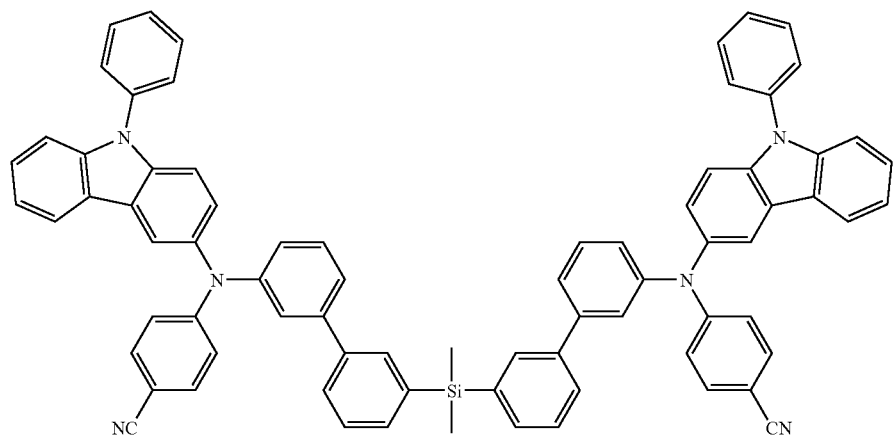
28
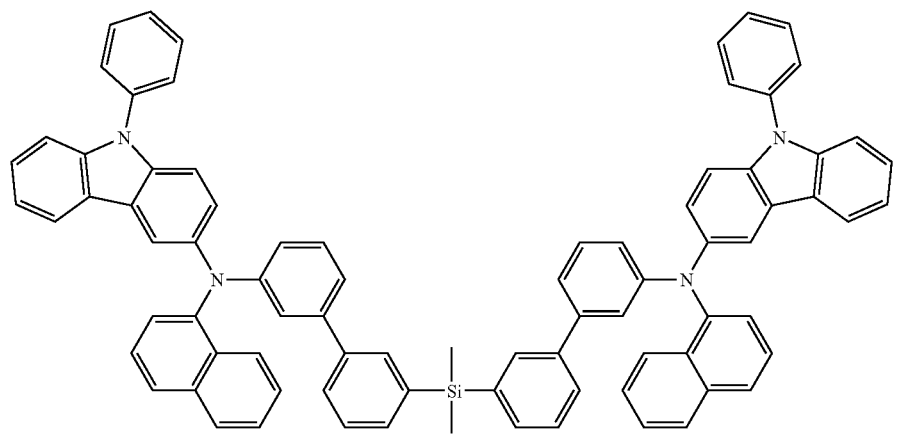
29

-continued
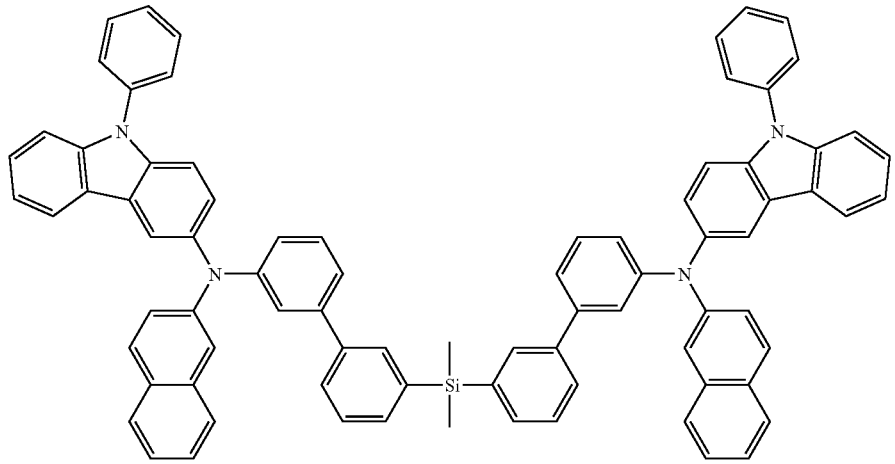
30
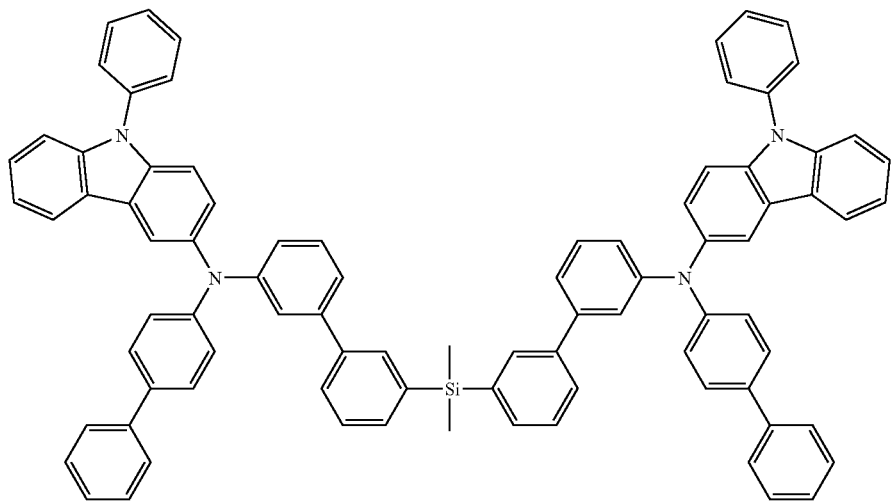
31
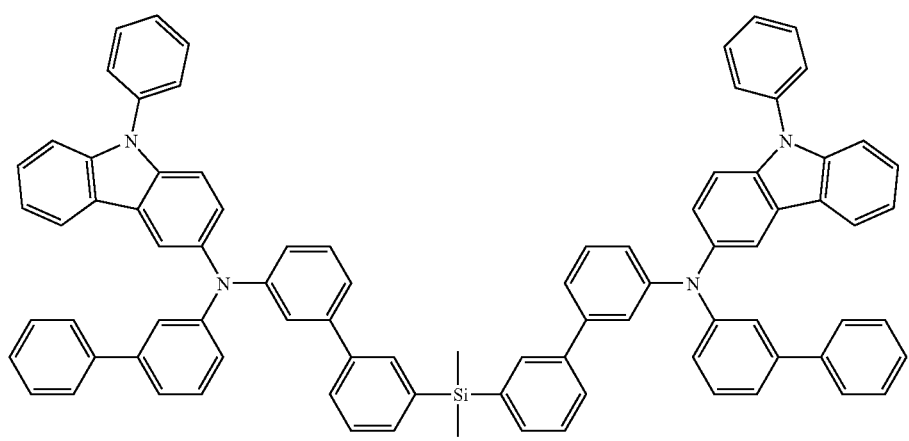
32

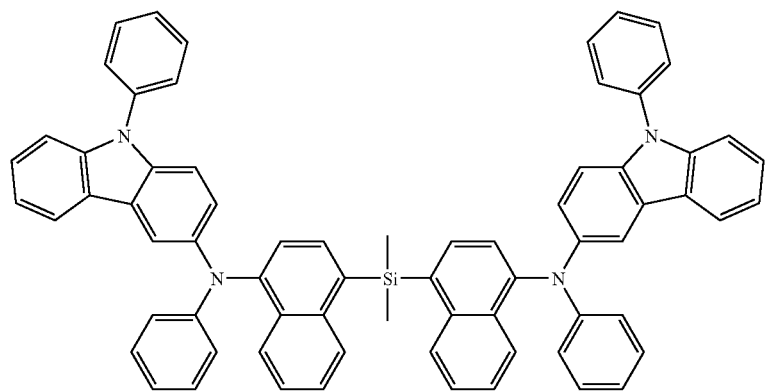
33
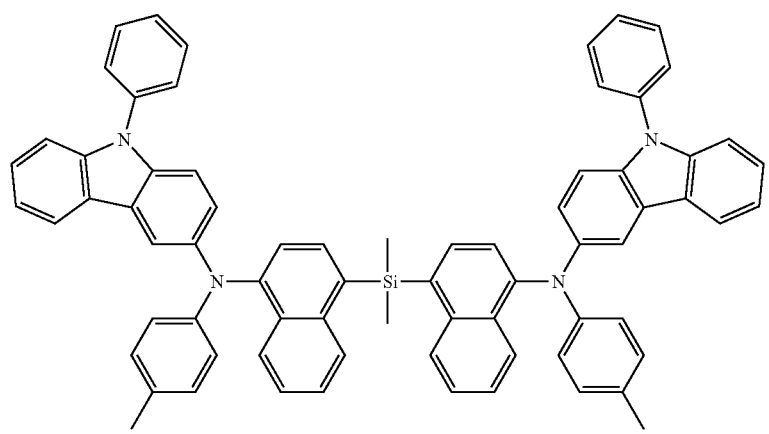
34
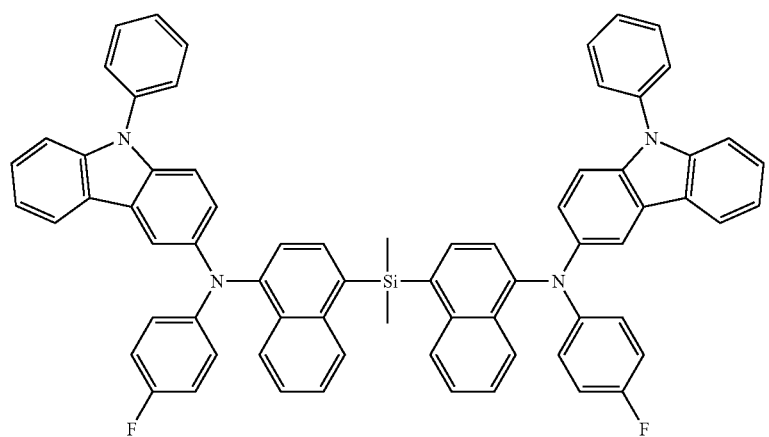
35

-continued
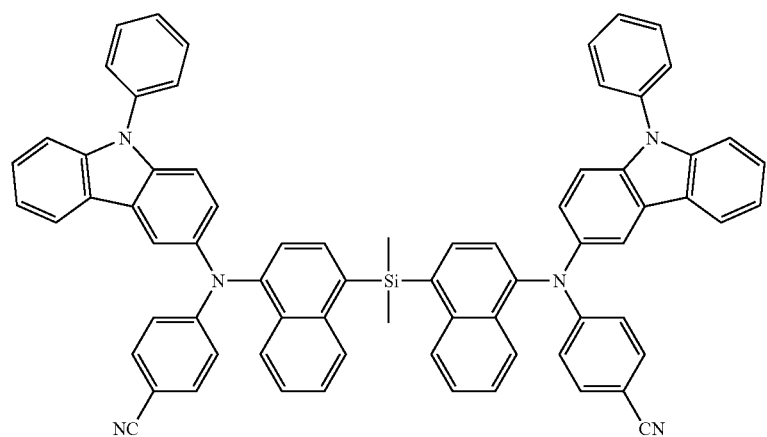
36
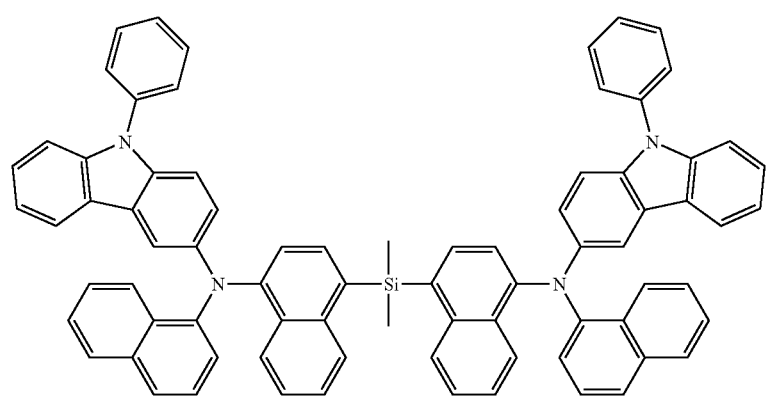
37
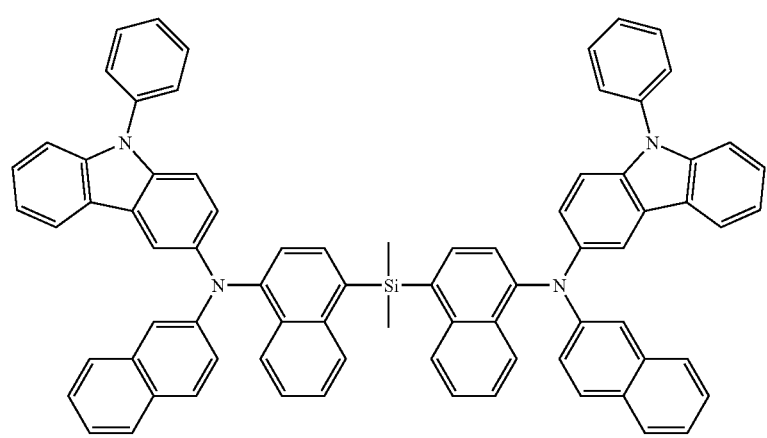
38

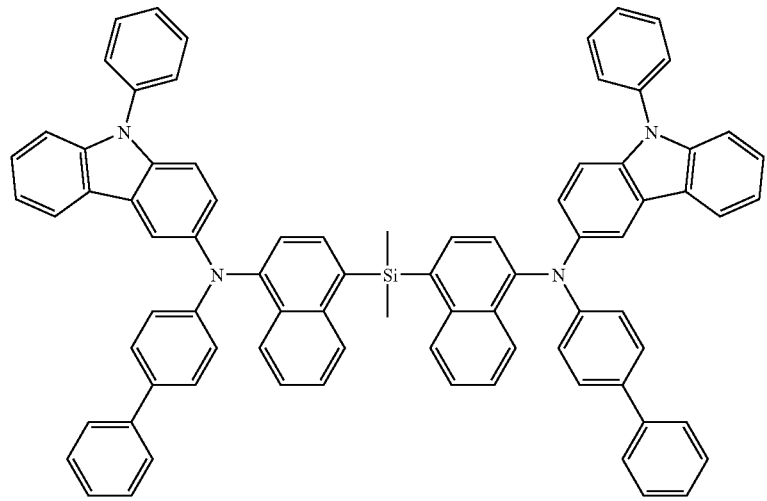
39
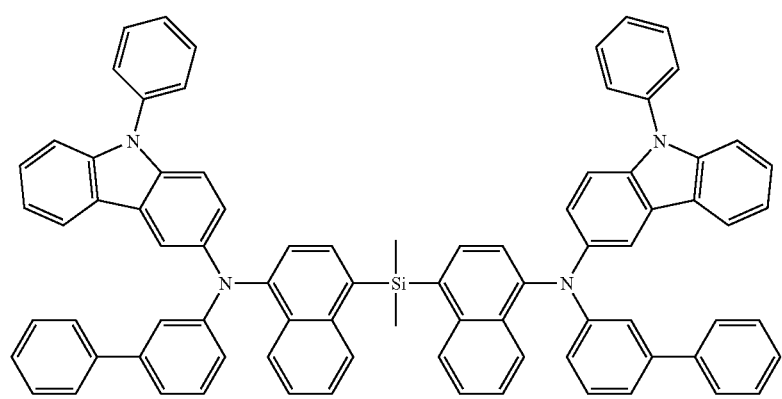
40
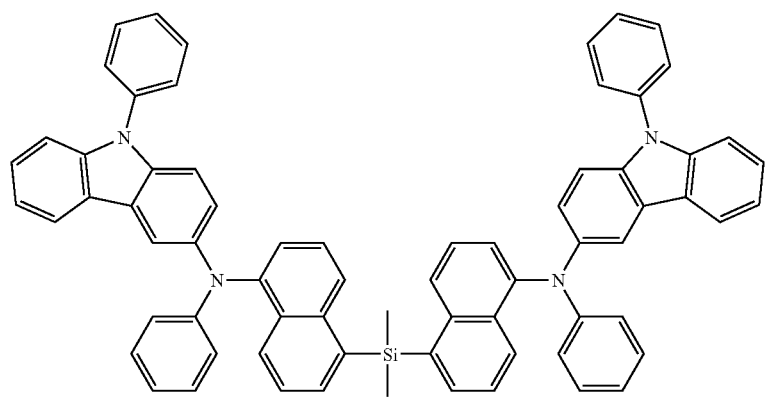
41

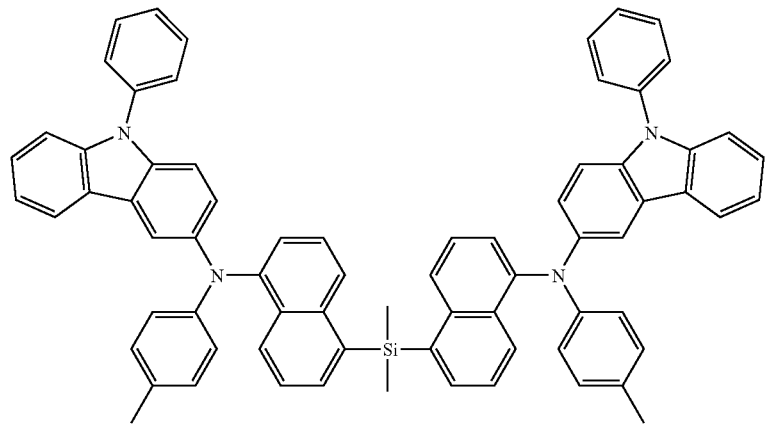
42
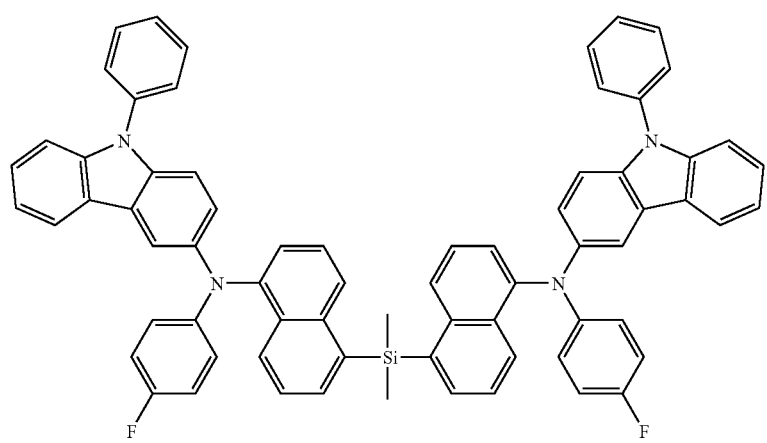
43
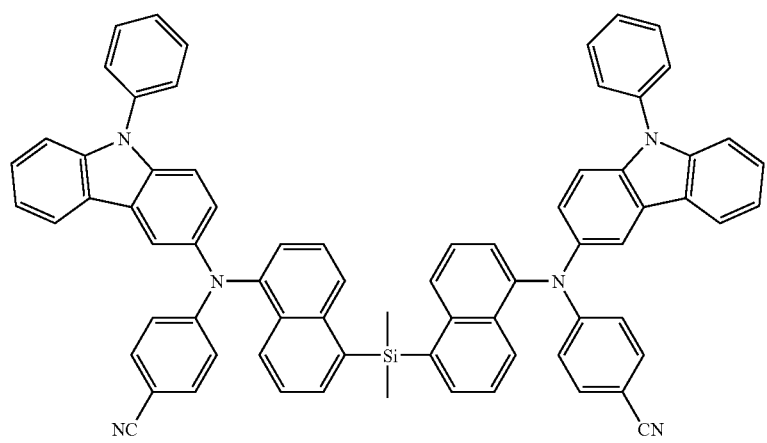
44

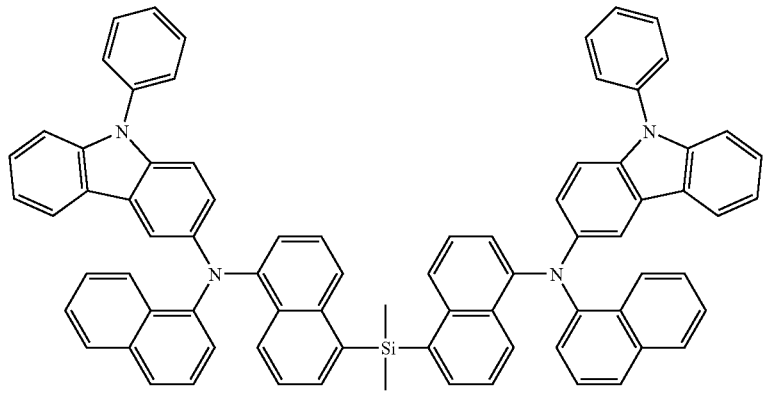
45
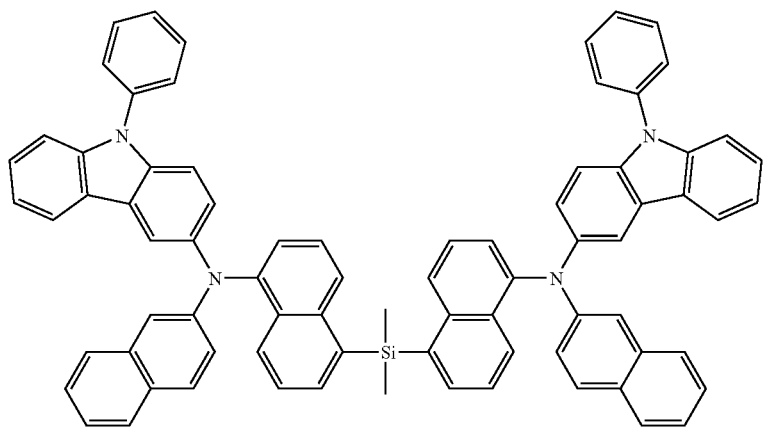
46
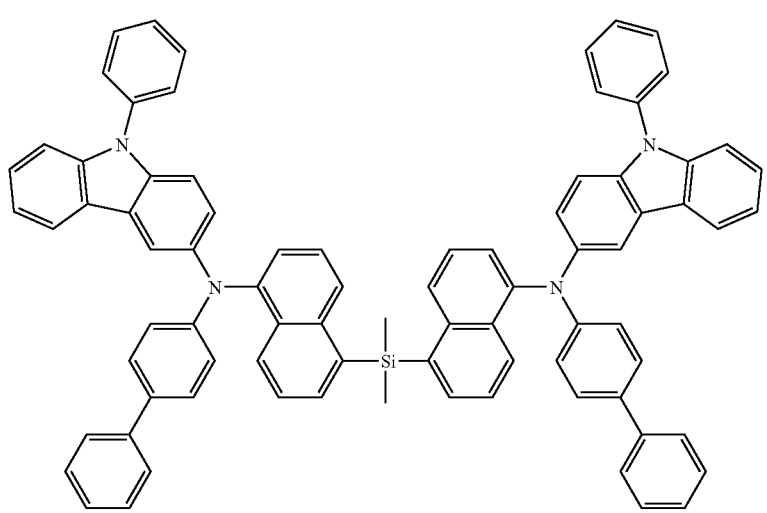
47

-continued
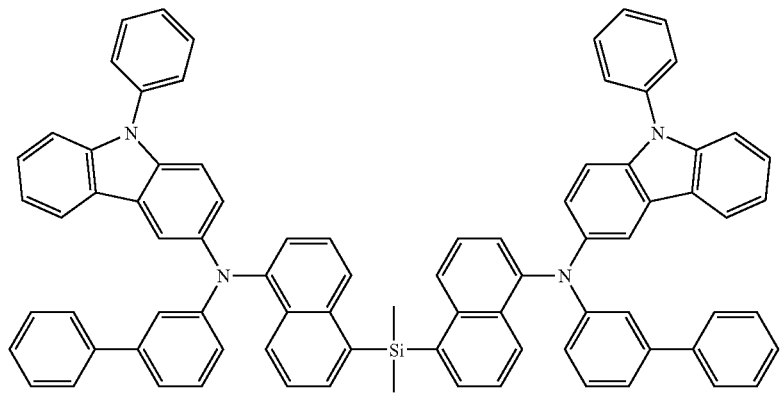
48
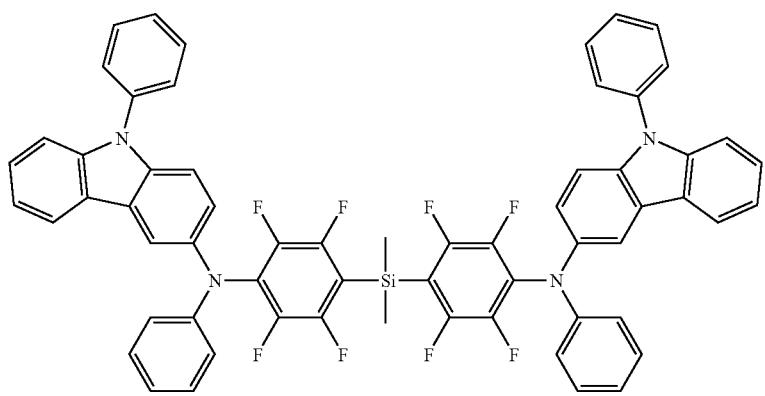
49
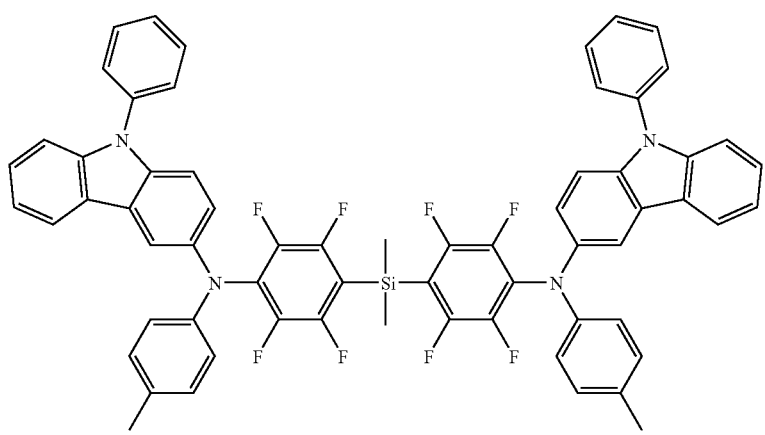
50
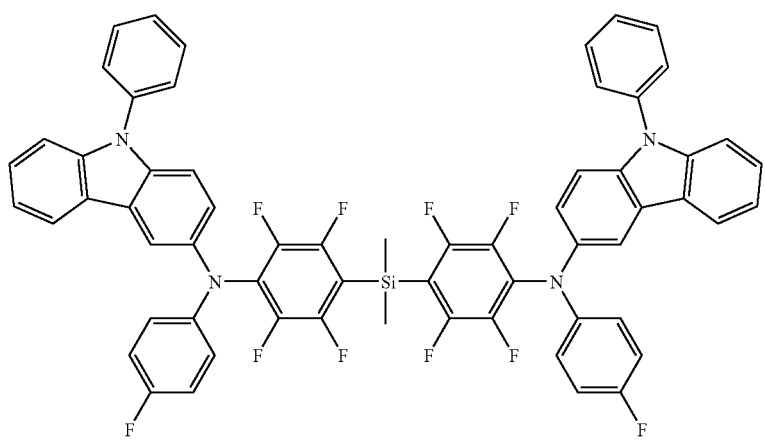
51

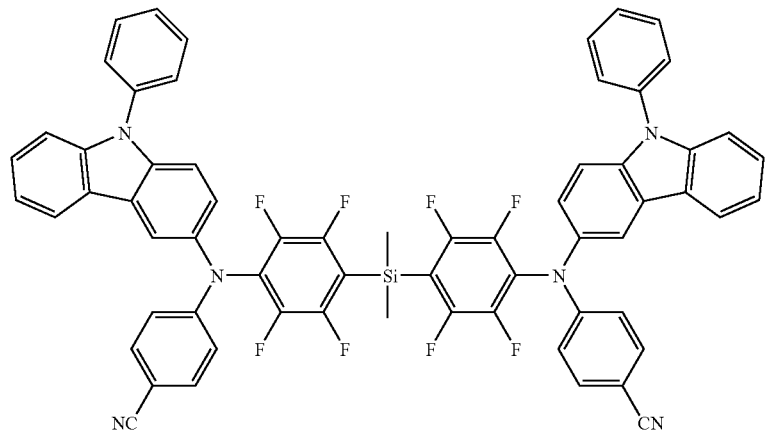
52
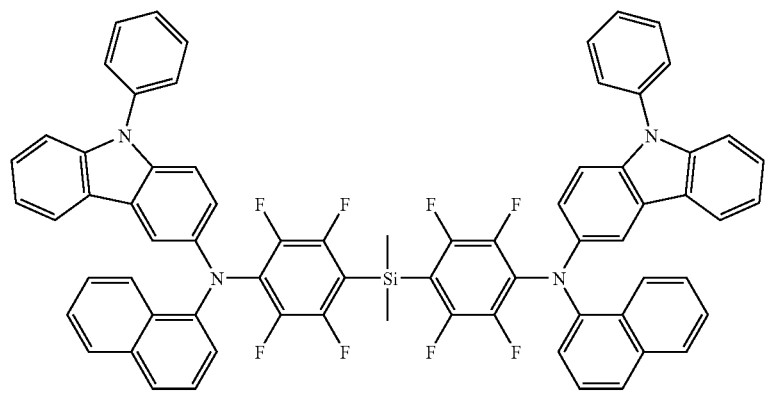
53
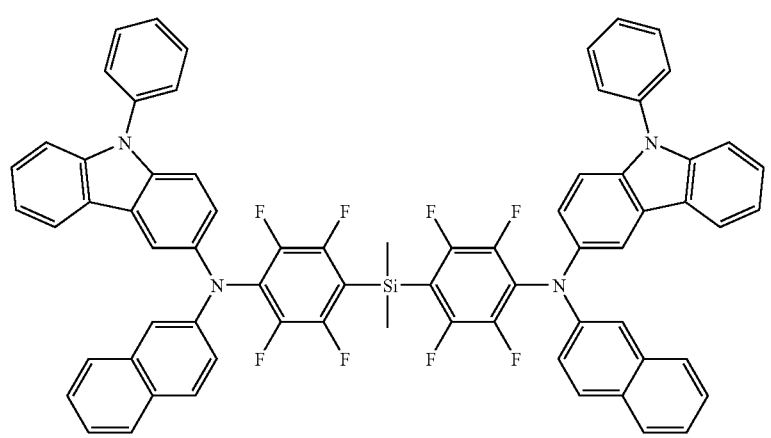
54

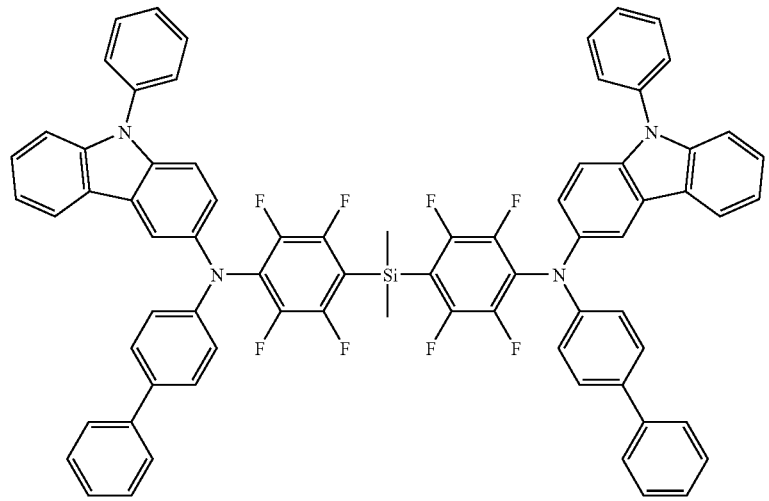
55
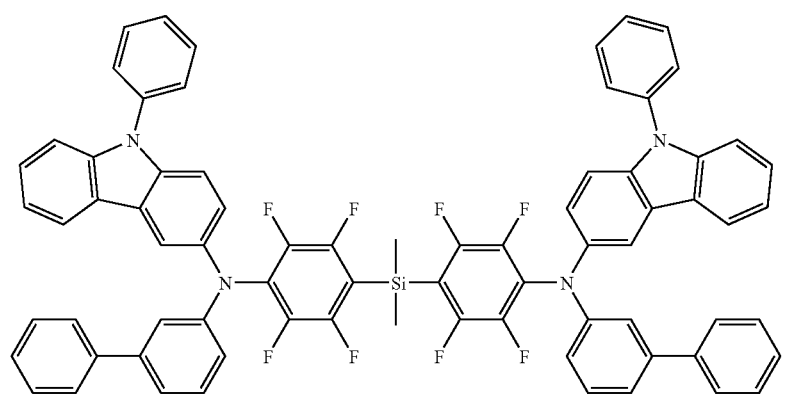
56
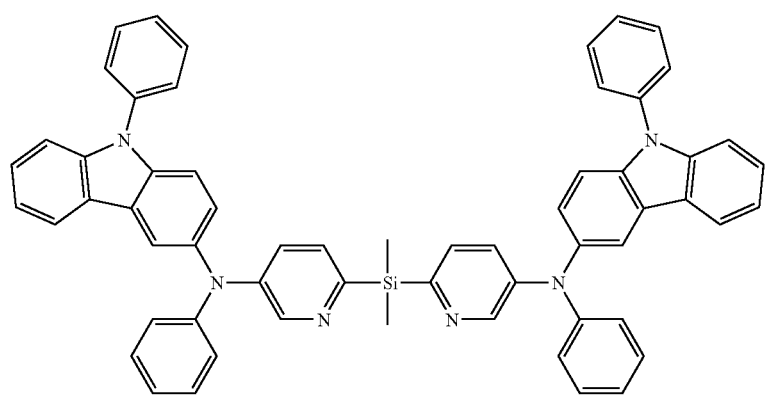
57

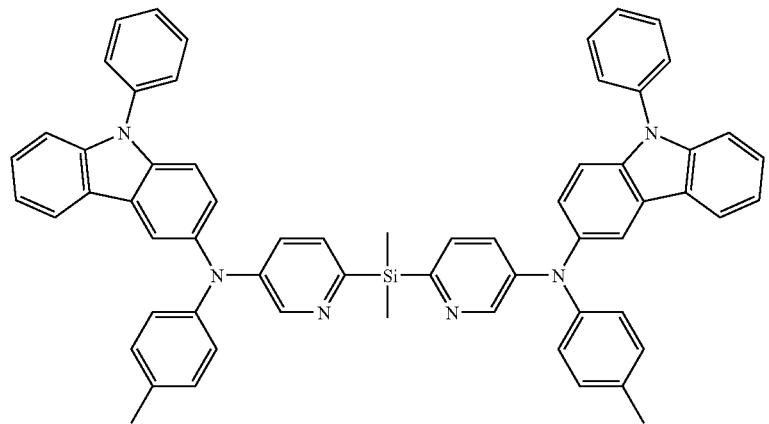
58
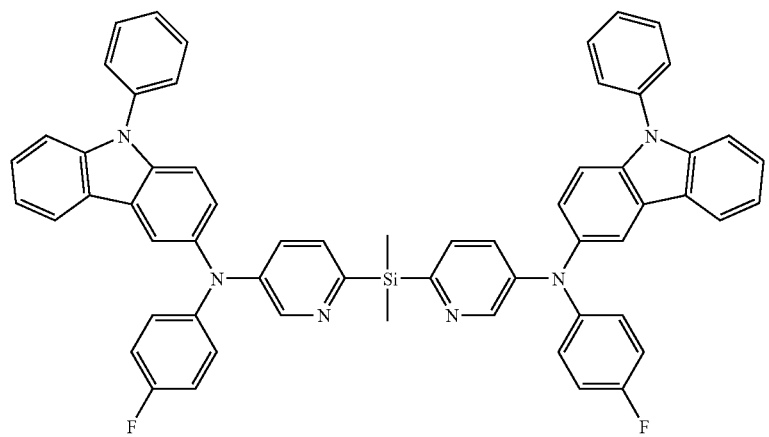
59
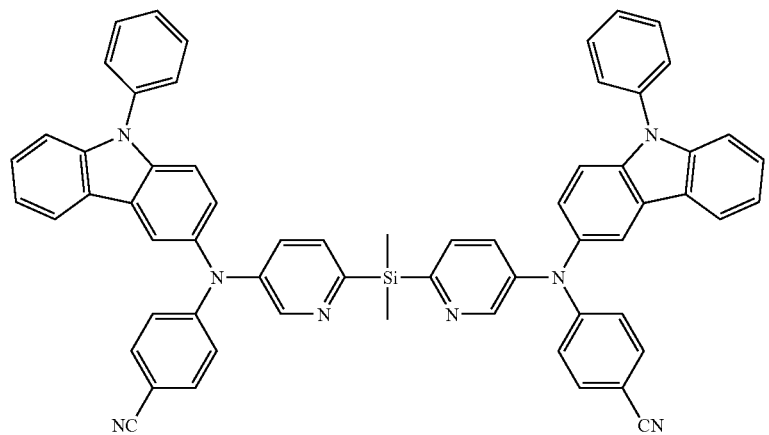
60

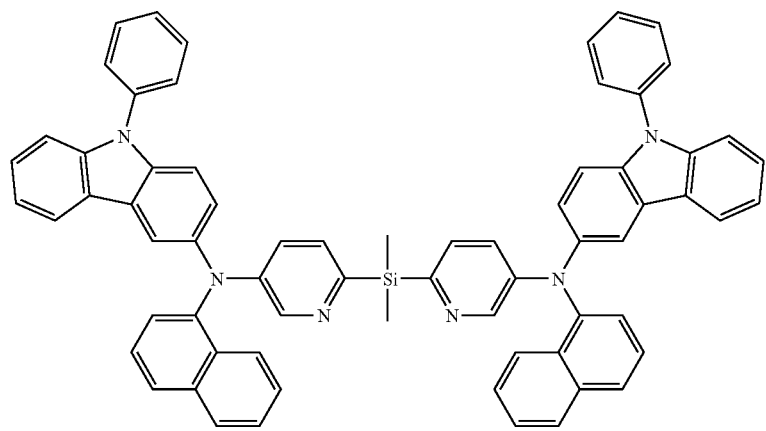
61
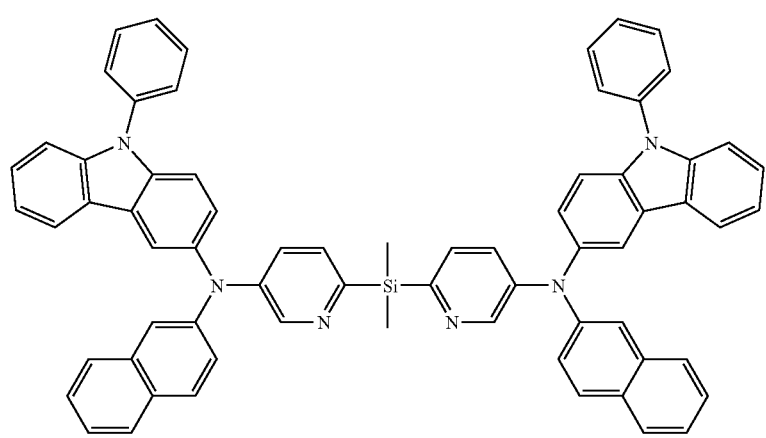
62
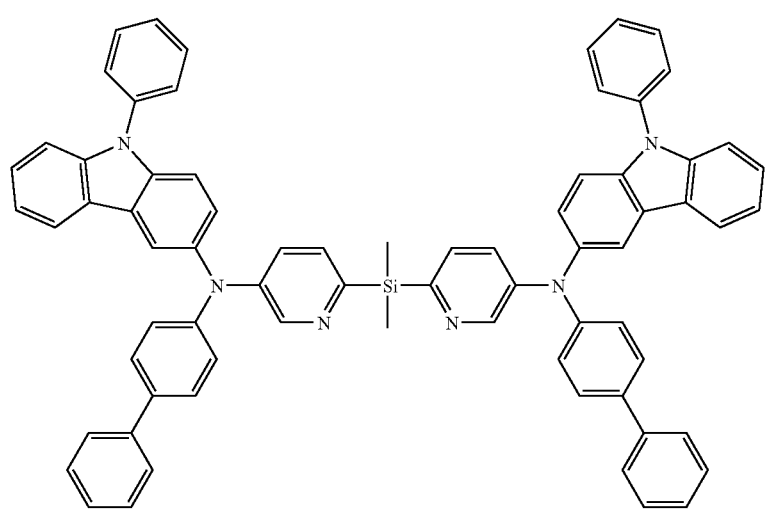
63

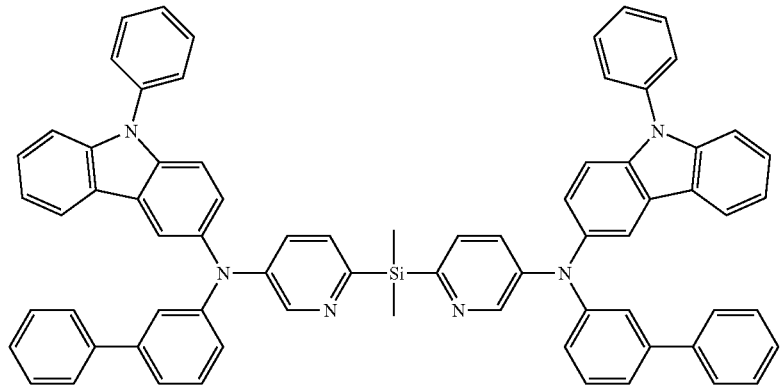
64
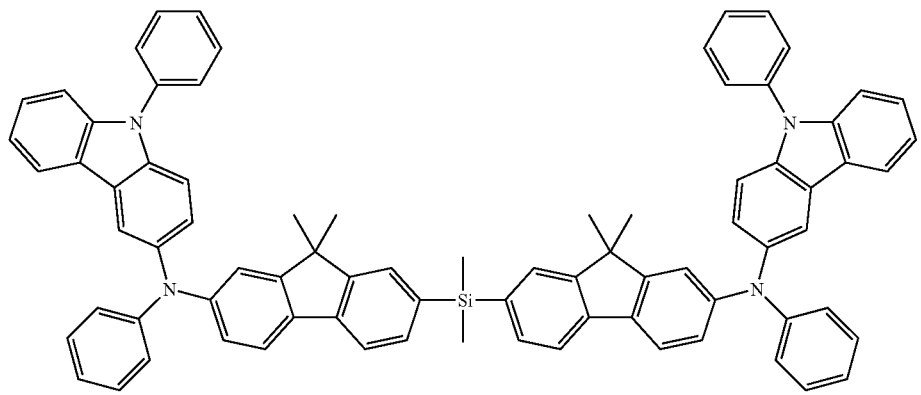
65
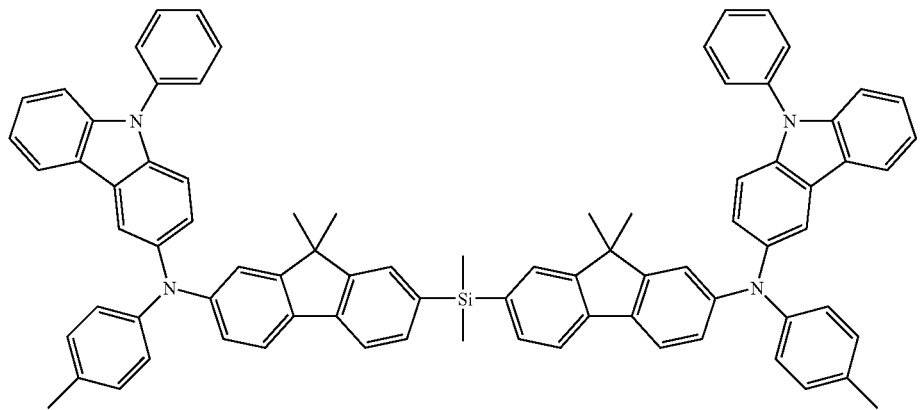
66
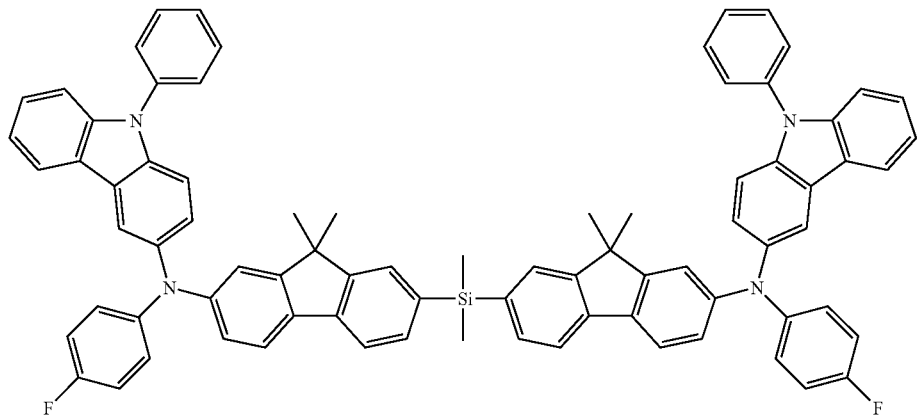
67

-continued
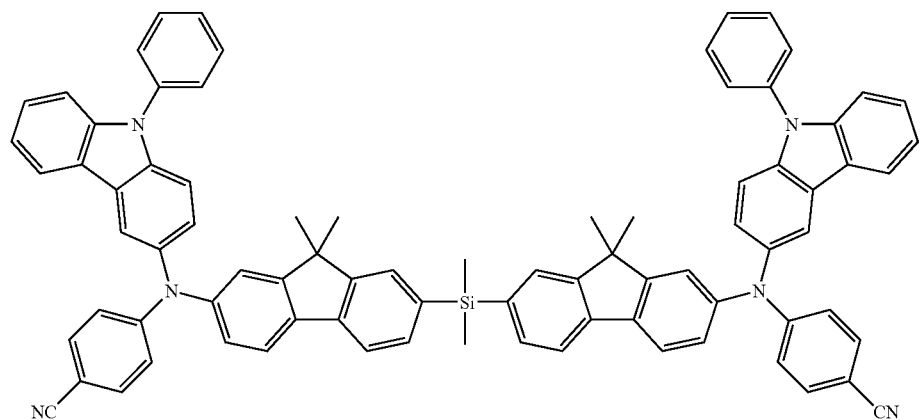
68
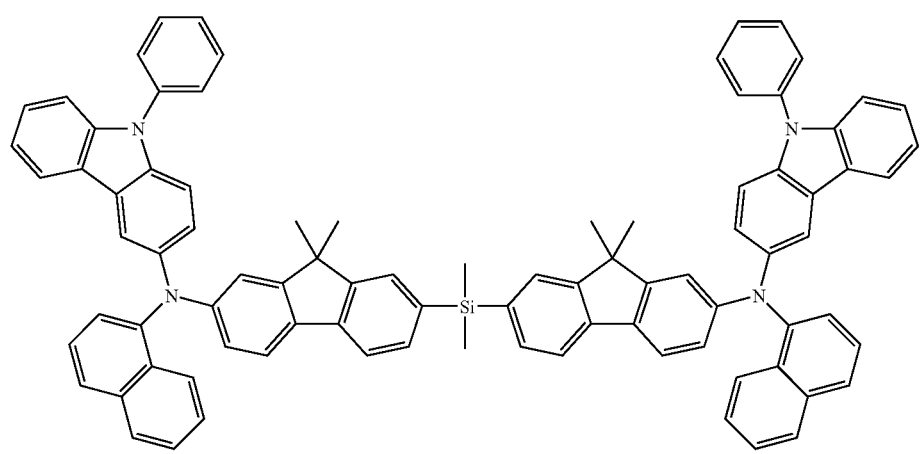
69
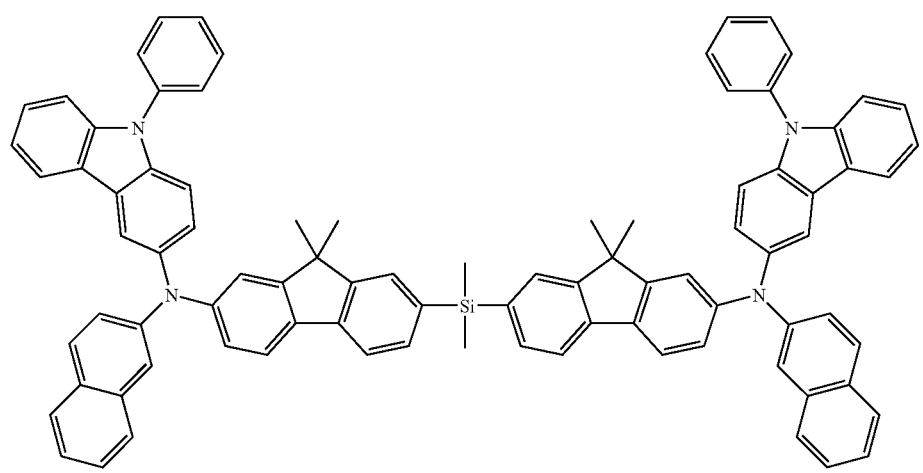
70

-continued
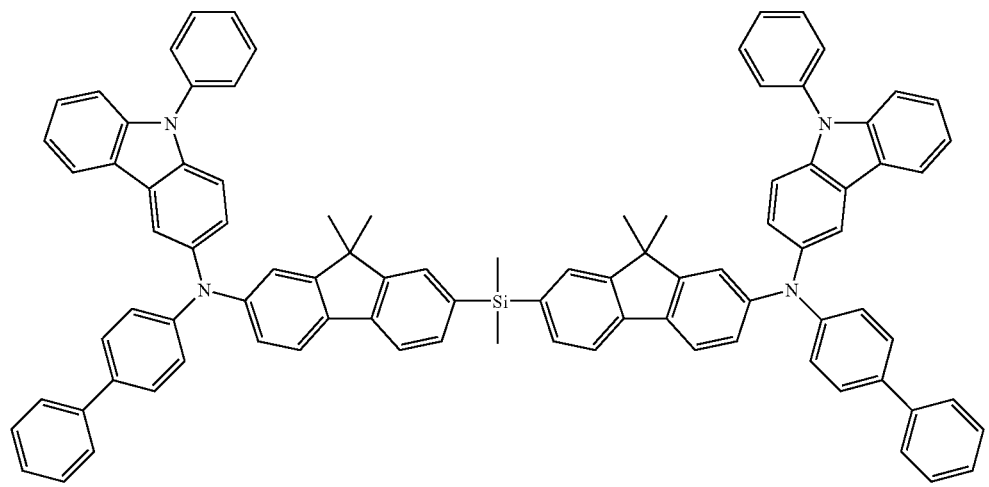
71
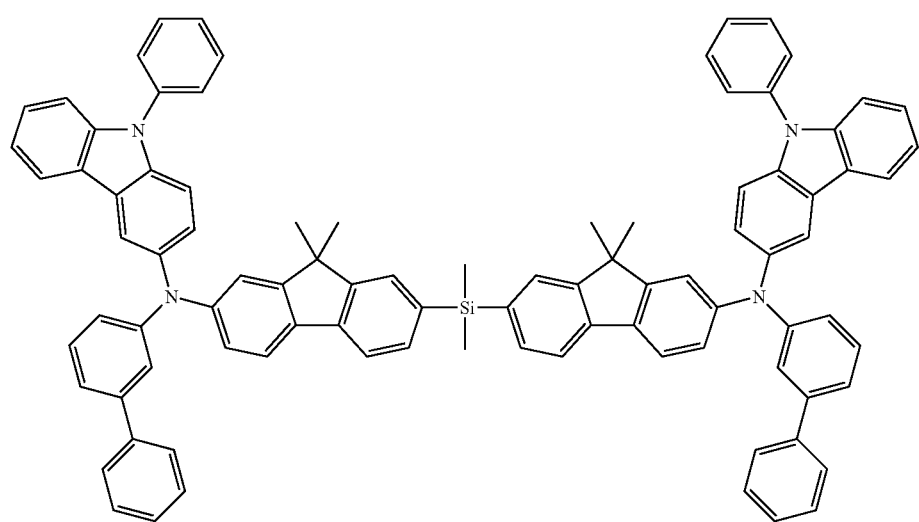
72
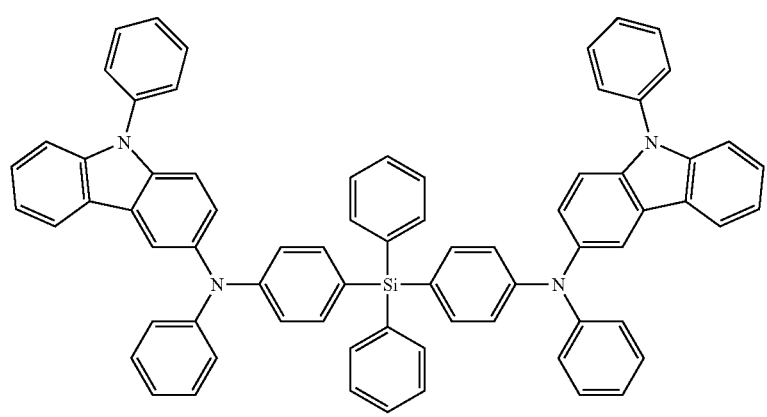
73

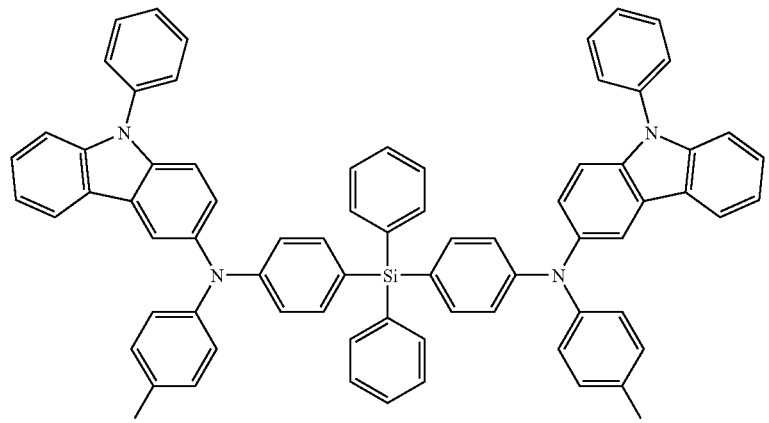
74
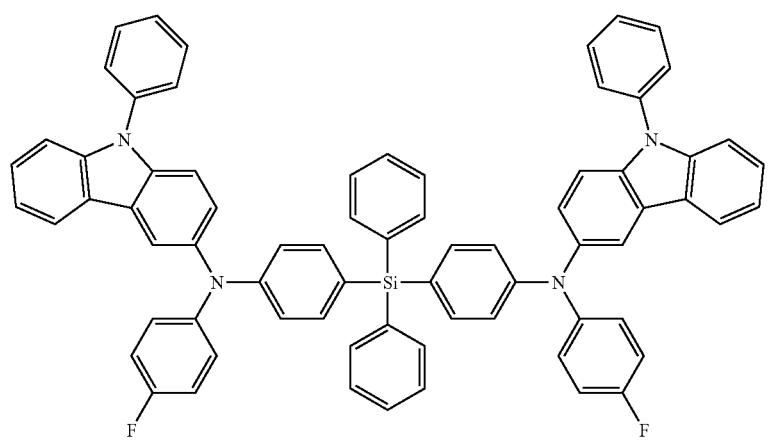
75
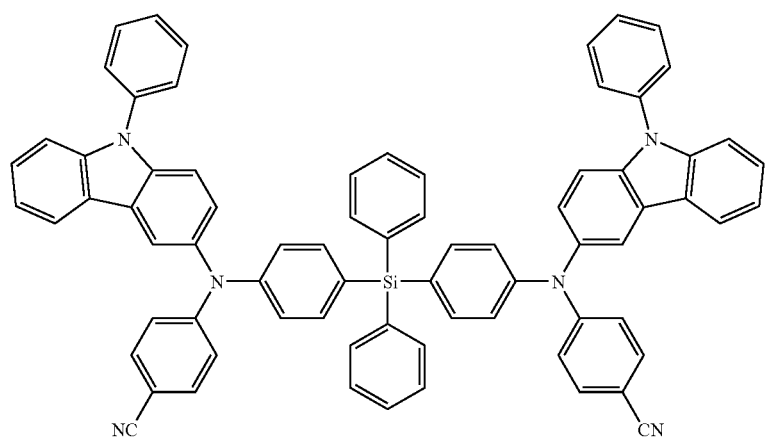
76

77
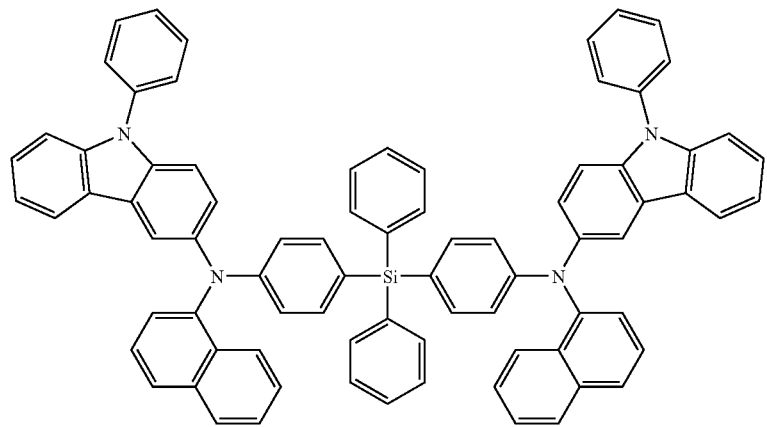
78
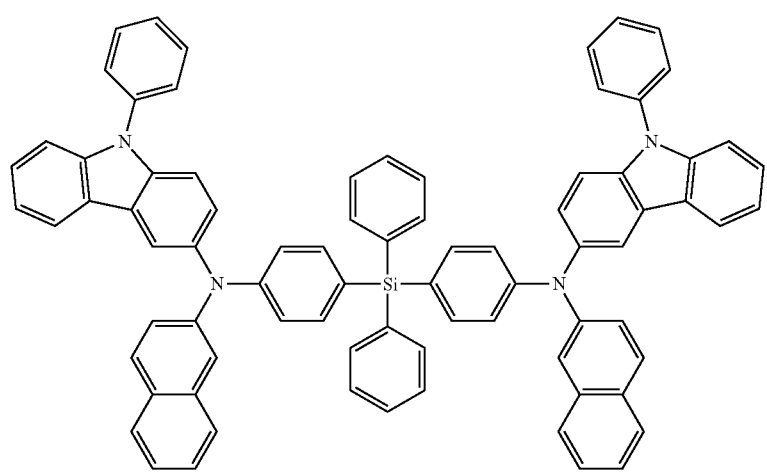
79
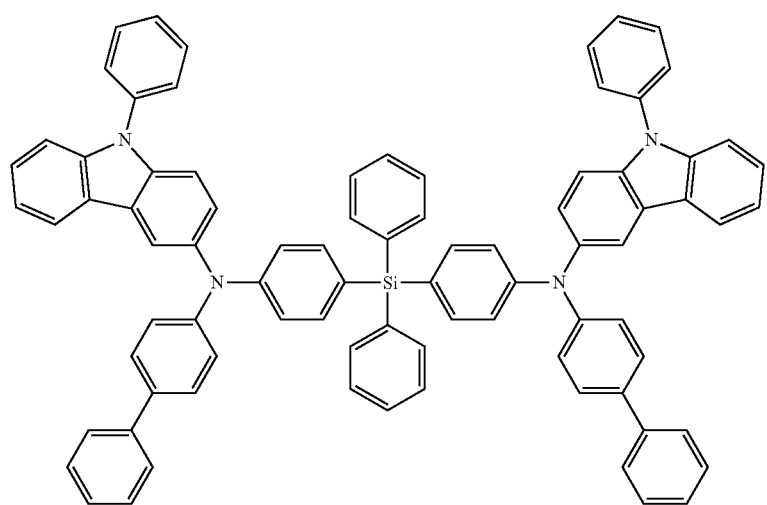

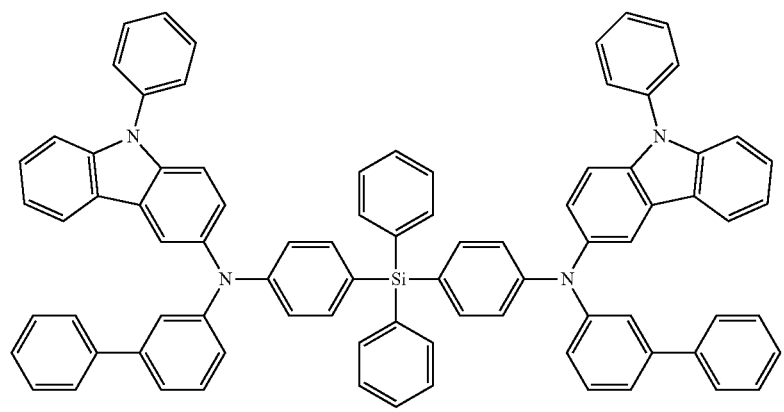
80
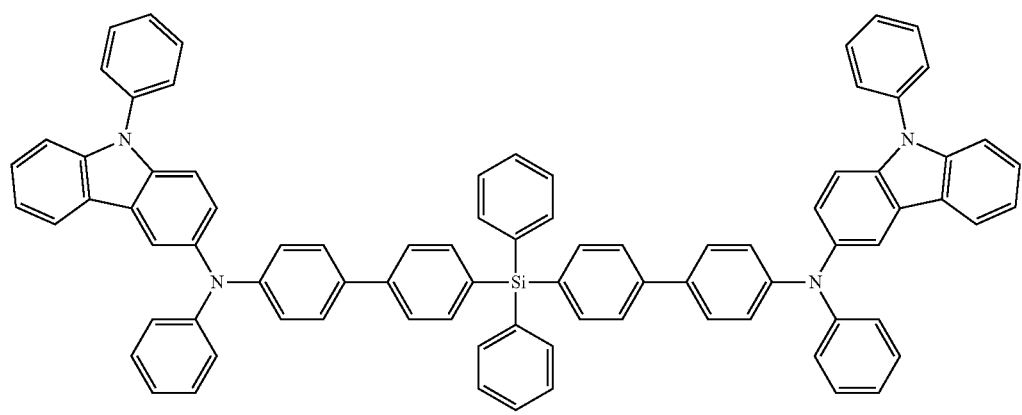
81
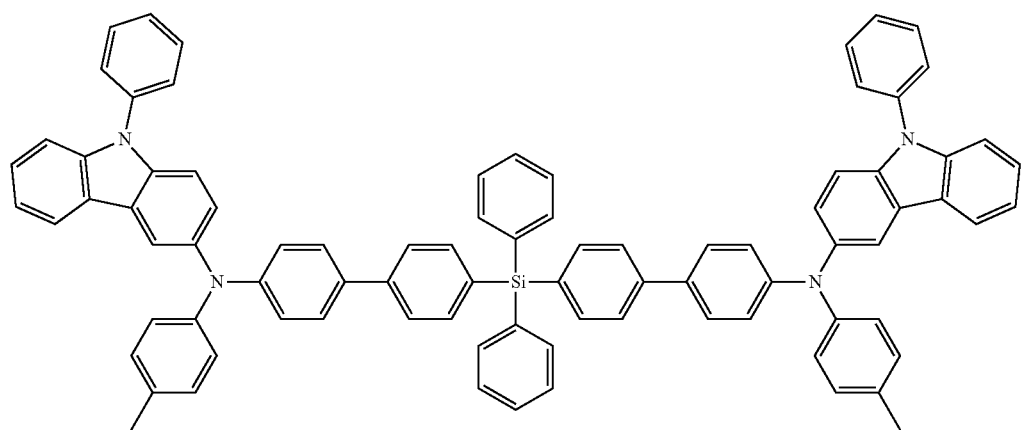
82

83
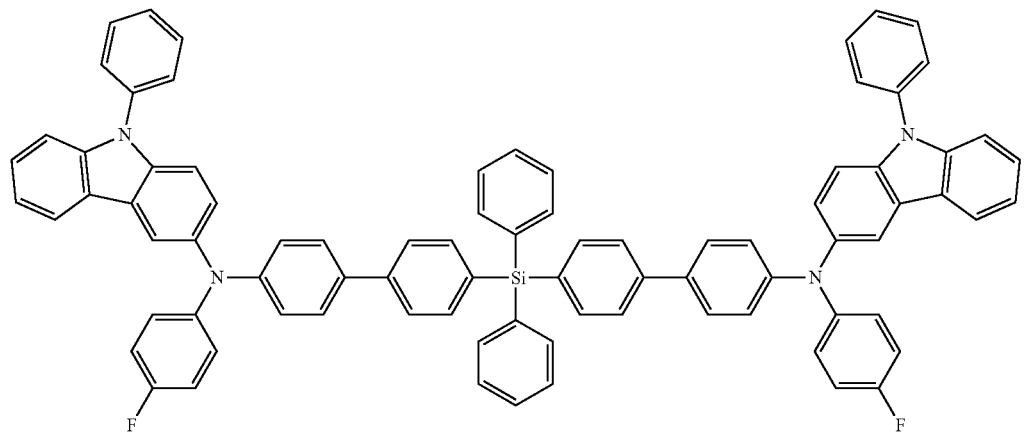
84
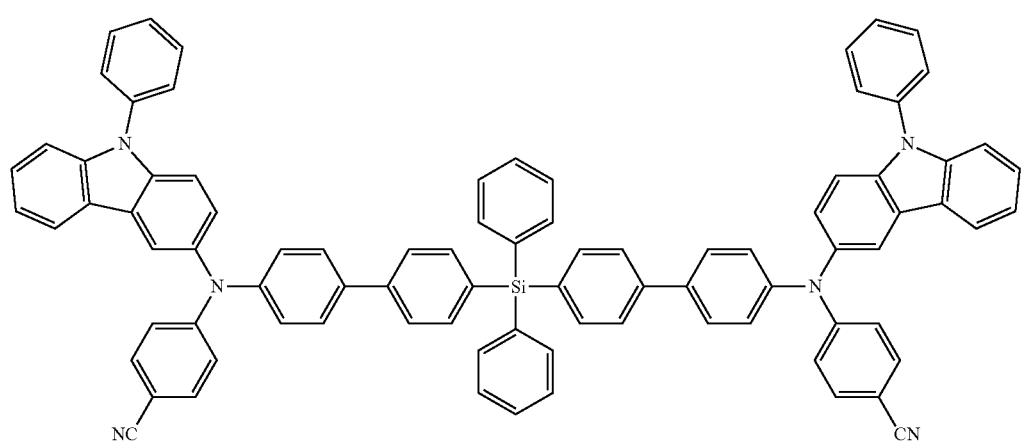
85
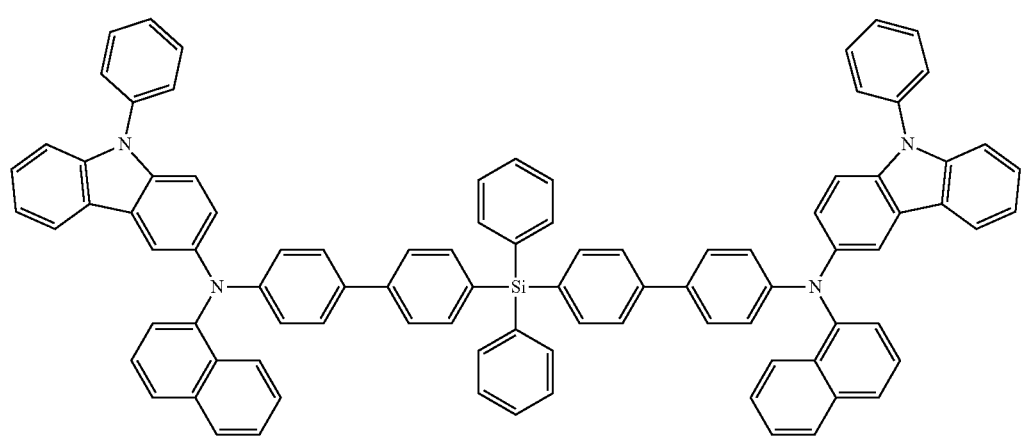

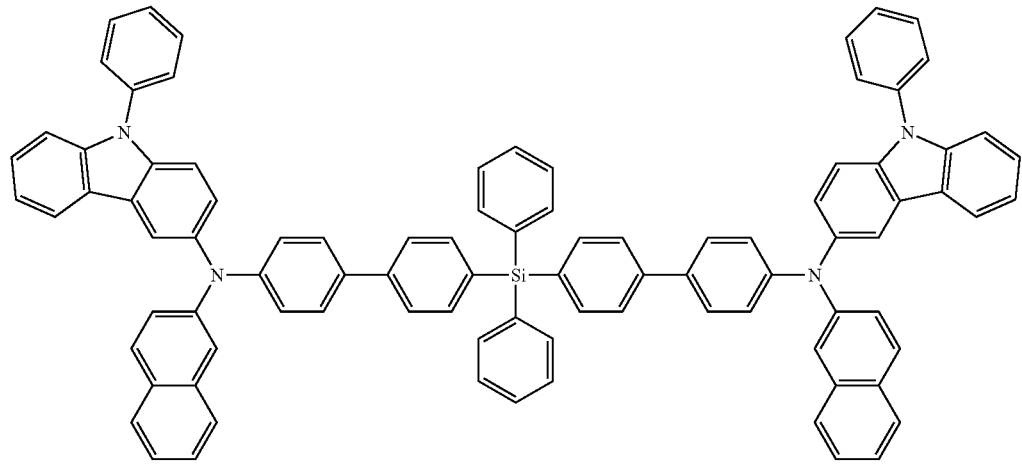
86
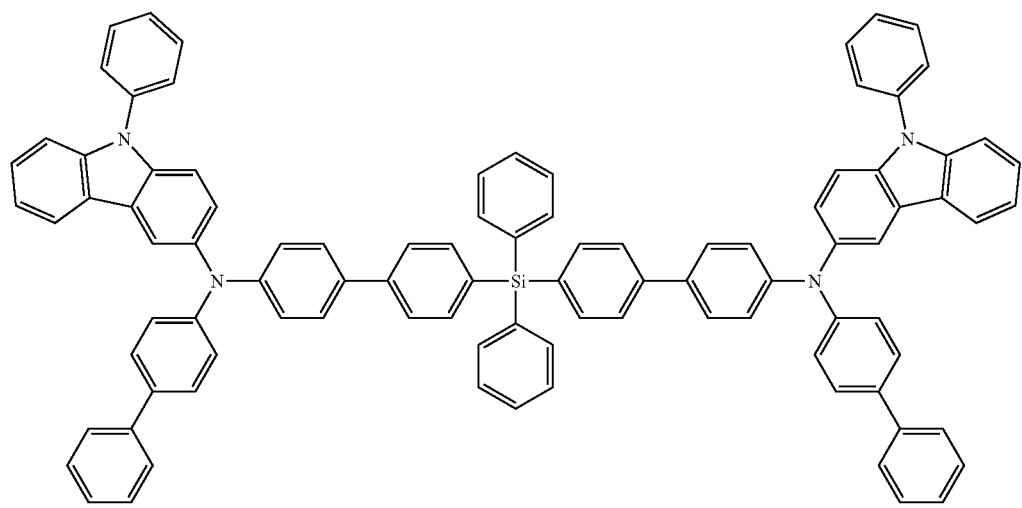
87
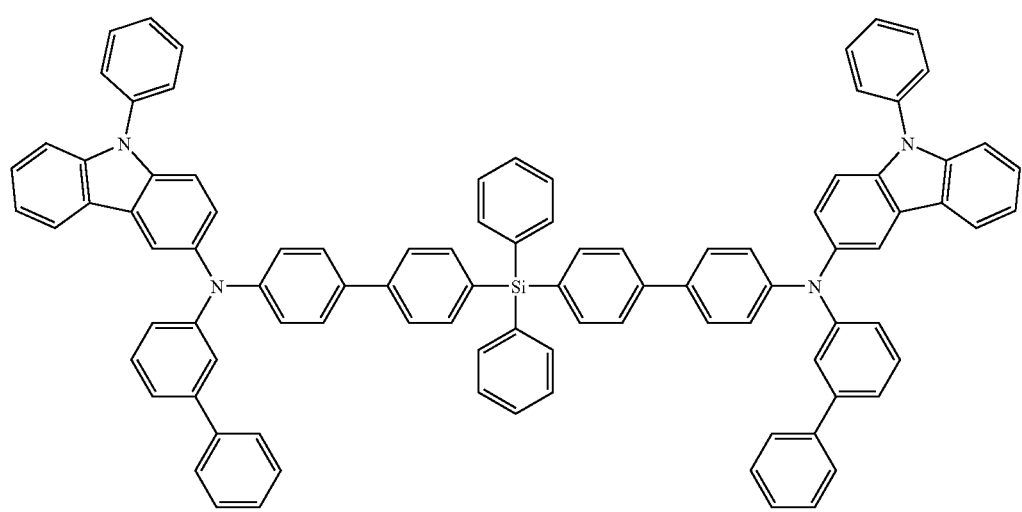
88

89
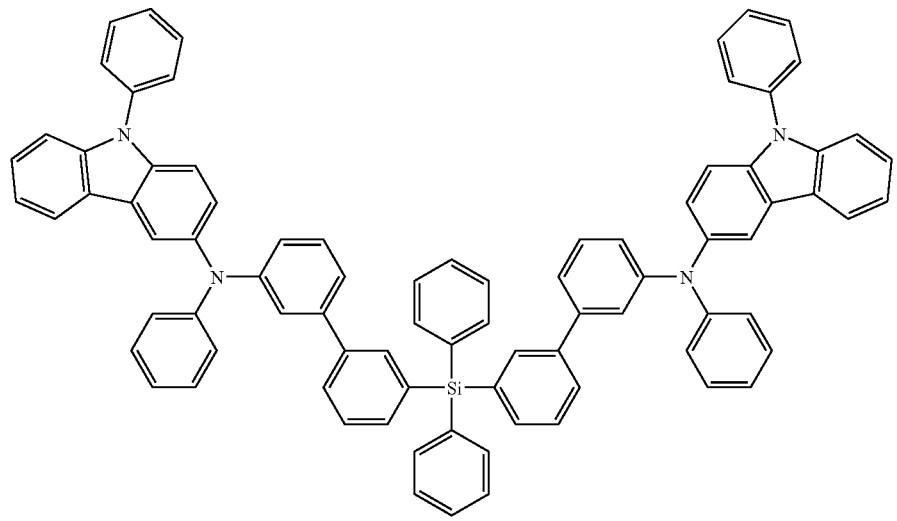
90
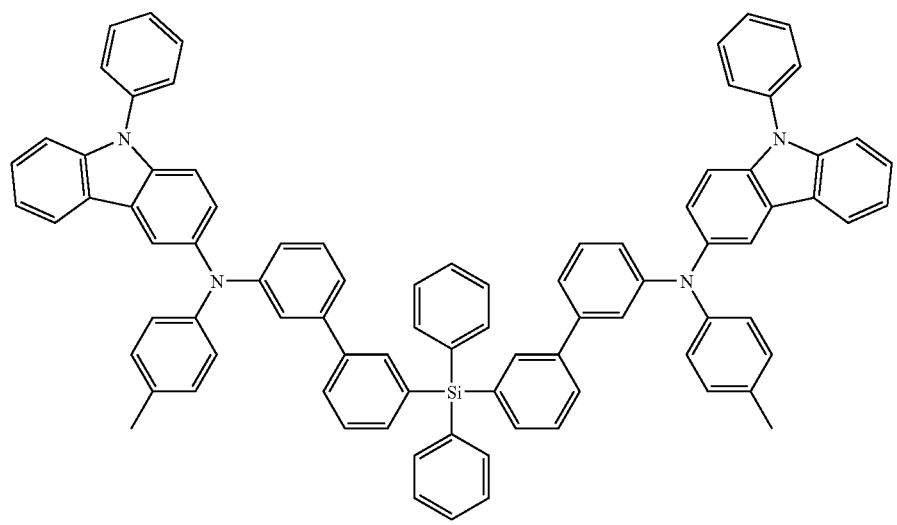
91
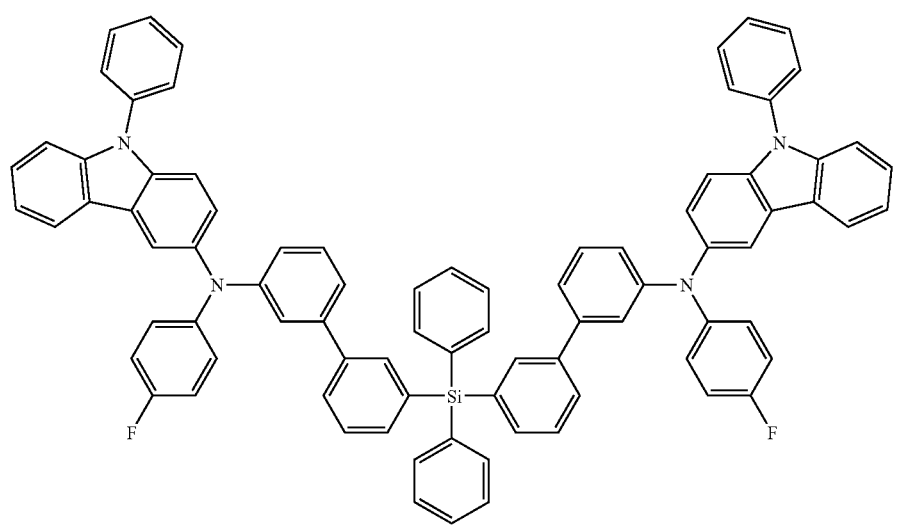

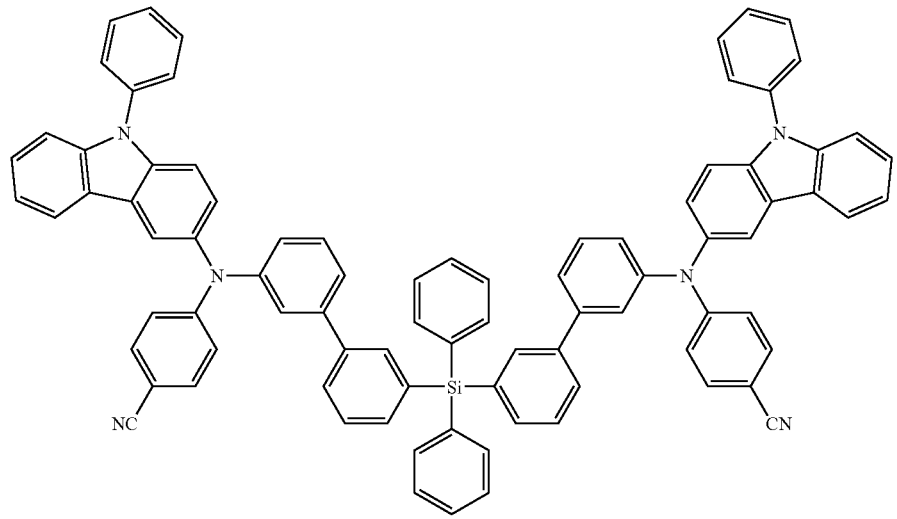
92
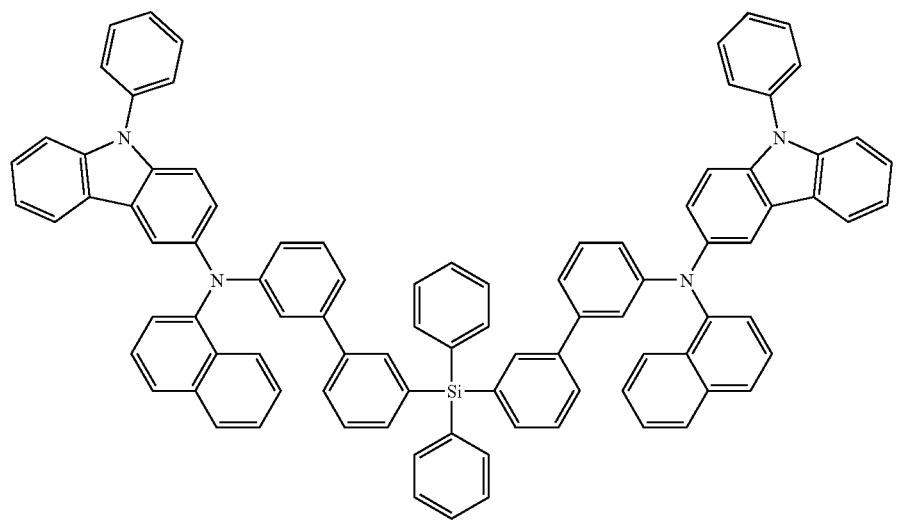
93
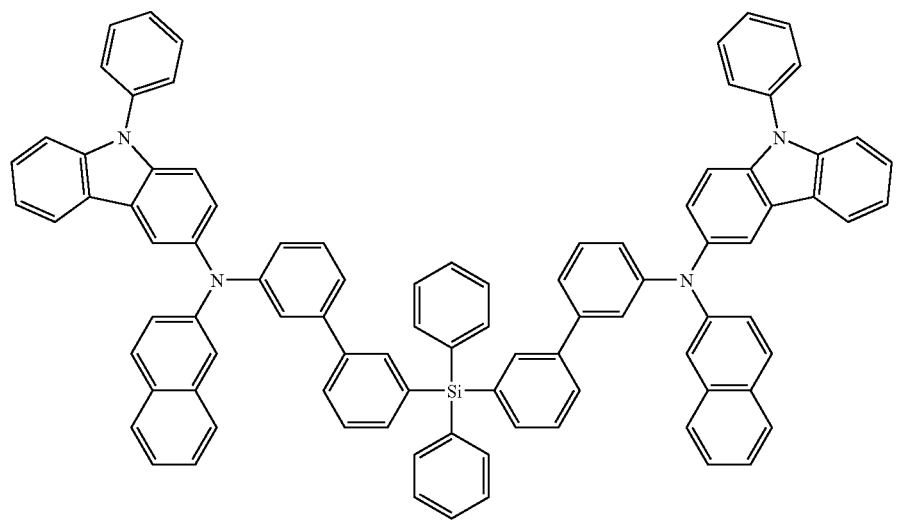
94

95
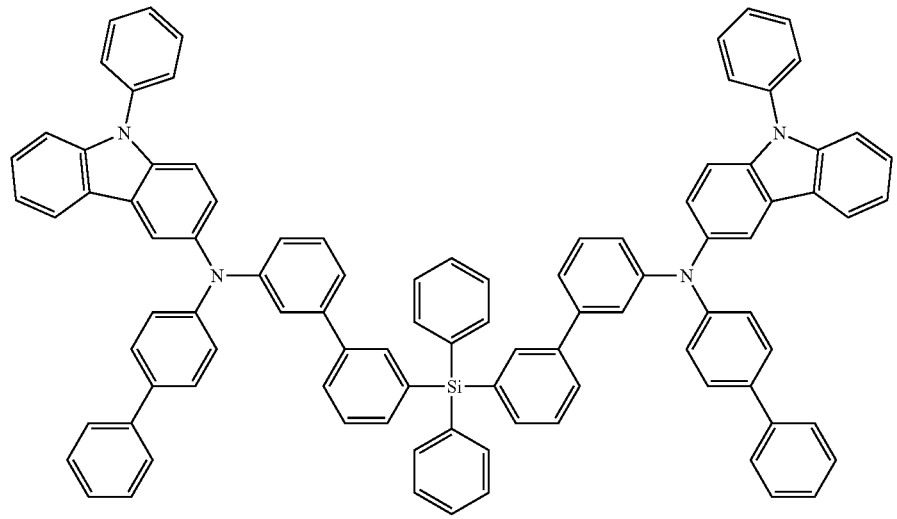
96
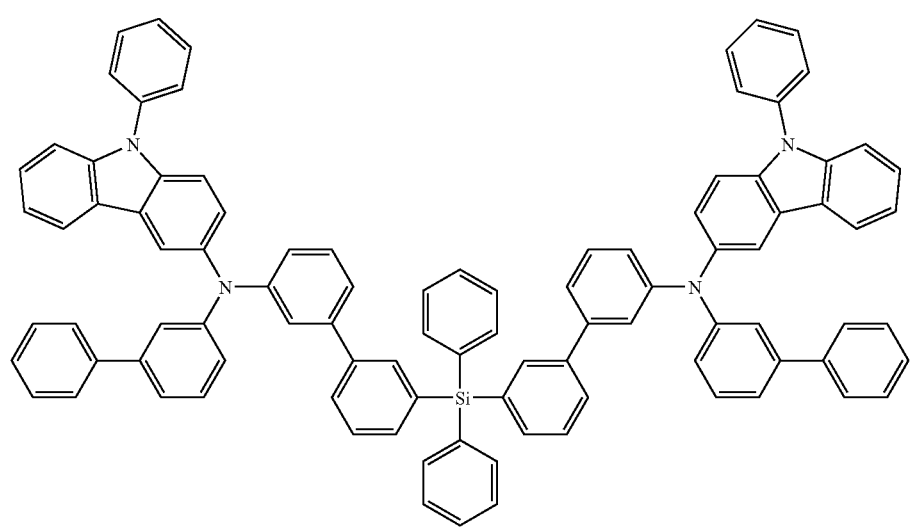
97
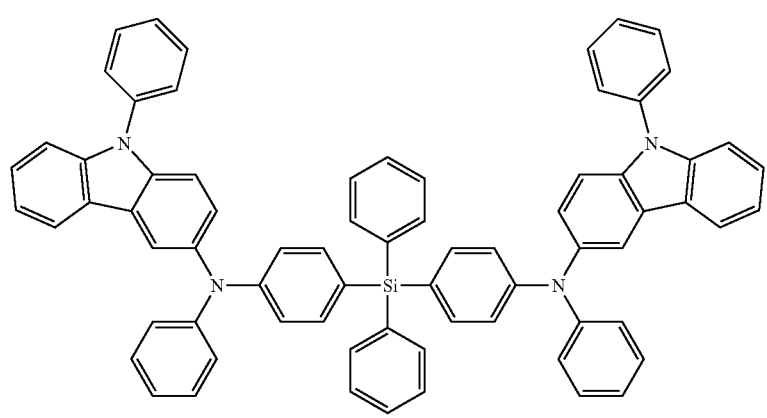

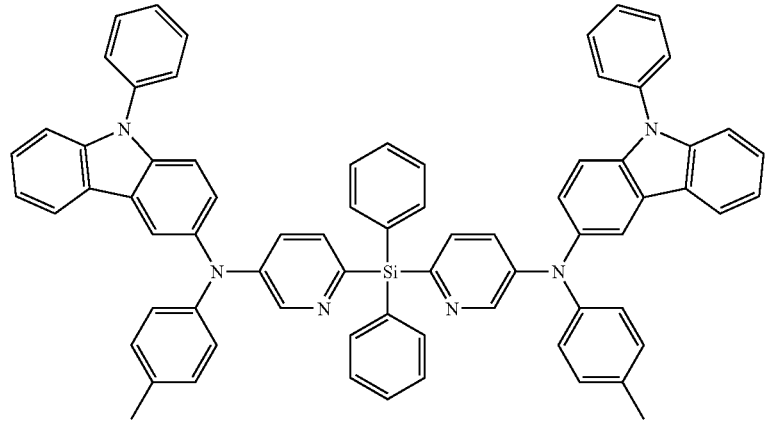
98
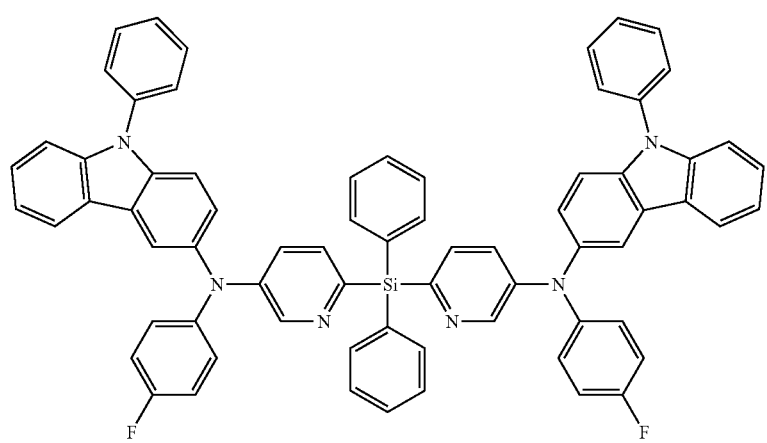
99
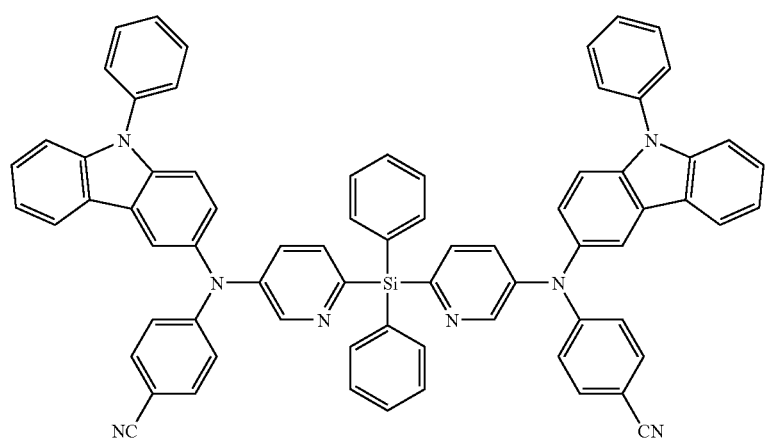
100

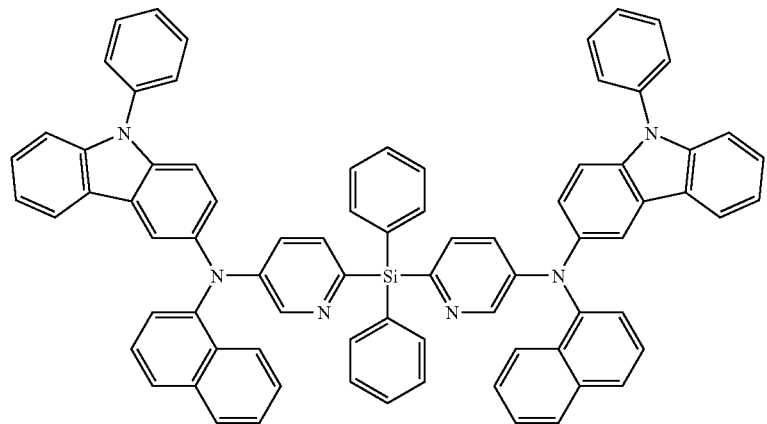
101
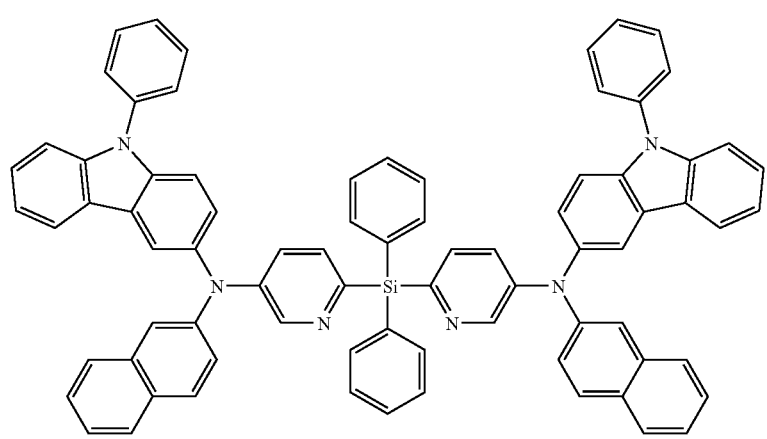
102
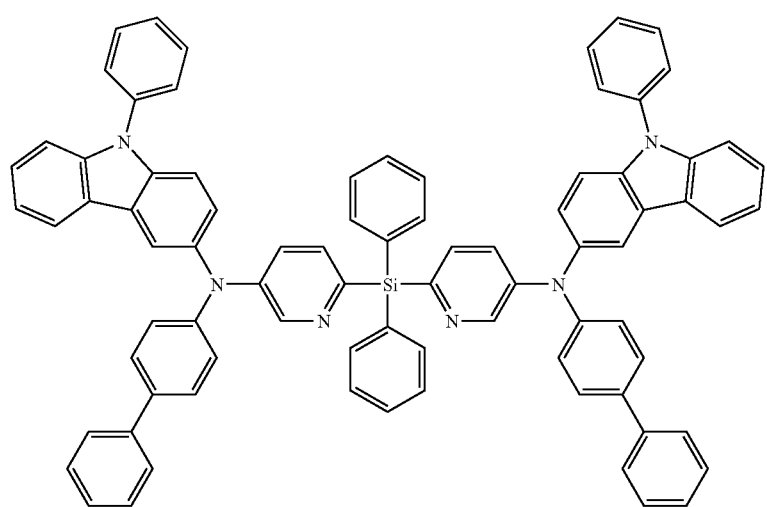
103

-continued
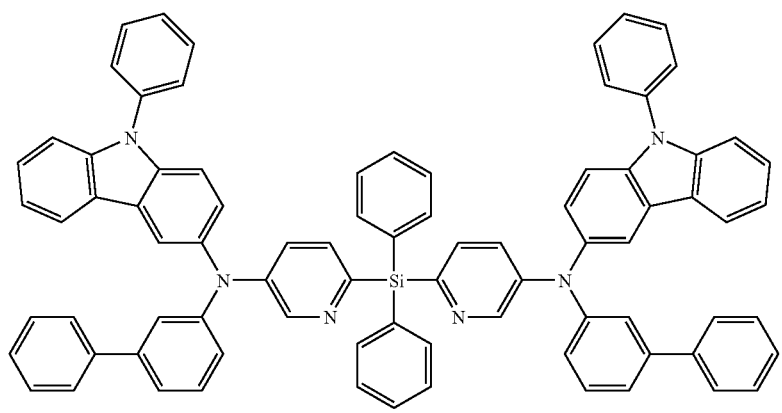
104
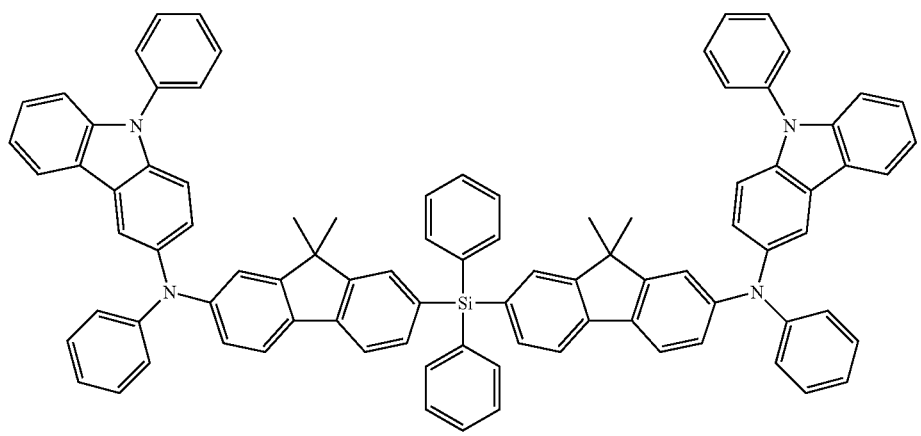
105
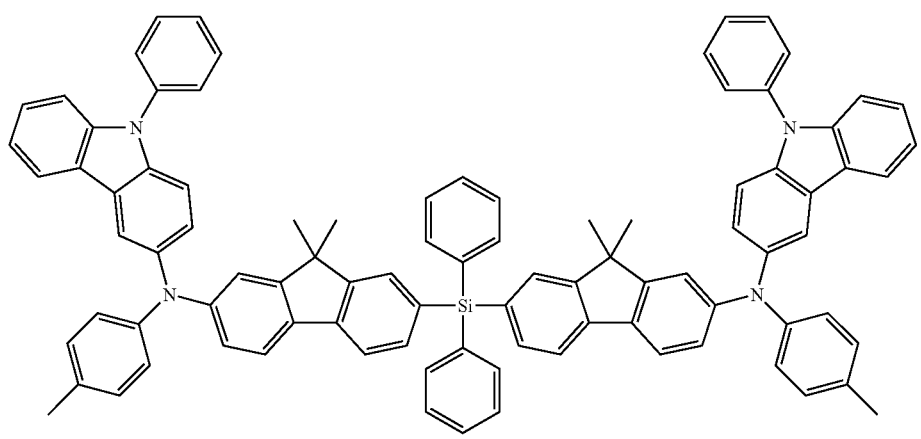
106

-continued
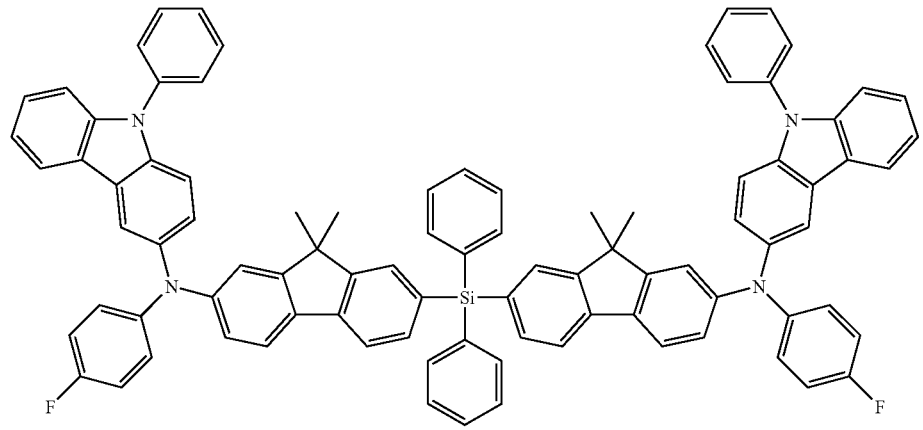
107
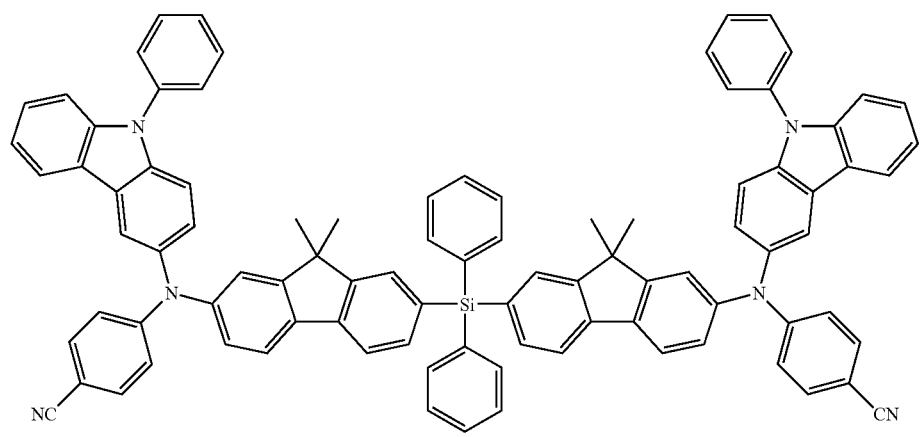
108
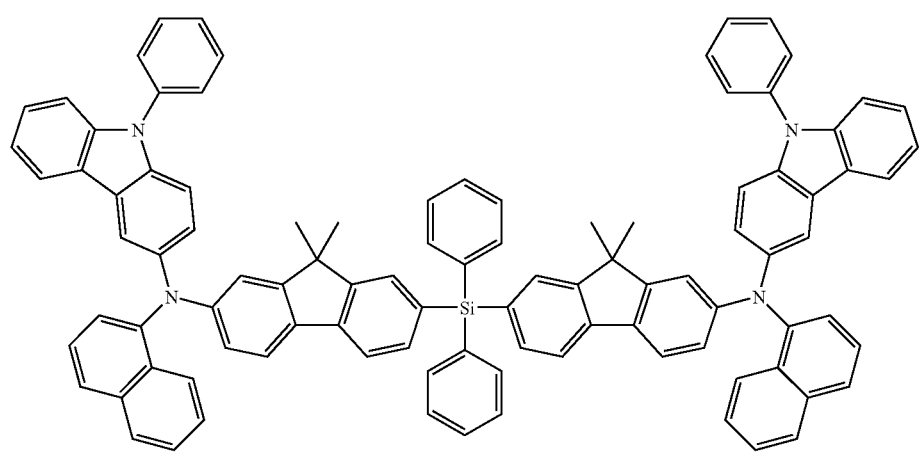
109

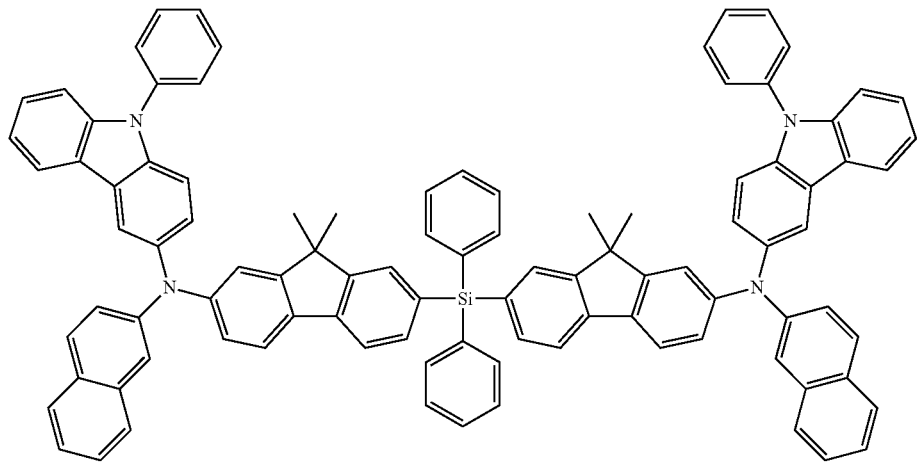

110

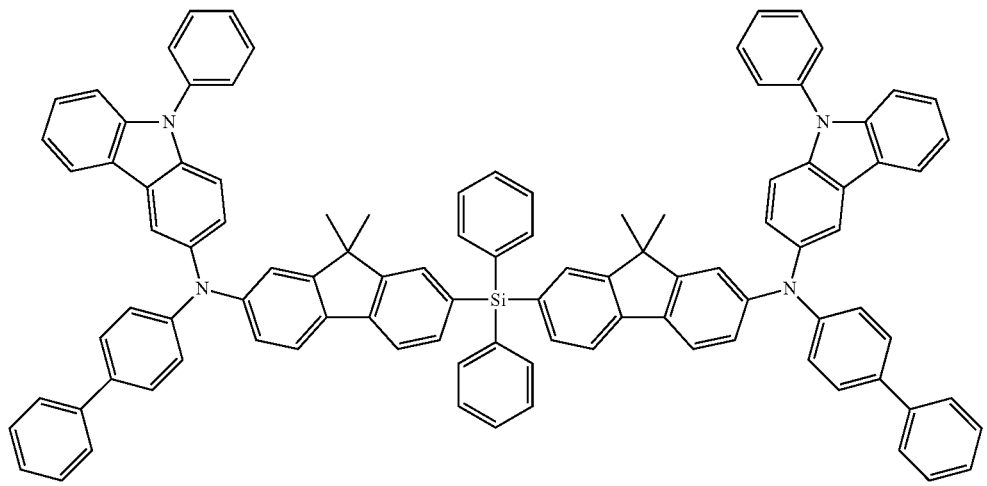

111

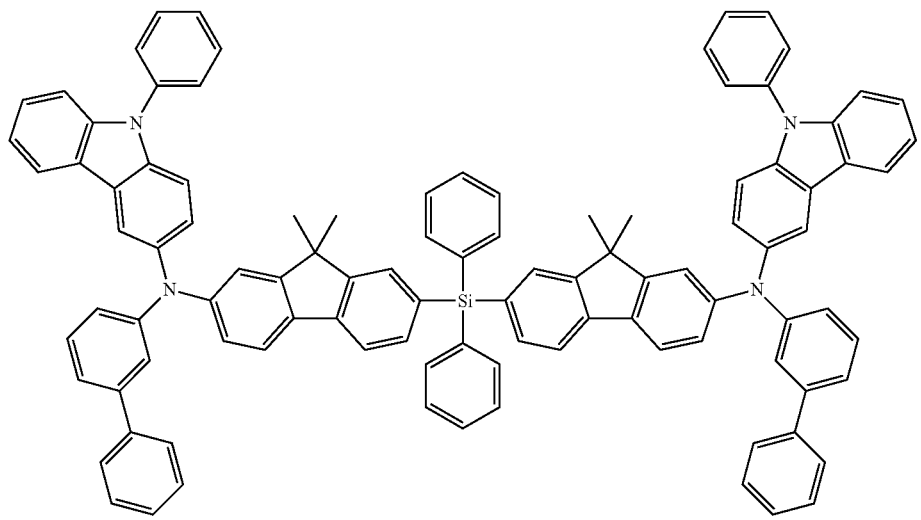

112

Some embodiments of an organic light emitting diode include a first electrode, a second electrode, and an organic layer, including the silanylamine-based compound represented by Formula 1, interposed between the first electrode and the second electrode. The organic layer including the silanylamine-based compound of Formula 1 may be a hole injection layer (HIL), a hole transport layer (HTL), or a single layer having both hole injecting and hole transporting functions. Alternatively, the organic layer including the silanylamine-based compound of Formula 1 may be an emitting layer (EML). Here, the silanylamine-based compound of Formula 1 may be a blue, green, or red fluorescent or phosphorescent host material.

The organic layer including the silanylamine-based compound of Formula 1 may be a hole injection layer (HIL).

The organic layer including the silanylamine-based compound of Formula 1 may be a hole transport layer (HTL).

Meanwhile, the first electrode may be an anode and the second electrode may be a cathode, and the reverse arrangement is also possible.

The organic light emitting diode may further include, if desired, at least one of a HIL, a HTL, an electron blocking layer (EBL), an EML, a hole blocking layer (HBL), an electron transport layer (ETL), and electron injection layer (EIL). If desired, the organic layer may be a double-layered organic layer.

For example, the organic light emitting diode may have a first electrode/HIL/EML/second electrode structure, a first electrode/HIL/HTL/EML/ETL/second electrode structure, or a first electrode/HIL/HTL/EML/ETL/EIL/second electrode structure. Alternatively, the organic light emitting diode may have a first electrode/a single layer having both hole injecting and a hole transporting functions/EML/ETL/second electrode structure, or a first electrode/a single layer having both hole injecting and a hole transporting functions/EML/ETL/EIL/second electrode structure.

The organic light emitting diode may be used in a variety of structures such as a top emission-type organic light emitting diode and a bottom emission-type organic light emitting diode.

Hereinafter, a method of preparing an organic light emitting diode is described with reference to the organic light emitting diode illustrated in FIG. 1. The organic light emitting diode of FIG. 1 includes a substrate, a first electrode (anode), a HIL, a HTL, an EML, an ETL, an EIL and a second electrode (cathode).

First, a first electrode is formed by depositing or sputtering a high work-function material on a substrate. The first electrode may be an anode or a cathode. The substrate, which is any suitable substrate that is used in organic light emitting diodes, for example, a glass substrate or a transparent plastic substrate that has excellent mechanical strength, thermal stability, transparency, and surface smoothness, which can be easily treated and is waterproof. The first electrode may be formed of ITO, IZO, SnO$_2$, ZnO, Al, Ag, Mg, or the like, and may be a transparent or reflective electrode.

Then, a HIL can be formed on the first electrode by vacuum deposition, spin coating, casting, Langmuir Blodgett (LB) deposition, or the like.

When the HIL is formed by vacuum deposition, vacuum deposition conditions may vary according to the compound that is used to form the HIL, and the desired structure and thermal properties of the HIL to be formed. In general, however, the vacuum deposition may be performed at a deposition temperature of about 100-500° C., under a pressure of from about $10^{-8}$ torr- to about $10^{-3}$ torr, at a deposition rate of about 0.01-100 Å/sec, and to a layer thickness of from about 10 Å to about 5 μm.

When the HIL is formed by spin coating, coating conditions may vary according to a compound that is used to form the HIL, and the desired structure and thermal properties of the HIL to be formed. In general, however, the coating speed may be in the range of about 2000 rpm to about 5000 rpm, and a temperature for heat treatment, which removes solvent after coating, may be in the range of about 80° C. to about 200° C.

The HIL may comprise the silanylamine-based compound of Formula 1 described above or any suitable material used in a HIL. For example, the HIL may comprise a phthalocyanine compound such as copper phthalocyanine disclosed in U.S. Pat. No. 4,356,429; a star-burst-type amine derivative such as TCTA, m-MTDATA (both shown below), and m-MTDAPB disclosed in *Advanced Materials,* 6, p. 677 (1994); or a soluble and conductive polymer such as polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrene-sulfonate) (PANI/PSS).

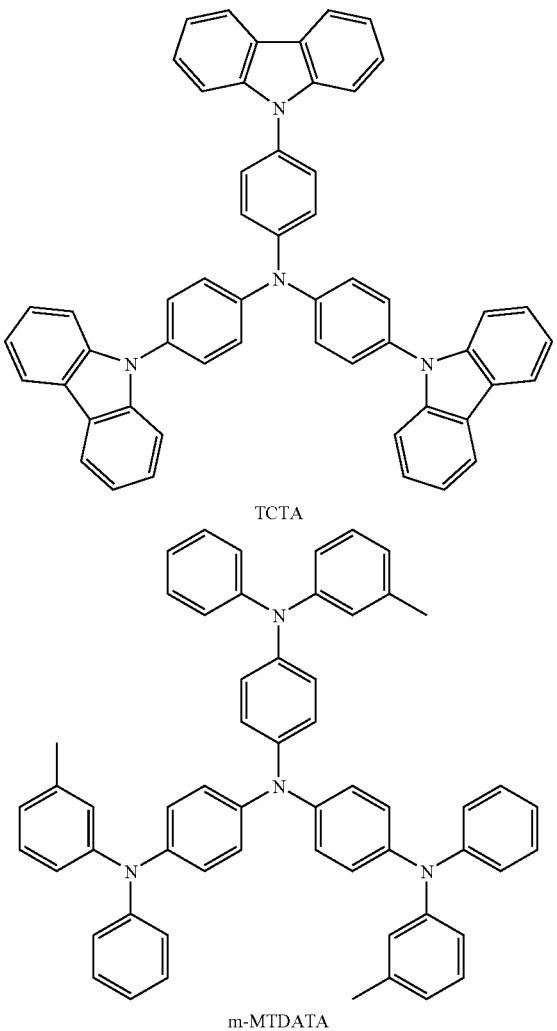

The thickness of the HIL may be in the range of from about 100 Å to about 10,000 Å, and preferably, in the range of from 100 Å to about 1000 Å. In some embodiments in which the HIL is less than about 100 Å thick, the hole injecting capability of the HIL may decrease. On the other hand, in some embodiments in which the HIL is greater than about 10,000 Å thick, a driving voltage of the device may increase.

Then, a HTL may be formed on the HIL by vacuum deposition, spin coating, casting, LB deposition, or the like. When the HTL is formed by vacuum deposition or spin coating, the conditions for deposition and coating are similar to those for the formation of the HIL, although conditions for the deposition and coating may vary according to the material that is used to form the HTL.

The HTL may comprise the silanylamine-based compound of Formula 1 described above. The HTL may comprise any suitable material used for an HTL. For example, the HTL may comprise a carbazole derivative, such as N-phenylcarbazole and polyvinylcarbazole; a typical amine derivative having a condensed aromatic ring such as 4,4'-bis[N-(1-naphthyl)-N-phenylamino]biphenyl (NPB), N,N'-bis(3-methylphenyl)-N, N'-diphenyl-[1,1-biphenyl]-4,4'-diamine (TPD) (shown below), N,N'-di(naphthalene-1-yl)-N,N'-diphenylbenzydine (α-NPD) (shown below); or the like.

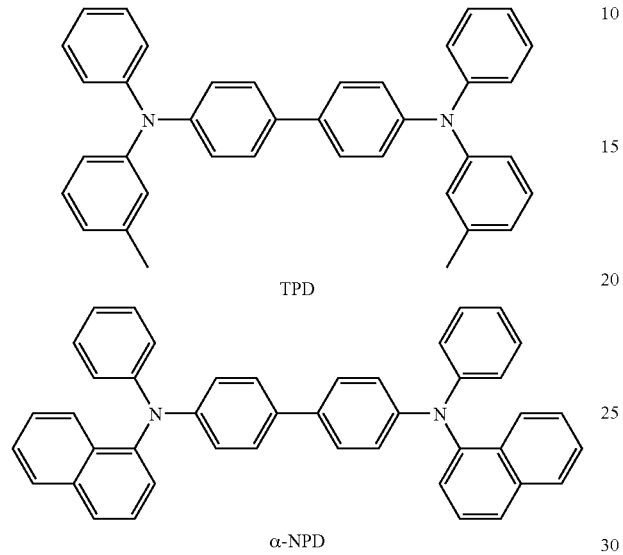

The thickness of the HTL may be in the range of from about 50 Å to about 1000 Å, and preferably from about 100 Å to about 600 Å. In some embodiments in which the HTL is less than about 50 Å thick, hole transporting properties may decrease. On the other hand, in some embodiments in which the HTL is greater than about 1000 Å thick, driving voltage may increase.

Then, an EML may be formed on the HTL by vacuum deposition, spin coating, casting, LB deposition, or the like. When the EML is formed by vacuum deposition or spin coating, the conditions for deposition and coating are similar to those for the formation of the HIL, although the conditions for deposition and coating may vary according to the material that is used to form the EML.

The EML may comprise the silanylamine-based compound represented by Formula 1. In particular, the silanylamine-based compound of Formula 1 may be used as a host. The EML may comprise various suitable emitting materials, and may also comprise a suitable host and dopant. The dopant may be any suitable fluorescent dopant or phosphorescent dopant.

For example, the host may be Alq$_3$, 4,4'-N,N'-dicarbazole-biphenyl (CBP), poly(n-vinylcarbazole) (PVK), distyrylarylene (DSA), IDE215 (Idemitsu, Tokyo), or the like, but is not limited thereto.

The fluorescent dopant may be IDE102, IDE105, and IDE118 (Idemitsu, Tokyo), and the phosphorescent dopant may be Ir(ppy)$_3$ (ppy=phenylpyridine) (green), (4,6-F2ppy)$_2$ Irpic (Chihaya Adachi et al. *Appl. Phys. Lett.*, 79, 2082-2084, 2001), TEB002 (Covion, Frankfurt), platinum(II) octaethylporphyrin (PtOEP), a compound represented by Formula 6 below (Korean Patent Publication No. 2005-0078472), Firpic, RD 61, which is a red fluorescent dopant (Universal Display, Ewing, N.J.), or the like, but is not limited thereto.

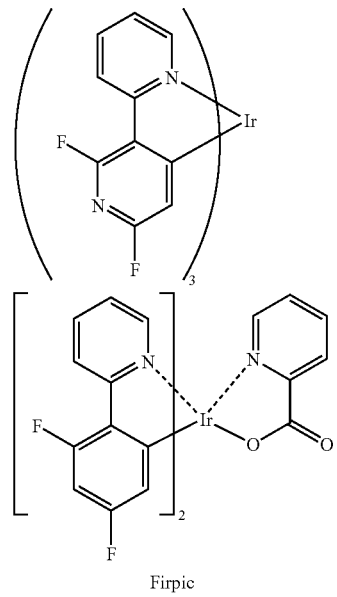

The amount of the dopant may be from about 0.1 parts to about 20 parts by weight, and preferably from about 0.5 parts to about 12 parts by weight based on 100 parts by weight of a material used to form the EML, that is, the total weight of the host and the dopant. In some embodiments in which the amount of the dopant is less than about 0.1 parts by weight based on 100 parts by weight of the total weight of the host and the dopant, the effect of adding the dopant is minute. On the other hand, in some embodiments in which the amount of the dopant is greater than about 20 parts by weight based on 100 parts by weight of the total weight of the host and the dopant, concentration extinction for both the phosphorescence and fluorescence such as concentration quenching may occur.

The thickness of the EML may be in the range of from about 100 Å to about 1000 Å, and preferably from about 200 Å to about 600 Å. In some embodiments in which the thickness of the EML is less than about 100 Å, light-emitting properties may decrease. On the other hand, in some embodiments in which the thickness of the EML is greater than about 1000 Å, driving voltage may increase.

A hole blocking layer (HBL) (not shown in FIG. 1) may be formed on the EML to prevent diffusion of triplet excitons and/or holes into the ETL when the EML includes a phosphorescent dopant. The HBL may comprise any suitable material used to form a HBL, for example, an oxadiazole derivative, a triazole derivative, a phenanthroline derivative, a hole blocking material disclosed in Japanese Patent No. 11-329734(A1), Balq or BCP, but the material is not limited thereto.

The thickness of the HBL may be in the range of from about 50 Å to about 1000 Å, and preferably, from about 100 Å to about 300 Å. In some embodiments in which the HBL is less than about 50 Å thick, hole blocking properties may decrease. On the other hand, in some embodiments in which the HBL is greater than about 1000 Å thick, driving voltage may increase.

Then, an electron transport layer (ETL) is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material used in the ETL.

The ETL may comprise of any suitable material that is used to form an ETL without limitation. For example, the ETL may comprise a quinoline derivative, in particular, tris(8-quinolinorate)aluminum ($Alq_3$), TAZ, Balq, or the like.

The thickness of the ETL may be in the range of from about 100 Å to about 1000 Å, and preferably, from about 100 Å to about 500 Å. In some embodiments in which the ETL is less than about 100 Å thick, electron transporting capability may decrease. On the other hand, in some embodiments in which the ETL is greater than about 1000 Å thick, driving voltage may increase.

Then, an electron injection layer (EIL), which comprises a material allowing easy injection of electrons from a cathode, may be formed on the ETL.

The EIL may comprise any suitable material known in the art, for example, LiF, NaCl, CsF, $Li_2O$, BaO, or The like. Conditions for the depositing the EIL are, in general, similar to conditions for forming the HIL, although particular conditions may vary according to the material that is used to form the EIL.

The thickness of the EIL may be in the range of from about 1 Å to about 100 Å, and preferably, from about 5 Å to about 90 Å. In some embodiments in which the EIL is less than about 1 Å thick, the electron injecting capability may decrease. On the other hand, in some embodiments in which the EIL is greater than about 100 Å thick, the driving voltage of the device may increase.

Finally, a second electrode may be formed on the EIL by vacuum deposition, sputtering, or the like. The second electrode may be a cathode or an anode. second electrode may comprise a low work-function metal, alloy, electrically conductive compound, or a combination of these. In detail, the second electrode may comprise Li, Mg, Al, Al—Li, Ca, Mg—In, Mg—Ag, or the like. Alternatively, a transparent cathode comprising ITO or IZO may be used to produce a top emission type organic light emitting device.

Hereinafter, certain embodiments will be described in greater detail with reference to following synthesis examples and examples representing Compounds 1 and 73. The following synthesis examples and examples are illustrative only, and are not intended to limit the scope of the disclosure.

EXAMPLES

Synthesis Example 1

Preparation Of Compound 1

Compound 1 was synthesized through Reaction Scheme 1 below.

Reaction Scheme 1

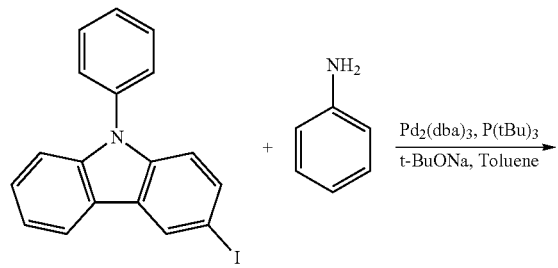

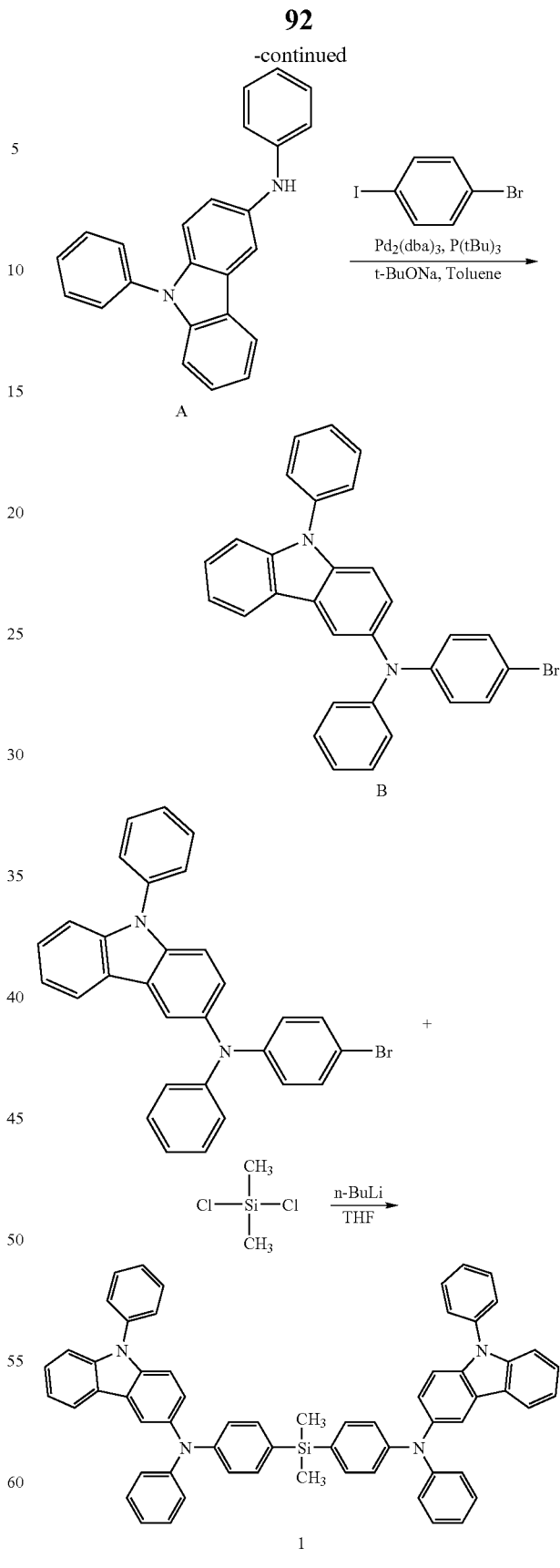

Synthesis of Intermediate A 36.9 g (100 mmol) of 3-iodo-9-phenylcarbazole, 13.7 mL (150 mmol) of aniline, 14 g (150 mmol) of t-BuONa, 1.83 g (2 mmol) of Pd$_2$(dba)$_3$, 400 mg (2 mmol) of P(t-Bu)$_3$ were dissolved in 250 ml of toluene, then was stirred for 3 hours at 90° C. After the reaction was complete, the product was cooled to room temperature, and then was extracted 3 times with deionized water and 200 ml of diethyl ether. The collected organic layer was dried with magnesium sulfate, and the residue obtained by evaporating the solvent was separated and purified with silica gel column chromatography to obtain 3.07 g (yield 92%) of Intermediate A.

$^1$H NMR (CDCl$_3$, 400 MHz) δ (ppm): 8.03-7.99 (m, 1H), 7.67 (d, 1H), 7.49 (d, 5H), 7.43 (d, 1H), 7.36-7.32 (m, 3H), 7.18 (t, 2H), 7.02 (dd, 2H), 6.95 (dd, 1H), 6.73 (t, 1H), 5.68 (s, 1H).

$^{13}$C NMR (CDCl$_3$, 100 MHz) δ (ppm): 144.7, 139.9, 137.4, 135.7, 129.8, 129.4, 128.1, 127.4, 127.1, 126.3, 119.1, 118.7, 118.5, 116.8, 113.1, 111.2, 109.4, 102.5.

Synthesis of Intermediate B 4.24 g (15 mmol) of 1-bromo-4-iodobenzene, 3.34 g (10 mmol) of intermediate A, 1.4 g (15 mmol) of t-BuONa, 0.18 g (0.2 mmol) of Pd$_2$(dba)$_3$, 40 mg (0.2 mmol) of P(t-Bu)$_3$ were dissolved in 25 ml of toluene, then was stirred for 3 hours at 90° C. After the reaction was complete, the product was cooled to room temperature, and then was extracted 3 times with deionized water and 30 ml of diethyl ether. The collected organic layer was dried with magnesium sulfate, and the residue obtained by evaporating the solvent was separated and purified with silica gel column chromatography to obtain 3.43 g (yield 70%) of Intermediate B.

$^1$H NMR (CDCl$_3$, 300 MHz) δ (ppm): 7.99 (d, 1H), 7.90 (d, 1H), 7.62-7.55 (m, 4H), 7.48-7.46 (m, 1H), 7.39-7.18 (m, 10H), 7.10 (d, 2H), 7.00-6.96 (m, 3H).

$^{13}$C NMR (CDCl$_3$, 100 MHz) δ (ppm)" 148.0, 147.8, 141.4, 140.0, 138.2, 137.6, 131.9, 129.9, 129.2, 127.5, 127.0, 126.2, 125.5, 124.4, 123.7, 123.2, 122.9, 122.3, 120.5, 120.0, 118.5, 113.5, 110.8, 109.9.

Synthesis of Compound 1

A solution of 10.76 g (22 mmol) of intermediate B in 30 mL of THF was slowly added 9.68 mL (11 mmol) of n-BuLi (2.5M in Hexane) at −78° C. After stirred 1 hr, the reaction mixture was added 1.29 g (10 mmol) of dichlorodimethylsilane in 5 mL of THF at the same temperature. After additional stirring of 1 hr at −78° C., the reaction mixture was warm to room temperature. After the reaction was completed, the mixture was extracted three times with 40 mL each of distilled water and diethyl ether. The collected organic layers were dried with magnesium sulfate, and the solvent was evaporated. The residue was purified using silica gel column chromatography to obtain 6.58 g of white solid Compound 1 (Yield: 75%).

$^1$H NMR (CDCl$_3$, 400 MHz) δ (ppm): 8.08 (d, 2H), 8.05 (d, 2H), 7.67-7.65 (m, 8H), 7.55-7.43 (m, 12H), 7.35-7.27 (m, 12H), 7.19 (d, 4H), 7.08 (t, 2H), 0.64 (s, 6H).

$^{13}$C NMR (CDCl$_3$, 100 MHz) δ (ppm): 149.2, 148.1, 141.3, 140.1, 138.1, 137.6, 135.0, 129.9, 129.8, 129.1, 127.4, 126.9, 126.1, 125.9, 124.3, 123.4, 123.0, 122.1, 120.9, 120.5, 119.9, 118.8, 110.7, 109.8.

Synthesis Example 2

Preparation of Compound 73

Compound 73 was synthesized through Reaction Scheme 2 below.

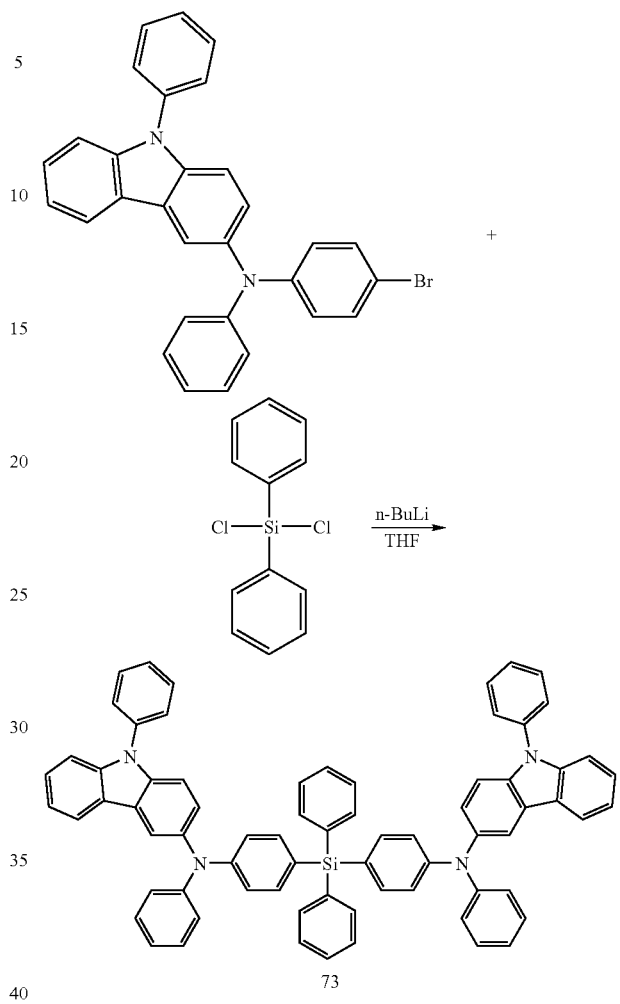

Reaction Scheme 2

Synthesis of Compound 73

A solution of 10.76 g (22 mmol) of intermediate B in 30 mL of THF was slowly added 9.68 mL (11 mmol) of n-BuLi (2.5M in Hexane) at −78° C. After stirred 1 hr, the reaction mixture was added 2.53 g (10 mmol) of dichlorodiphenylsilane in 5 mL of THF at the same temperature. After additional stirring of 1 hr at −78° C., the reaction mixture was warm to room temperature. After the reaction was completed, the mixture was extracted three times with 40 mL each of distilled water and diethyl ether. The collected organic layers were dried with magnesium sulfate, and the solvent was evaporated. The residue was purified using silica gel column chromatography to obtain 7.91 g of white solid Compound 1 (Yield: 79%).

$^1$H NMR (CDCl$_3$, 400 MHz) δ (ppm): 7.99 (d, 2H), 7.95 (d, 2H), 7.61-7.54 (m, 12H), 7.46-7.33 (m, 18H), 7.24-7.16 (m, 12H), 7.04 (d, 4H), 6.97 (t, 2H).

$^{13}$C NMR (CDCl$_3$, 100 MHz) δ (ppm): 149.6, 148.0, 141.4, 139.9, 138.3, 137.6, 137.2, 136.3, 135.3, 129.9, 129.3, 129.1, 127.7, 127.5, 127.0, 126.1, 125.3, 124.4, 123.8, 123.0, 122.4, 120.5, 120.4, 119.9, 119.1, 110.7, 109.9.

Example 1

A Corning 15 Ωcm$^2$ (1200 Å) ITO glass substrate was cut into a rectangle of 50 mm×50 mm×0.7 mm, sonicated with isopropyl alcohol for 15 minutes and with pure water for 15 minutes, irradiated with UV light for 30 minutes, and exposed to ozone to prepare an anode. The anode was installed in a vacuum deposition device.

First, 2-TNATA (shown below) was vacuum deposited on the substrate to a thickness of 600 Å to form an HIL, and then Compound 1 was vacuum deposited on the HIL to a thickness of 300 Å to form a HTL.

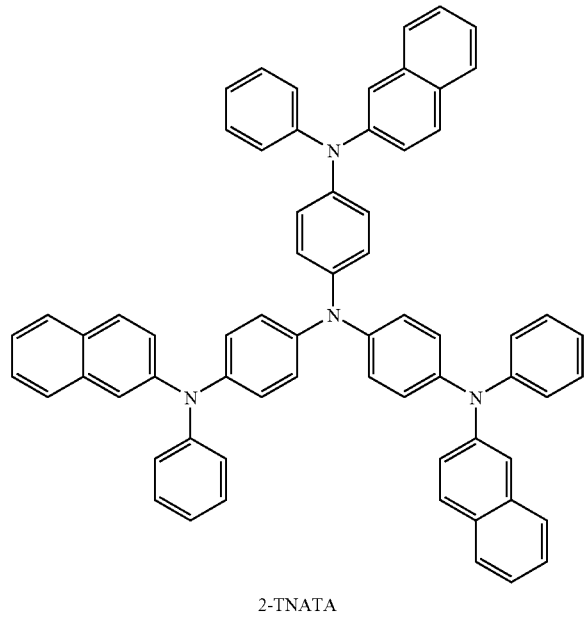

2-TNATA

Then, IDE 215 (Idemitsu Co.), a blue fluorescent host, and IDE 118 (Idemitsu Co.), a blue fluorescent dopant, were co-deposited with a weight ratio of 98:2 on the HTL to form an EML with a thickness of 200 Å.

Then, $Alq_3$ was deposited on the EML to a thickness of 300 Å to form an ETL. LiF was vacuum deposited on the EML to a thickness of 10 Å as an electron injection layer (EIL), and Al was vacuum deposited on the EIL to a thickness of 3000 Å as a cathode electrode to complete an organic light emitting diode.

The organic light emitting diode had a driving voltage of 7.12 V at a current density of 100 $mA/cm^2$, a brightness of 7,709 $cd/m^2$, color coordinates of (0.143, 0.230), and a light emitting efficiency of 7.71 cd/A.

Example 2

An organic light emitting diode was prepared in the same manner as in Example 1, except that Compound 73 was used instead of Compound 1 in the HIL.

The organic light emitting diode had a driving voltage of 7.23 V at a current density of 100 $mA/cm^2$, a brightness of 8,525 $cd/m^2$, color coordinates of (0.144, 0.231), and a light emitting efficiency of 8.53 cd/A.

Comparative Example 1

An organic light emitting diode was prepared in the same manner as in Example 1, except that 4,4'-bis[N-(1-naphthyl)-N-phenylamino]biphenyl (NPB) was used instead of Compound 1 in the HTL.

The resulting organic light emitting diode had a driving voltage of 7.45 V at a current density of 100 $mA/m^2$, a brightness of 6,102 $cd/m^2$, color coordinates of (0.144, 0.232), and a light emitting efficiency of 6.1 cd/A As a result of using the compounds represented by Formula 1 as a HTL material in an organic light emitting diode, driving voltage decreased. Efficiency of the organic light emitting diode was increased by 26% when Compound 1 was used and by 40% when Compound 73 was used. The organic light emitting diode had superior I-V-L properties compared with an organic light emitting diode using NPB. Thus, an organic light emitting diode having low driving voltage, high efficiency, high brightness and long lifetime was prepared.

As described above, since the silanylamine-based compound of Formula 1 has excellent electrical properties and high charge transporting capability, embodiments thereof can be efficiently used as hole injecting materials, hole transporting materials, and/or emitting materials suitable for phosphorescent and fluorescent organic light emitting diodes emitting light of all types of colors including red, green, blue, and white. An organic light emitting diode having high efficiency, low driving voltage, and high brightness can be prepared by employing the silanylamine-based compound of Formula 1.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:
1. A silanylamine-based compound of Formula 1:

Formula 1

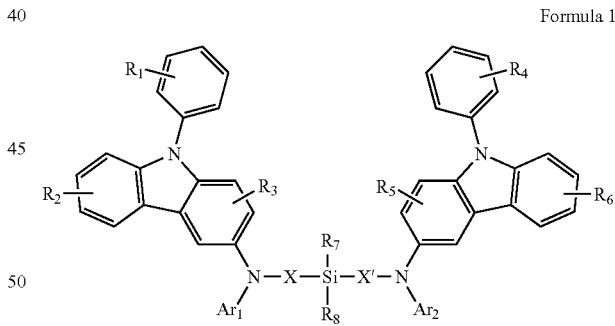

wherein $R_1$, $R_2$, $R_3$, $R_4$, $R_5$, $R_6$, $R_7$, and $R_8$ are each independently selected from the group consisting of a hydrogen atom, a phenyl group, a naphthyl group, a substituted or unsubstituted $C_1$-$C_{10}$ alkyl group, a substituted or unsubstituted $C_1$-$C_{10}$ alkoxy group, a fluorine atom, a cyano group, and an amine group, wherein adjacent $R_1$, $R_2$, $R_3$, $R_4$, $R_5$, $R_6$, $R_7$, and $R_8$ groups are optionally bonded with one another to form a saturated or unsaturated carbon ring, $Ar_1$ and $Ar_2$ are each independently selected from the group consisting of a substituted or unsubstituted $C_6$-$C_{20}$ aryl group, a substituted or unsubstituted $C_6$-$C_{20}$ aryloxy group, a substituted or unsubstituted $C_4$-$C_{20}$ heteroaryl group, and a substituted or unsubstituted C₄-C₂₀ condensed polycyclic group, and X and X' are each independently selected from the group consisting of a substituted or unsubstituted C₆-C₂₀ aryl group and a substituted or unsubstituted C₄-C₂₀ condensed polycyclic group.

2. The silanylamine-based compound of claim 1, wherein X is one of:

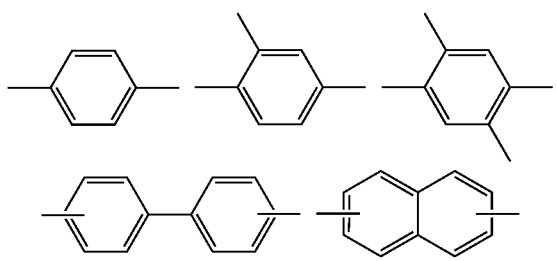

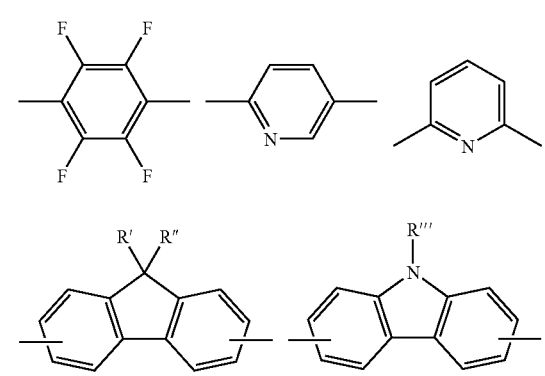

wherein R', R" and R"' are each independently selected from the group consisting of a hydrogen atom, a substituted or unsubstituted C₁-C₁₀ alkyl group, a substituted or unsubstituted C₂-C₁₀ alkenyl group, a substituted or unsubstituted C₂-C₁₀ alkynyl group, a substituted or unsubstituted C₁-C₁₀ alkoxy group, a substituted or unsubstituted C₆-C₁₀ aryloxy group, a substituted or unsubstituted C₆-C₁₀ aryl group, a substituted or unsubstituted C₄-C₁₀ heteroaryl group, and a substituted or unsubstituted C₄-C₁₀ condensed polycyclic group.

3. The silanylamine-based compound of claim 1, wherein X is one of:

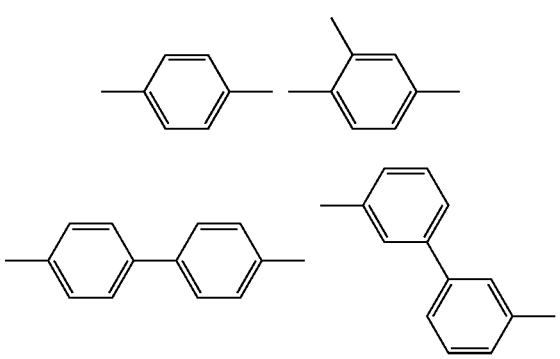

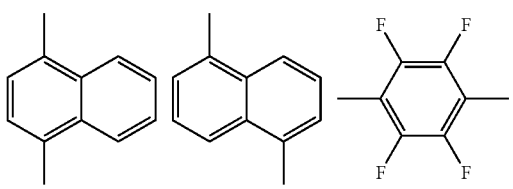

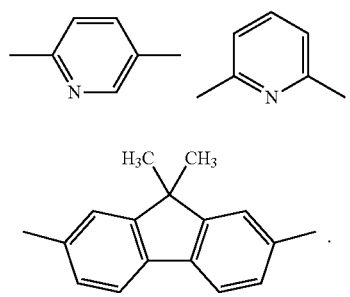

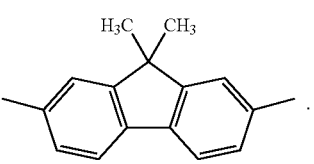

4. The silanylamine-based compound of claim 1, wherein Ar₁ and Ar₂ are each independently selected from the group consisting of a phenyl group, a C₁-C₅ alkylphenyl group, a C₁-C₅ alkoxyphenyl group, a cyanophenyl group, a phenoxyphenyl group, a fluorophenyl group, a naphthyl group, a C₁-C₅ alkylnaphthyl group, a C₁-C₅ alkoxynaphthyl group, a cyanonaphthyl group, a halonaphthyl group, a fluorenyl group, a carbazolyl group, a C₁-C₅ alkyl carbazolyl group, a biphenyl group, a C₁-C₅ alkyl biphenyl group, a C₁-C₅ alkoxy biphenyl group, and a pyridyl group.

5. The silanylamine-based compound of claim 1, wherein Ar₁ and Ar₂ are each independently selected from the group consisting of a phenyl group, an ethylphenyl group, an ethylbiphenyl group, an o-, m-, or p-fluorophenyl group, a dichlorophenyl group, a cyanophenyl group, a dicyanophenyl group, a trifluorophenyl group, a methoxyphenyl group, an o-, m-, or p-tolyl group, a mesityl group, a phenoxyphenyl group, an (α,α-dimethyl benzene)phenyl group, an (N,N'-dimethyl)aminophenyl group, an (N,N'-diphenyl)aminophenyl group, a pentalenyl group, a naphthyl group, a methylnaphthyl group, an anthracenyl group, an azulenyl group, a heptalenyl group, an acenaphthylenyl group, a fluorenyl group, an anthraquinonyl group, a phenanthryl group, a triphenylene group, a pentaphenyl group, a hexaphenyl group and a carbazolyl group.

6. The silanylamine-based compound of claim 1, wherein Ar₁ and Ar₂ are each independently a monocyclic to tricyclic aryl group, a fluorenyl group, a carbazolyl group, a phenyl group, a fluorophenyl group, a tolyl group, a naphthyl group, a biphenyl group and a cyanophenyl group, or a monocyclic to tricyclic aryl group comprising one to three substituents independently selected from the group consisting of a C₁-C₄ alkyl group, a C₁-C₅ alkoxy group, a cyano group, an amine group, a phenoxy group, a phenyl group, and a halogen atom.

7. The silanylamine-based compound of claim 1, wherein the silanylamine-based compound is one of the following structures:

1
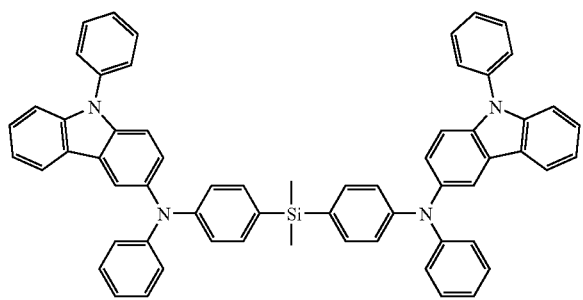
5
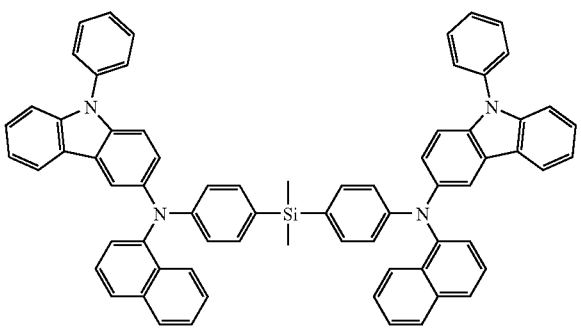
7
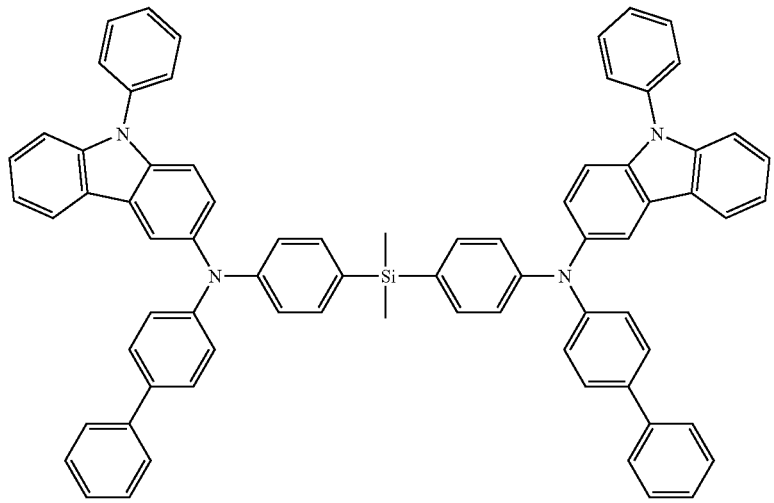
17
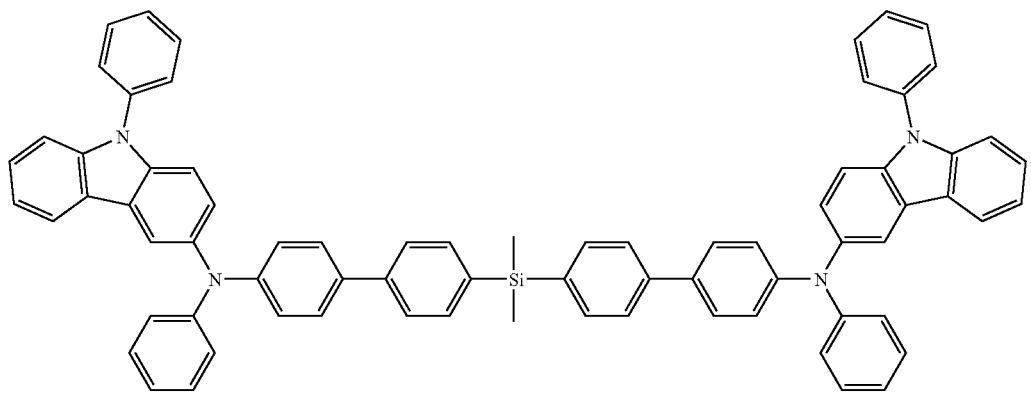
21
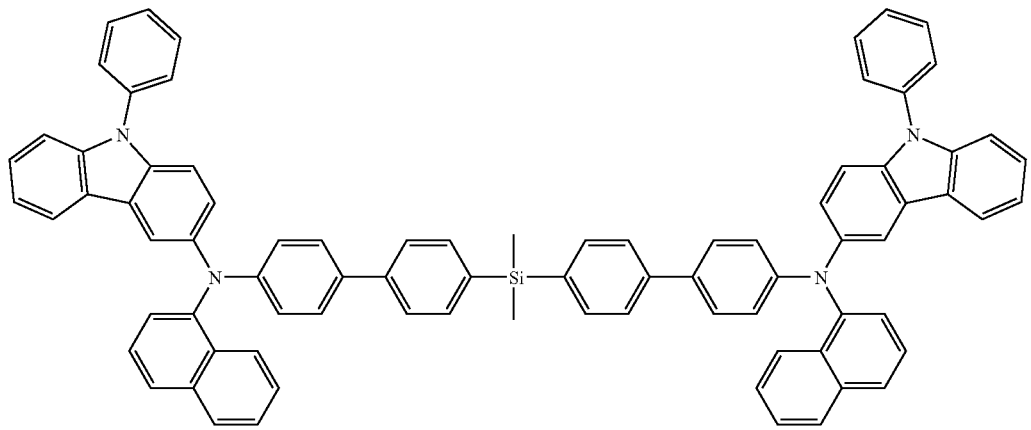

-continued
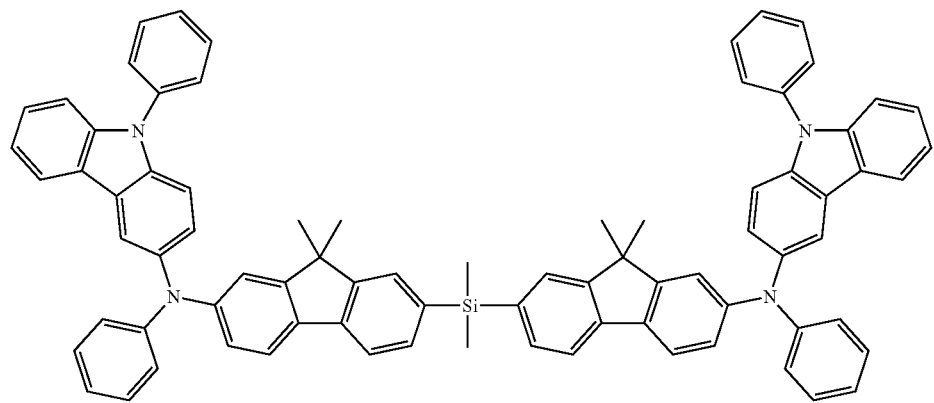
65
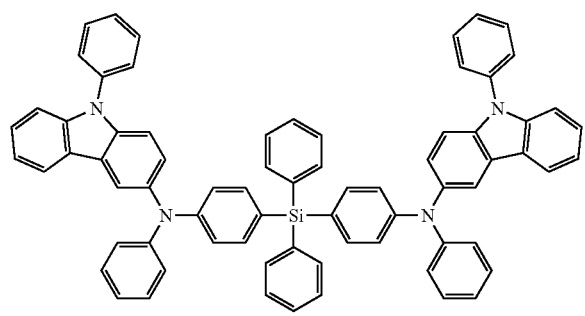
73
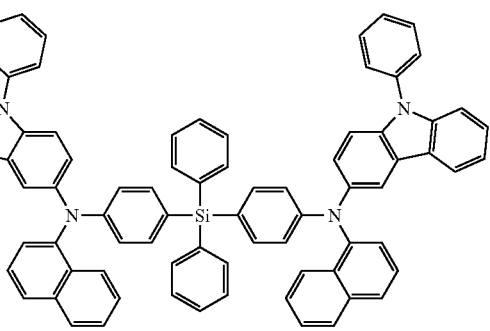
77
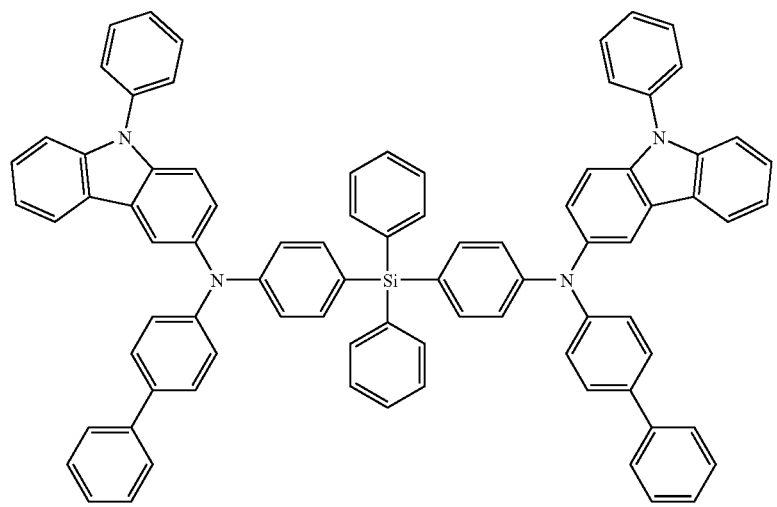
79
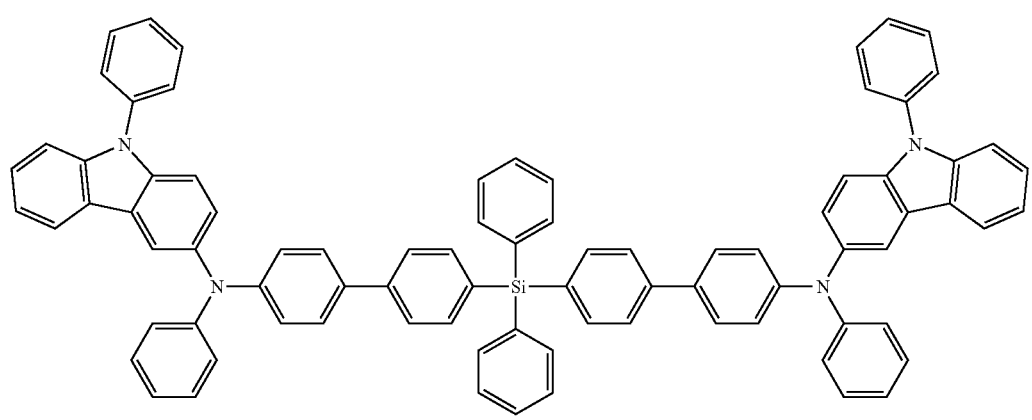
81

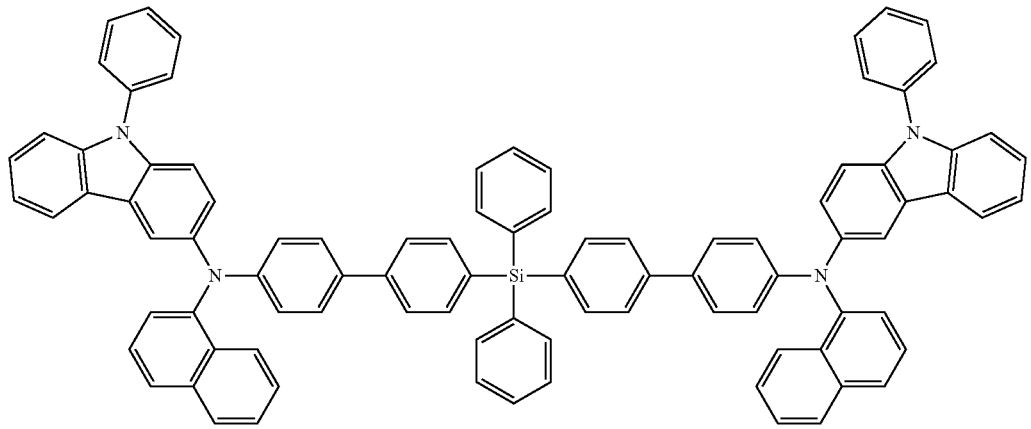

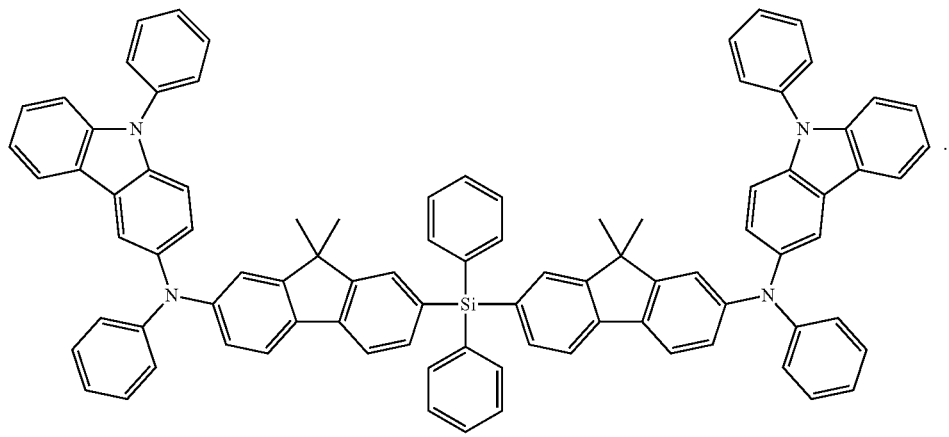

8. An organic light emitting diode comprising: a first electrode; a second electrode; and an organic layer interposed between the first electrode and the second electrode, wherein the organic layer comprises a silanylamine-based compound of claim 1.

9. The organic light emitting diode of claim 8, wherein the organic layer comprises at least one of a hole injection layer and a hole transport layer.

10. The organic light emitting diode of claim 8, wherein the organic layer comprises a single layer having both hole injecting and hole transporting properties.

11. The organic light emitting diode of claim 8, wherein the organic layer comprises an emitting layer.

12. The organic light emitting diode of claim 11, wherein the emitting layer comprises a phosphorescent or fluorescent dopant and a host comprising the silanylamine-based compound.

13. The organic light emitting diode of claim 8, wherein the organic light emitting diode comprises at least one of a first electrode/hole injection layer/emitting layer/second electrode structure, a first electrode/hole injection layer/hole transport layer/emitting layer/electron transport layer/second electrode structure, or a first electrode/hole injection layer/hole transport layer/emitting layer/electron transport layer/electron injection layer/second electrode structure.

14. The organic light emitting diode of claim 13, further comprising at least one of a hole blocking layer and an electron blocking layer.

15. The organic light emitting diode of claim 8, wherein X is one of:

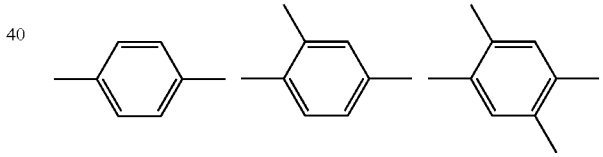

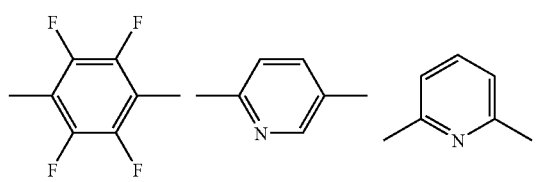

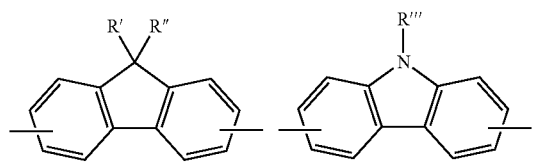

wherein R', R" and R'" are each independently selected from the group consisting of a hydrogen atom, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_6$-$C_{10}$ aryloxy group, a substituted or unsubstituted $C_6$-$C_{10}$ aryl group, a substituted or unsubstituted $C_4$-$C_{10}$ heteroaryl group, and a substituted or unsubstituted $C_4$-$C_{10}$ condensed polycyclic group.

16. The organic light emitting diode of claim 8, wherein X is one of:

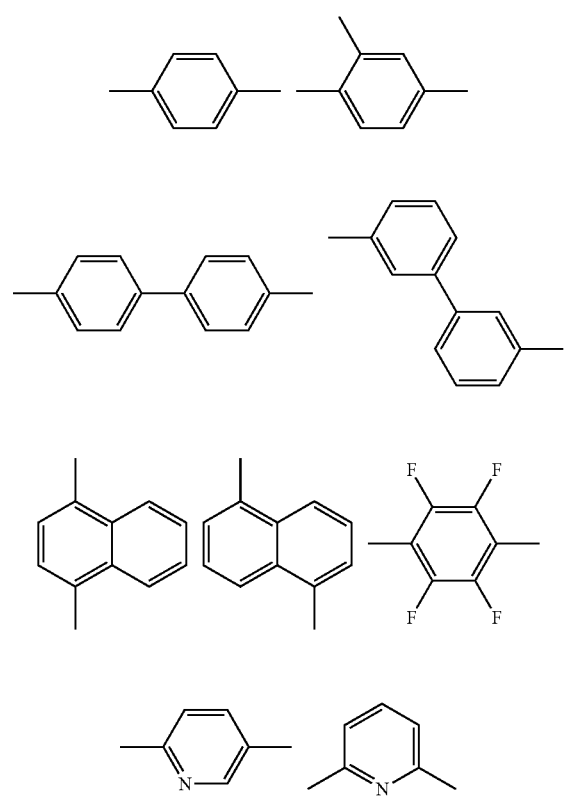

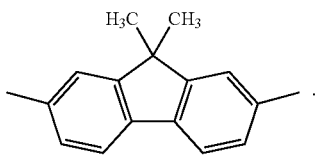

17. The organic light emitting diode of claim 8, wherein $Ar_1$ and $Ar_2$ are each independently selected from the group consisting of a phenyl group, a $C_1$-$C_5$ alkylphenyl group, a $C_1$-$C_5$ alkoxyphenyl group, a cyanophenyl group, a phenoxyphenyl group, a fluorophenyl group, a naphthyl group, a $C_1$-$C_5$ alkylnaphthyl group, a $C_1$-$C_5$ alkoxynaphthyl group, a cyanonaphthyl group, a halonaphthyl group, a fluorenyl group, a carbazolyl group, a $C_1$-$C_5$ alkyl carbazolyl group, a biphenyl group, a $C_1$-$C_5$ alkyl biphenyl group, a $C_1$-$C_5$ alkoxy biphenyl group, and a pyridyl group.

18. The organic light emitting diode of claim 8, wherein $Ar_1$ and $Ar_2$ are each independently selected from the group consisting of a phenyl group, an ethylphenyl group, an ethylbiphenyl group, an o-, m-, or p-fluorophenyl group, a dichlorophenyl group, a cyanophenyl group, a dicyanophenyl group, a trifluorophenyl group, a methoxyphenyl group, an o-, m-, or p-tolyl group, a mesityl group, a phenoxyphenyl group, an (α,α-dimethyl benzene)phenyl group, an (N,N'-dimethyl)aminophenyl group, an (N,N'-diphenyl)aminophenyl group, a pentalenyl group, a naphthyl group, a methylnaphthyl group, an anthracenyl group, an azulenyl group, a heptalenyl group, an acenaphthylenyl group, a fluorenyl group, an anthraquinonyl group, a phenanthryl group, a triphenylene group, a pentaphenyl group, a hexaphenyl group and a carbazolyl group.

19. The organic light emitting diode of claim 8, wherein $Ar_1$ and $Ar_2$ are each independently a monocyclic to tricyclic aryl group, a fluorenyl group, a carbazolyl group, a phenyl group, a fluorophenyl group, a tolyl group, a naphthyl group, a biphenyl group and a cyanophenyl group, or a monocyclic to tricyclic aryl group comprising one to three substituents independently selected from the group consisting of a $C_1$-$C_4$ alkyl group, a $C_1$-$C_5$ alkoxy group, a cyano group, an amine group, a phenoxy group, a phenyl group, and a halogen atom.

20. The organic light emitting diode of claim 8, wherein the compound of Formula 1 has one of the following structures:

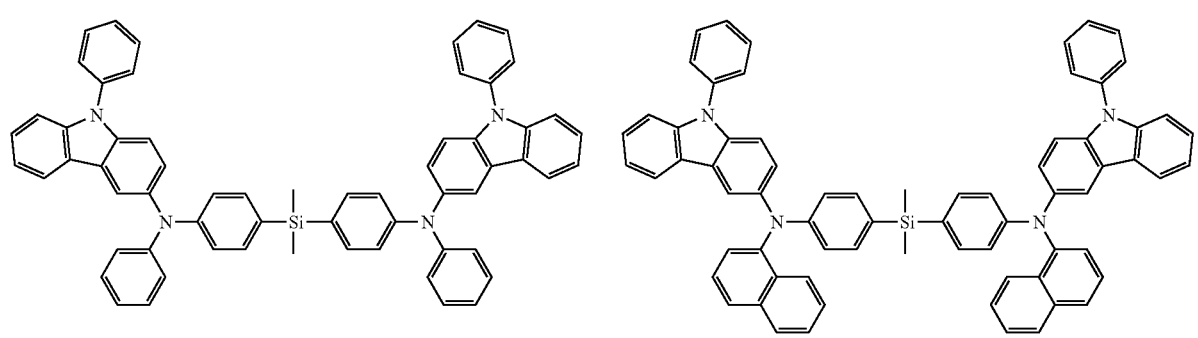

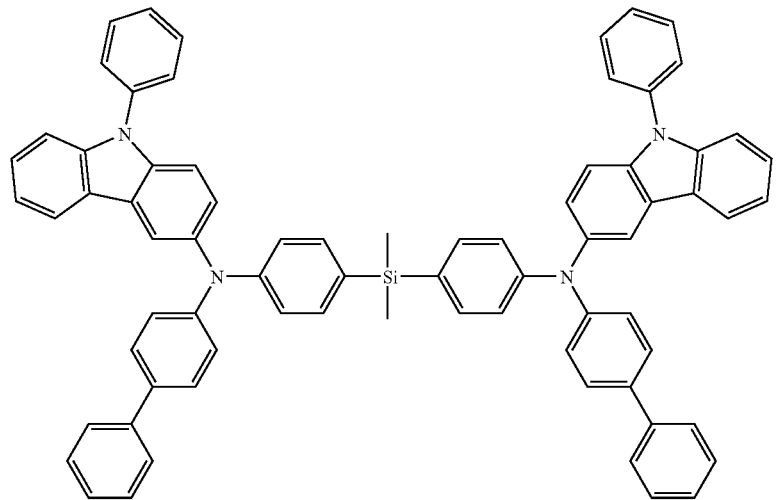
7
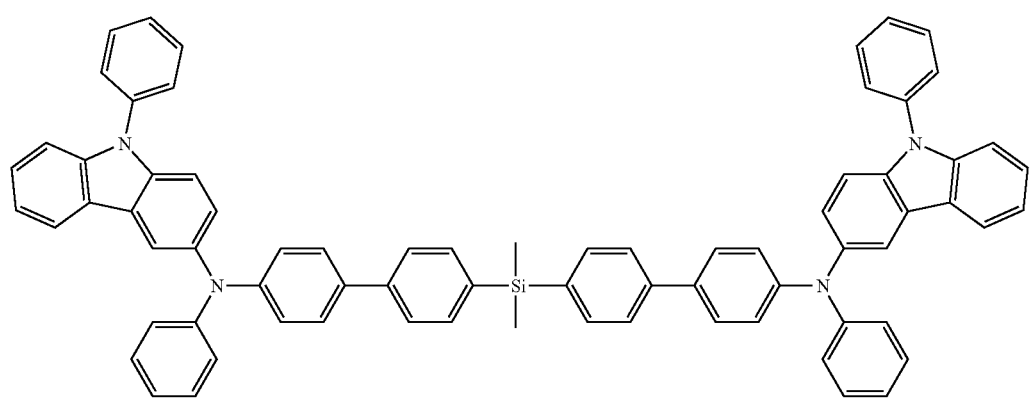
17
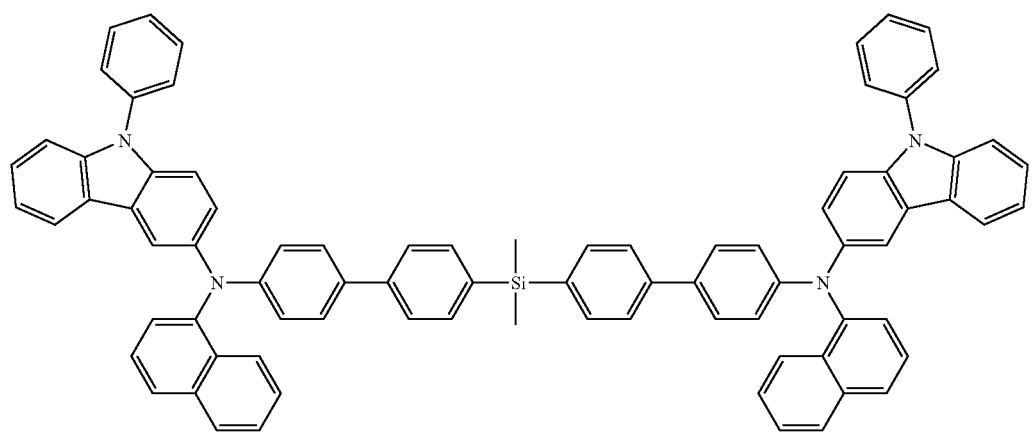
21

-continued
65
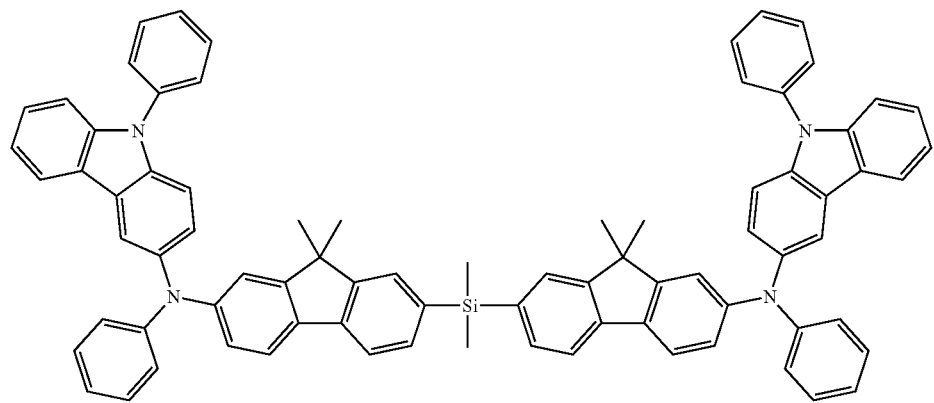
73
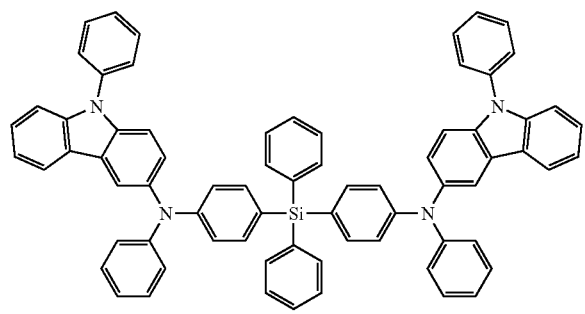
77
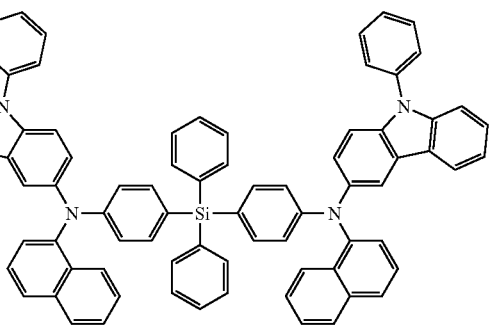
79
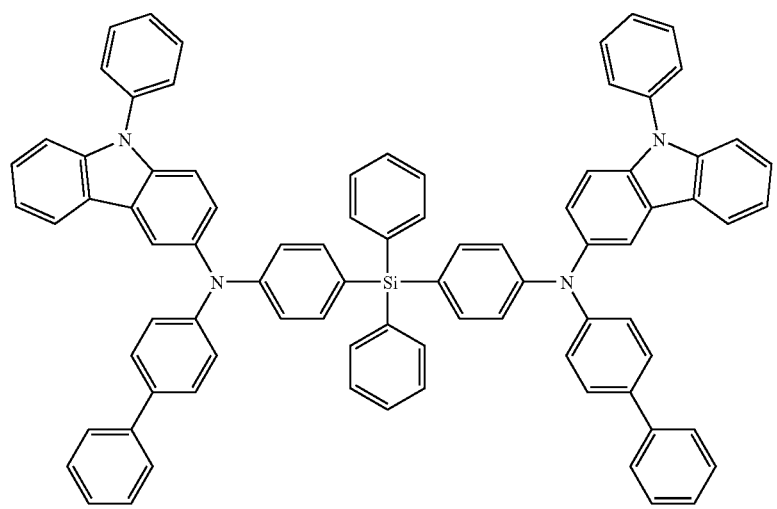
81
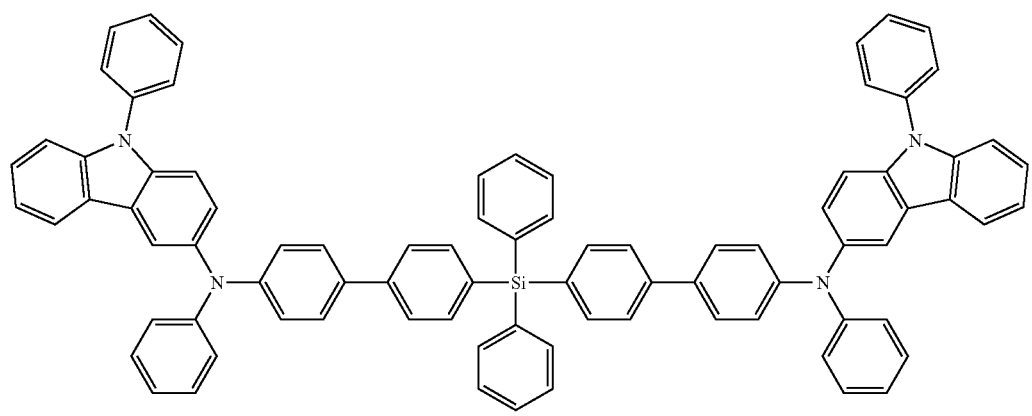

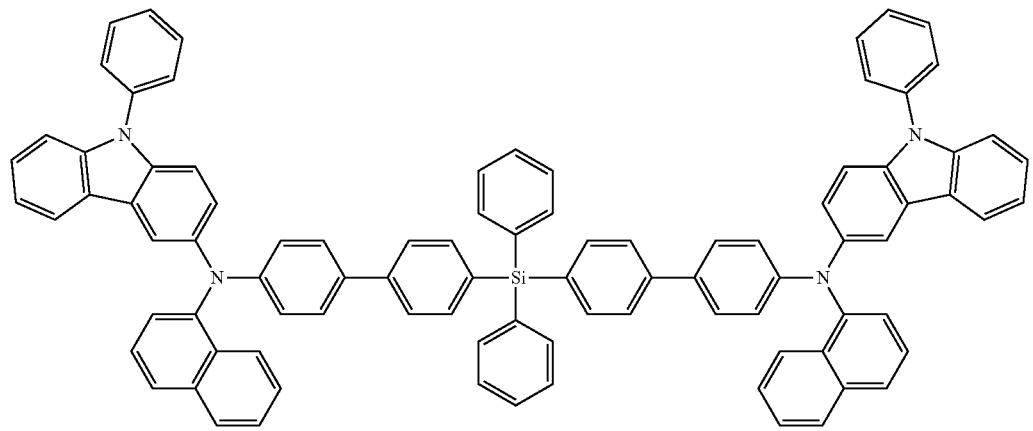
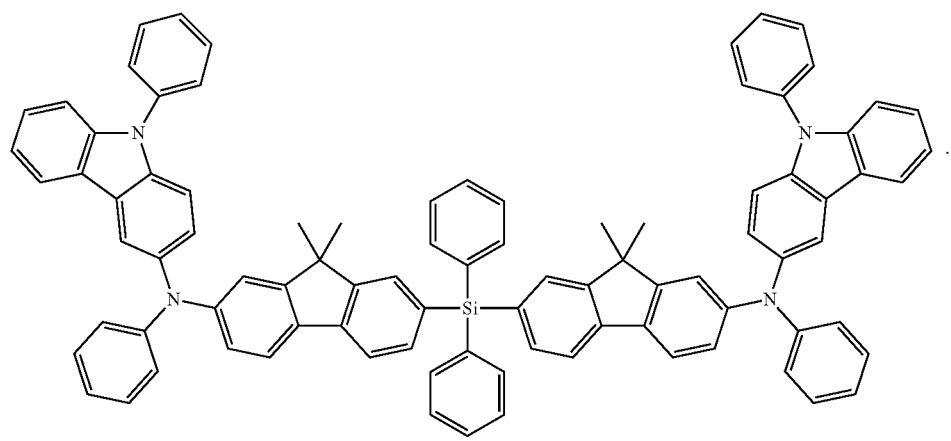
* * * * *

UNITED STATES PATENT AND TRADEMARK OFFICE
CERTIFICATE OF CORRECTION

PATENT NO. : 8,043,726 B2
APPLICATION NO. : 12/378601
DATED : October 25, 2011
INVENTOR(S) : Hwang et al.

Page 1 of 1

It is certified that error appears in the above-identified patent and that said Letters Patent is hereby corrected as shown below:

| Issued Patent | | Description of Discrepancy |
|---|---|---|
| Column | Line | |
| 12 | 60 | Change "mesithyl" to --mesityl--. |
| 12 | 63-64 | Change "athracenyl" to --anthracenyl--. |
| 89 | 6 | Change "diphenylbenzydine" to --diphenylbenzidine--. |
| 91 | 3-4 | Change "quinolinorate" to --quinolinolate--. |
| 91 | 16 | Change "The" to --the--. |
| 93 | 33 | Change "(ppm)'" to --(ppm):--. |
| 96 | 6 | Change "cd/A'" to --cd/A.--. |

Signed and Sealed this
Twenty-fourth Day of April, 2012

David J. Kappos
*Director of the United States Patent and Trademark Office*